(12) United States Patent
Kopping et al.

(10) Patent No.: US 10,272,103 B2
(45) Date of Patent: Apr. 30, 2019

(54) CROSSLINKED POLYVINYLAMINE, POLYALLYLAMINE, AND POLYETHYLENEIMINE FOR USE AS BILE ACID SEQUESTRANTS

(71) Applicant: Relypsa, Inc., Redwood City, CA (US)

(72) Inventors: Jordan Kopping, Weinheim (DE); Paul Mansky, San Francisco, CA (US); YongQi Mu, Los Altos, CA (US); Michael James Cope, Berkeley, CA (US); Elizabeth Goka, San Jose, CA (US); Angela Lee, San Jose, CA (US); Deidre Madsen, Los Altos, CA (US); Jun Shao, Fremont, CA (US); Kalpesh Biyani, Fremont, CA (US); Eric Connor, Los Gatos, CA (US); Scott Hecker, Del Mar, CA (US); Inez Lees, Menlo Park, CA (US); Grace May, San Francisco, CA (US); Faleh Salaymeh, Sunnyvale, CA (US); Hongmin Zhang, Fremont, CA (US); David Bergbreiter, College Station, TX (US)

(73) Assignee: Relypsa, Inc., Redwood City, CA (US)

(*) Notice: Subject to any disclaimer, the term of this patent is extended or adjusted under 35 U.S.C. 154(b) by 5 days.

(21) Appl. No.: 14/928,517

(22) Filed: Oct. 30, 2015

(65) Prior Publication Data
US 2016/0051576 A1    Feb. 25, 2016

Related U.S. Application Data

(63) Continuation of application No. 13/581,049, filed as application No. PCT/US2011/026099 on Feb. 24, 2011, now Pat. No. 9,181,364.

(60) Provisional application No. 61/307,811, filed on Feb. 24, 2010, provisional application No. 61/307,814, filed on Feb. 24, 2010.

(51) Int. Cl.
| | |
|---|---|
| A61K 31/785 | (2006.01) |
| C08F 226/02 | (2006.01) |
| A61K 45/06 | (2006.01) |
| C08F 222/38 | (2006.01) |
| C08F 20/52 | (2006.01) |
| C08F 22/38 | (2006.01) |
| C08F 232/08 | (2006.01) |

(52) U.S. Cl.
CPC ............ *A61K 31/785* (2013.01); *A61K 45/06* (2013.01); *C08F 20/52* (2013.01); *C08F 22/385* (2013.01); *C08F 222/385* (2013.01); *C08F 226/02* (2013.01); *C08F 232/08* (2013.01)

(58) Field of Classification Search
CPC ....... A61K 31/785; A61K 45/06; C08F 20/52; C08F 22/385; C08F 222/385; C08F 226/02; C08F 232/08
See application file for complete search history.

(56) References Cited

U.S. PATENT DOCUMENTS

| | | | |
|---|---|---|---|
| 5,236,701 | A | 8/1993 | St. Pierre et al. |
| 5,428,112 | A | 6/1995 | Ahlers et al. |
| 5,430,110 | A | 7/1995 | Ahlers et al. |
| 5,607,669 | A | 3/1997 | Mandeville, III et al. |
| 5,624,963 | A | 4/1997 | Mandeville, III et al. |
| 5,917,007 | A | 6/1999 | Mandeville, III et al. |
| 5,919,832 | A | 7/1999 | Mandeville, III et al. |
| 5,925,379 | A | 7/1999 | Mandeville, III et al. |
| 5,969,090 | A | 10/1999 | Mandeville, III et al. |
| 5,981,693 | A | 11/1999 | Mandeville, III et al. |
| 6,060,517 | A | 5/2000 | Mandeville, III et al. |
| 6,433,026 | B2 | 8/2002 | Mandeville, III et al. |
| 6,482,402 | B1 | 11/2002 | Kurtz et al. |
| 6,692,732 | B2 | 2/2004 | Fitzpatrick et al. |
| 7,135,598 | B2 | 11/2006 | Beckman et al. |
| 7,459,502 | B2 | 12/2008 | Connor et al. |
| 2004/0167338 | A1 | 8/2004 | Beckman et al. |
| 2005/0211624 | A1 | 9/2005 | Vane et al. |
| 2009/0047233 | A1 | 2/2009 | Huval et al. |
| 2009/0110907 | A1 | 4/2009 | Jiang et al. |
| 2015/0104510 | A1 | 4/2015 | Bhagat et al. |

FOREIGN PATENT DOCUMENTS

| | | |
|---|---|---|
| WO | 95/05184 A2 | 2/1995 |
| WO | 95/19384 | 7/1995 |
| WO | 96/39156 A2 | 12/1996 |
| WO | 96/39449 | 12/1996 |
| WO | 98/42355 A1 | 10/1998 |
| WO | 01/18012 A1 | 3/2001 |
| WO | 02/085382 A1 | 10/2002 |
| WO | 2006/050314 A2 | 5/2006 |

(Continued)

OTHER PUBLICATIONS

Partial Extended European Search Report dated Mar. 7, 2016 relating to European Application No. 15180706.2, 7 pages.

(Continued)

*Primary Examiner* — Matthew P Coughlin
*Assistant Examiner* — Thurman M Wheeler
(74) *Attorney, Agent, or Firm* — Stinson Leonard Street LLP

(57) ABSTRACT

The present invention provides a crosslinked amine and amide polymers effective for binding and removing bile salts from the gastrointestinal tract. These bile acid binding polymers or pharmaceutical compositions thereof can be administered to subjects to treat various conditions, including hypercholesteremia, diabetes, pruritis, irritable bowel syndrome-diarrhea (IBS-D), bile acid malabsorption, and the like.

16 Claims, No Drawings

(56) References Cited

FOREIGN PATENT DOCUMENTS

WO     2011/106545 A1     9/2011
WO     2011/106548 A1     9/2011

OTHER PUBLICATIONS

Asgari, F., et al., "Polymeric Sorbents for Bile Acids: 6. Effects of Cross-link Density on the Binding by Poly (acrylamide) Resins," IJBC, 1997, pp. 249-267, vol. 2, No. 4.
Bortel, E., et al., "N-vinylformamide-A New Environmentally Friendly Water-Soluble Monomer," Polimery, 2007, pp. 503-510, Nos. 7/8.
Cameron, N. S., et al., "Amphiphilic Block Copolymers as Bile Acid Sorbents: 1. Synthesis of Polystyrene-b-poly(N,N,N-trimethylammoniumethylene acrylamide chloride)," Biomacromolecules, Jan.-Feb. 2002, pp. 116-123, vol. 3, No. 1.
Cameron, N. S., et al., "Amphiphilic Block Copolymers as Bile Acid Sorbents: 2. Polystyrene-b-poly(N,N,N-trimethylammoniumethylene acrylamide chloride): Self-Assembly and Application to Serum Cholesterol Reduction," Biomacromolecules, Jan.-Feb. 2002, pp. 124-132, vol. 3, No. 1.
Cameron, N. S., et al., "Poly(N,N,N-trimethylammoniumalkyl acrylamide chloride) Based Hydrogels for Serum Cholesterol Reduction," Biomacromolecules, Jan.-Feb. 2004, pp. 24-31, vol. 5, No. 1.
International Search Report for International Patent Application No. PCT/US2011/026099, dated Sep. 14, 2011, 4 pages.
Lupasol(R) Product Range, BASF, Preliminary Technical Information, Sep. 1996, 10 pages.
Mandeville, W. H., et al., "The Sequestration of Bile Acids, A Non-Absorbed Method for Cholesterol Reduction. A Review," Current Pharmaceutical Design, 1997, pp. 15-28, vol. 3, No. 1.
Reynolds, D., D., et al., "The Preparation of Polyvinylamine, Polyvinylamine Salts, and Related Nitrogenous Resins," Journal of the American Chemical Society, Apr. 1947, pp. 911-915, vol. 69.
Shi, L., et al., "Synthesis and Characterization of Alkylated N-vinylformamide Monomers and Their Polymers," Journal of Polymer Science Part A: Polymer Chemistry, Oct. 1, 2004, pp. 4994-5004, vol. 42, No. 19.
Suwa, K., et al., "Synthesis and Functionalities of Poly(N-Vinylalkylamide). VI. A Novel Thermosensitive Hydrogel Cross-linked Poly(N-Vinylisobutyramide)," Journal of Polymer Science: Part A: Polymer Chemistry, 1997, pp. 3377-3384, vol. 35, No. 15.
Wu, G., et al., "Polymeric Sorbents for Bile Acids. 5. Polyacrylamide Resins with Ammonium-Containing Pendants," Langmuir, 1996, pp. 466-471, vol. 12, No. 2.
Yamamoto, K., et al., "Synthesis and Functionalities of Poly(N-vinylalkylamide). 13. Synthesis and Properties of Thermal and pH Stimuli-Responsive Poly(vinylamine) Copolymers," Macromolecules, 2001, pp. 8014-8020, vol. 34, No. 23.
Zhu, X. X., et al., "Bile Salt Anion Sorption by Polymeric Resins: Comparison of a Functionalized Polyacrylamide Resin with Cholestyramine," Journal of Colloid and Interface Science, 2000, pp. 282-288, vol. 232.

CROSSLINKED POLYVINYLAMINE, POLYALLYLAMINE, AND POLYETHYLENEIMINE FOR USE AS BILE ACID SEQUESTRANTS

CROSS-REFERENCE TO RELATED APPLICATIONS

This application is a continuation of U.S. Ser. No. 13/581,049, filed Oct. 11, 2012, which is a U.S. National of PCT Patent Application No. PCT/US2011/026099, filed on Feb. 24, 2011 which claims the benefit of U.S. Provisional Patent Application Ser. No. 61/307,811, filed on Feb. 24, 2010 and U.S. Provisional Patent Application Ser. No. 61/307,814, filed on Feb. 24, 2010. The entire content of the above applications are hereby incorporated by reference.

FIELD OF THE INVENTION

The present invention generally relates to polymers useful to bind bile acids in the gastrointestinal tract of a patient in need of bile acid removal. These polymers and pharmaceutical compositions thereof are useful to lower cholesterol, particularly, non-high density lipoprotein (non-HDL), or more particularly, low-density lipoprotein (LDL) cholesterol, in patients in need thereof.

BACKGROUND OF THE INVENTION

Cholesterol is used by the body as a structural component of cell membranes. In addition, it is a basic building block for the production of many hormones, adrenal steroids, vitamin D and bile acids. Elevated levels of cholesterol carried in particles of low density lipoprotein cholesterol (LDL-C), or less specifically, cholesterol not carried in particles of high-density cholesterol (non HDL-C) are associated with an increased risk of coronary heart disease. A direct link between high blood cholesterol and cardiovascular disease (CVD) has been confirmed for both non-statin and statin trials, consistent with a direct relationship between LDL-C lowering and CVD reduction. These studies as well as many others have led to recommendations by health authorities for lowering elevated total cholesterol and LDL-C levels.

Bile acids are amphipathic detergents with micelle-forming properties that are synthesized in the liver from cholesterol and solubilize lipids to aid in their uptake from the gastrointestinal lumen. Common bile acids found in man include unconjugated bile acids (for example cholic acid, chenodeoxycholic acid, deoxycholic acid, lithocholic acid) and conjugated bile acids (for example taurocholic acid, glycocholic acid, glycochenodeoxycholic acid, taurochenodeoxycholic acid, glycodeoxycholic acid, taurodeoxycholic acid, glycolithocholic acid, and taurolithocholic acid). After a meal, bile acids are released by the gall bladder. At ileal pH, the bile acids are predominantly deprotonated and are in their salt form. The majority of bile acids are reabsorbed, primarily by active transport in the distal ileum, with elimination in the feces being the primary route of cholesterol excretion.

A bile acid sequestrant can bind bile acids to prevent reabsorption of the bile acids and cause more of the bile acids to be excreted in the stool. The sequestrant reduces the amount of bile acids reabsorbed by the intestine and subsequently transported to the liver. To compensate for this disruption in enterohepatic circulation and consequent reduction of the endogenous bile acid pool, hepatic cholesterol 7-alpha-hydroxylase is upregulated. This results in additional conversion of cholesterol into bile acids, thereby restoring the bile acid pool. Upregulation of cholesterol conversion to bile acids also involves a cascade of signaling that results in up-regulation of liver LDL-receptors and consequent lowering of serum LDL-C levels, amongst other effects.

Many bile acid sequestrants do not have the binding capacity or binding affinity to reduce the serum LDL-cholesterol concentration significantly without requiring the patient to take large amounts of the sequestrant. A large dose requirement reduces patient compliance and tolerance. Thus, bile acid sequestrants capable of removing a greater amount of bile salts from the gastrointestinal tract with equal or lower doses are needed.

SUMMARY OF THE INVENTION

The present invention provides a crosslinked polymer that is effective for binding and removing bile salts from the gastrointestinal tract.

One aspect of the invention is a crosslinked amine polymer comprising a reaction product of a polymerization mixture comprising monomers, the polymer having the general structure of formula 1:

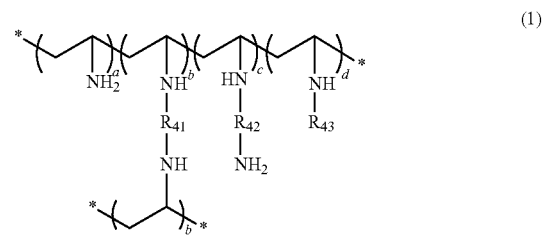

(1)

wherein $R_{41}$ is $C_5$ to $C_{12}$ alkylene or $C_5$ to $C_{12}$ alkylene wherein one or more of the —$CH_2$— groups of the alkylene group is replaced with an amide, a carbonyl, an ether, an ester, a cycloalkyl, an aryl, or a heterocyclo functional group; $R_{42}$ is $C_3$ to $C_{12}$ alkylene or $C_3$ to $C_{12}$ alkylene wherein one or more of the —$CH_2$— groups of the alkylene group is replaced with an amide, a carbonyl, an ether, an ester, a cycloalkyl, an aryl, or a heterocyclo functional group; $R_{43}$ is $C_3$ to $C_{12}$ alkyl, aralkyl or $C_3$ to $C_{12}$ alkyl wherein one or more of the —$CH_2$— groups of the alkyl group is replaced with an amide, a carbonyl, an ether, an ester, a cycloalkyl, an aryl, or a heterocyclo functional group; b is 1.5 to 25 mole percent based on the ratio of monomers added to the polymerization mixture; and each of a, c and d is independently 0 to 97 mole percent based on the ratio of monomers added to the polymerization mixture.

Another aspect is a crosslinked amine polymer comprising a reaction product of a polymerization mixture comprising a monomer of Formula 2

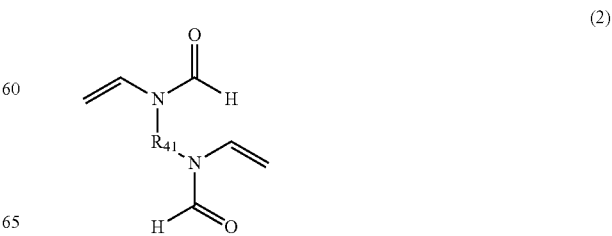

(2)

wherein $R_{41}$ is $C_8$ to $C_{12}$ alkylene or $C_8$ to $C_{12}$ alkylene wherein one or more of the —$CH_2$— groups of the alkylene group is replaced with an amide, a carbonyl, an ether, an ester, a cycloalkyl, an aryl, or a heterocyclo functional group.

A further aspect is a crosslinked amine polymer comprising a reaction product of a polymerization mixture comprising a monomer of Formula 3

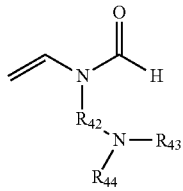

(3)

wherein $R_{42}$ is $C_3$ to $C_{12}$ alkylene or $C_3$ to $C_{12}$ alkylene wherein one or more of the —$CH_2$— groups of the alkylene group is replaced with an amide, a carbonyl, an ether, an ester, a cycloalkyl, an aryl, or a heterocyclo functional group; $R_{43}$ is hydrogen or a protecting group; and $R_{44}$ is a protecting group.

Yet another aspect is a crosslinked amine polymer can also comprising a reaction product of a polymerization mixture comprising a monomer of Formula 4 and 1 to 25 mole percent of a monomer of Formula 2 based on the total monomers added to the polymerization mixture, the monomers having the formula:

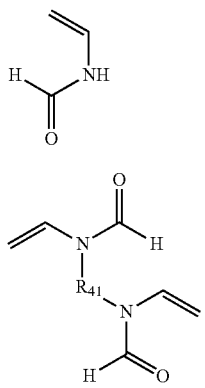

(4)

(2)

wherein $R_{41}$ is $C_5$ to $C_{12}$ alkylene or $C_5$ to $C_{12}$ alkylene wherein one or more of the —$CH_2$— groups of the alkylene group is replaced with an amide, a carbonyl, an ether, an ester, a cycloalkyl, an aryl, or a heterocyclo functional group.

A further aspect of the invention is a crosslinked amine polymer comprising a reaction product of a polymerization mixture comprising a monomer of Formula 4 and a monomer of Formula 2

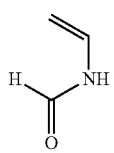

(4)

-continued

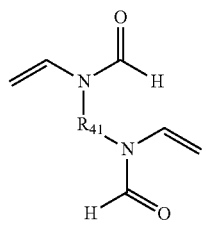

(2)

wherein $R_{41}$ is $C_3$ to $C_{16}$ alkylene or $C_3$ to $C_{16}$ alkylene wherein one or more of the —$CH_2$— groups of the alkylene group is replaced with an amide, a carbonyl, an ether, an ester, a cycloalkyl, an aryl, or a heterocyclo functional group; wherein a portion of the nitrogen atoms of the crosslinked amine polymer are substituted with a ligand selected from aminoalkyl, aryl, arylalkyl, cycloalkyl, (cycloalkyl)alkyl, heterocyclo, heterocycloalkyl, (trialkylammonio)alkyl, 2-(protected amino)-m-(heterocyclo)-1-oxo$C_m$alkyl, 2-(protected amino)-1-oxo$C_m$alkyl, 2-(protected amino)-3-methyl-1-oxo$C_m$alkyl, 2-(protected amino)-4-methyl-1-oxo$C_m$alkyl, 2-(protected amino)-1-oxo-m-aryl$C_m$alkyl, 2-(protected amino)-m-(alkylthio)-1-oxo$C_m$alkyl, 2-(protected amino)-m-(aryl)-1-oxo$C_m$alkyl, 2-(protected amino)-m-carboxy-1-oxo$C_m$alkyl, 2-(protected amino)-m-guanidino-1-oxo$C_m$alkyl, 2-(protected amino)-(m-1)-hydroxy-1-oxo$C_m$alkyl, 2-(protected amino)-m-hydroxy-1-oxo$C_m$alkyl, 2-(protected amino)-m-mercapto-1-oxo$C_m$alkyl, m-(alkylamino)-m-oxo$C_m$alkyl, m-(alkylheterocyclo)$C_m$alkyl, m-amino-2-(protected amino)-1-oxo$C_m$alkyl, m-amino-2-(protected amino)-1,m-dioxo$C_m$alkyl, m-(x-amino$C_x$alkyl)heterocyclo$C_m$alkyl, (m-1)-amino-m-(heterocyclo)-1-oxo$C_m$alkyl, m-(arylalkylamino)-m-oxo$C_m$alkyl, m-(x-(alkylthio)$C_x$alkylamino)-m-oxo$C_m$alkyl, m-(x-amino$C_x$alkylamino)-m-oxo$C_m$alkyl, m-(x-amino-x-oxo$C_x$alkylamino)-m-oxo$C_m$alkyl, m-(x-carboxy$C_x$alkylamino)-m-oxo$C_m$alkyl, m-(heterocycloalkylamino)-m-oxo$C_m$alkyl, m-(x-hydroxy$C_x$alkylamino)-m-oxo$C_m$alkyl, m-((x-1)-hydroxy$C_x$alkylamino)-m-oxo$C_m$alkyl, m-(x-mercapto$C_x$alkylamino)-m-oxo$C_m$alkyl, m-(x-trialkylammonio$C_x$alkyl)heterocyclo$C_m$alkyl, m-(x-(2-(alkoxy)benzamido)$C_x$alkylamino)-m-oxo$C_m$alkyl, m-(x-(3-(alkoxy)benzamido)$C_x$alkylamino)-m-oxo$C_m$alkyl, m-(x-(4-(alkoxy)benzamido)$C_x$alkylamino)-m-oxo$C_m$alkyl, a ligand of formula 6

$$*—R_{46}—R_{47}—R_{48}$$ (6)

or a combination thereof, wherein $R_{46}$ is $C_6$ to $C_{16}$ alkylene, $R_{47}$ is 1,y-bis(1-methylpiperidin-4-yl)$C_y$alkylene, $R_{48}$ is $C_6$ to $C_{16}$ alkyl, m is an integer from 3 to 12, x is an integer from 1 to 12, y is an integer from 1 to 14, and z is an integer from 1 to 16.

Another aspect is a crosslinked amine polymer comprise repeat units derived from reaction of a vinyl amine repeat unit and a crosslinking agent, wherein the vinyl amine repeat unit has the formula:

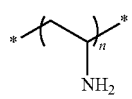

(7)

and the crosslinking agent is X—$R_1$—X or epihalohydrin wherein $R_1$ is $C_3$ to $C_{16}$ alkylene or $C_3$ to $C_{16}$ alkylene wherein one or more of the —CH$_2$— groups of the alkylene group is replaced with an amide, a carbonyl, an ether, an ester, a cycloalkyl, an aryl, or a heterocyclo functional group, each X is independently a leaving group, and a portion of the nitrogen atoms of the crosslinked amine polymer are substituted with a ligand selected from aminoalkyl, aryl, arylalkyl, cycloalkyl, (cycloalkyl)alkyl, heterocyclo, heterocycloalkyl, (trialkylammonio)alkyl, 2-(protected amino)-m-(heterocyclo)-1-oxoC$_m$alkyl, 2-(protected amino)-1-oxoC$_m$alkyl, 2-(protected amino)-3-methyl-1-oxoC$_m$alkyl, 2-(protected amino)-4-methyl-1-oxoC$_m$alkyl, 2-(protected amino)-1-oxo-m-arylC$_m$alkyl, 2-(protected amino)-m-(alkylthio)-1-oxoC$_m$alkyl, 2-(protected amino)-m-(aryl)-1-oxoC$_m$alkyl, 2-(protected amino)-m-carboxy-1-oxoC$_m$alkyl, 2-(protected amino)-m-guanidino-1-oxoC$_m$alkyl, 2-(protected amino)-(m-1)-hydroxy-1-oxoC$_m$alkyl, 2-(protected amino)-m-hydroxy-1-oxoC$_m$alkyl, 2-(protected amino)-m-mercapto-1-oxoC$_m$alkyl, m-(alkylamino)-m-oxoC$_m$alkyl, m-(alkylheterocyclo)C$_m$alkyl, m-amino-2-(protected amino)-1-oxoC$_m$alkyl, m-amino-2-(protected amino)-1,m-dioxoC$_m$alkyl, m-(x-aminoC$_x$alkyl)heterocycloC$_m$alkyl, (m-1)-amino-m-(heterocyclo)-1-oxoC$_m$alkyl, m-(arylalkylamino)-m-oxoC$_m$alkyl, m-(x-(alkylthio)C$_x$-alkylamino)-m-oxoC$_m$alkyl, m-(x-aminoC$_x$alkylamino)-m-oxoC$_m$alkyl, m-(x-amino-x-oxoC$_x$alkylamino)-m-oxoC$_m$alkyl, m-(x-carboxyC$_x$alkylamino)-m-oxoC$_m$alkyl, m-(heterocycloalkylamino)-m-oxoC$_m$alkyl, m-(x-hydroxyC$_x$alkylamino)-m-oxoC$_m$alkyl, m-((x-1)-hydroxyC$_x$alkylamino)-m-oxoC$_m$alkyl, m-(x-mercaptoC$_x$alkylamino)-m-oxoC$_m$alkyl, m-(x-trialkylammonioC$_x$alkyl)heterocycloC$_m$alkyl, m-(x-(2-(alkoxy)benzamido)C$_x$alkylamino)-m-oxoC$_m$alkyl, m-(x-(3-(alkoxy)benzamido)C$_x$alkylamino)-m-oxoC$_m$alkyl, m-(x-(4-(alkoxy)benzamido)C$_x$alkylamino)-m-oxoC$_m$alkyl, a ligand of formula 6

or a combination thereof, wherein R$_{46}$ is C$_6$ to C$_{16}$ alkylene, R$_{47}$ is 1,y-bis(1-methylpiperidin-4-yl)C$_y$alkylene, R$_{48}$ is C$_6$ to C$_{16}$ alkyl, m is an integer from 3 to 12, x is an integer from 1 to 12, y is an integer from 1 to 14, and z is an integer from 1 to 16.

Yet another aspect is a crosslinked acrylamide polymer comprising a reaction product of a polymerization mixture comprising monomers, the polymer having the general structure of formula 9:

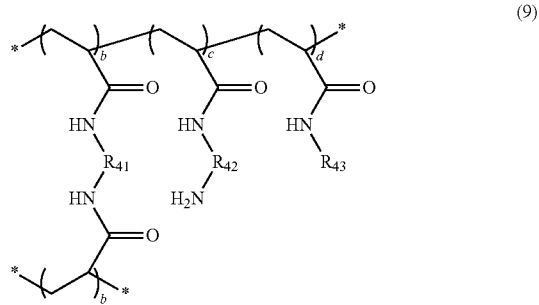

wherein R$_{41}$ is C$_5$ to C$_{12}$ alkylene or C$_5$ to C$_{12}$ alkylene wherein one or more of the —CH$_2$— groups of the alkylene group is replaced with an amide, a carbonyl, an ether, an ester, a cycloalkyl, an aryl, or a heterocyclo functional group; R$_{42}$ is C$_3$ to C$_{12}$ alkylene or C$_3$ to C$_{12}$ alkylene wherein one or more of the —CH$_2$— groups of the alkylene group is replaced with an amide, a carbonyl, an ether, an ester, a cycloalkyl, an aryl, or a heterocyclo functional group; R$_{43}$ is C$_3$ to C$_{12}$ alkyl, aralkyl or C$_3$ to C$_{20}$ alkyl wherein one or more of the —CH$_2$— groups of the alkyl group is replaced with an amide, a carbonyl, an ether, an ester, a cycloalkyl, an aryl, or a heterocyclo functional group; b is 1 to 25 mole percent based on the ratio of monomers added to the polymerization mixture; and each of c and d is independently 0 to 99 mole percent based on the ratio of monomers added to the polymerization mixture.

A further aspect is a crosslinked acrylamide polymer comprising a reaction product of a polymerization mixture comprising a monomer of Formula 10 and 1 to 25 mole percent of a monomer of Formula 11 based on the total monomers added to the polymerization mixture, the monomers having the formula:

wherein R$_{40}$ is hydrogen or —R$_{42}$NR$_{43}$R$_{44}$; R$_{41}$ is C$_5$ to C$_{12}$ alkylene or C$_5$ to C$_{12}$ alkylene wherein one or more of the —CH$_2$— groups of the alkylene group is replaced with an amide, a carbonyl, an ether, an ester, a cycloalkyl, an aryl, or a heterocyclo functional group; R$_{42}$ is C$_2$ to C$_{12}$ alkylene or C$_2$ to C$_{12}$ alkylene wherein one or more of the —CH$_2$— groups of the alkylene group is replaced with an amide, a carbonyl, an ether, an ester, a cycloalkyl, an aryl, or a heterocyclo functional group; R$_{43}$ is hydrogen or a protecting group; and R$_{44}$ is a protecting group.

A further aspect is a crosslinked amine polymer comprising repeat units of polyallylamine and a crosslinking unit of —R$_{50}$— derived from reaction of a crosslinking agent and the polyallylamine, the polyallylamine of formula 14 having the formula:

wherein n is an integer; and R$_{50}$ is C$_8$ to C$_{50}$ alkylene wherein one or more of the —CH$_2$— groups of the alkylene group is replaced with an amide, an ether, an ester, a cycloalkyl, or a heterocyclo functional group.

Another aspect of the invention is a crosslinked amine polymer comprising repeat units derived from reaction of an allyl amine repeat unit and a crosslinking agent, wherein the allyl amine repeat unit has the formula:

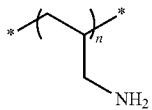
(14)

wherein n is an integer, and the crosslinking agent is X—$R_1$—X or epihalohydrin wherein $R_1$ is independently $C_2$ to $C_{50}$ alkylene or $C_2$ to $C_{50}$ alkylene wherein one or more of the —$CH_2$— groups of the alkylene group is replaced with an amide, a carbonyl, an ether, an ester, a cycloalkyl, an aryl, or a heterocyclo functional group, each X is independently a leaving group, and a portion of the nitrogen atoms of the crosslinked amine polymer are substituted with a ligand selected from aminoalkyl, aryl, arylalkyl, cycloalkyl, (cycloalkyl)alkyl, heterocyclo, heterocycloalkyl, (trialkylammonio)alkyl, 2-(protected amino)-m-(heterocyclo)-1-oxo$C_m$alkyl, 2-(protected amino)-1-oxo$C_m$alkyl, 2-(protected amino)-3-methyl-1-oxo$C_m$alkyl, 2-(protected amino)-4-methyl-1-oxo$C_m$alkyl, 2-(protected amino)-1-oxo-m-aryl$C_m$alkyl, 2-(protected amino)-m-(alkylthio)-1-oxo$C_m$alkyl, 2-(protected amino)-m-(aryl)-1-oxo$C_m$alkyl, 2-(protected amino)-m-carboxy-1-oxo$C_m$alkyl, 2-(protected amino)-m-guanidino-1-oxo$C_m$alkyl, 2-(protected amino)-(m-1)-hydroxy-1-oxo$C_m$alkyl, 2-(protected amino)-m-hydroxy-1-oxo$C_m$alkyl, 2-(protected amino)-m-mercapto-1-oxo$C_m$alkyl, m-(alkylamino)-m-oxo$C_m$alkyl, m-(alkylheterocyclo)$C_m$alkyl, m-amino-2-(protected amino)-1-oxo$C_m$alkyl, m-amino-2-(protected amino)-1,m-dioxo$C_m$alkyl, m-(x-amino$C_x$alkyl)heterocyclo$C_m$alkyl, (m-1)-amino-m-(heterocyclo)-1-oxo$C_m$alkyl, m-(arylalkylamino)-m-oxo$C_m$alkyl, m-(x-(alkylthio)$C_x$alkylamino)-m-oxo$C_m$alkyl, m-(x-amino$C_x$alkylamino)-m-oxo$C_m$alkyl, m-(x-amino-x-oxo$C_x$alkylamino)-m-oxo$C_m$alkyl, m-(x-carboxy$C_x$alkylamino)-m-oxo$C_m$alkyl, m-(heterocycloalkylamino)-m-oxo$C_m$alkyl, m-(x-hydroxy$C_x$alkylamino)-m-oxo$C_m$alkyl, m-((x-1)-hydroxy$C_x$alkylamino)-m-oxo$C_m$alkyl, m-(x-mercapto$C_x$alkylamino)-m-oxo$C_m$alkyl, m-(x-trialkylammonio$C_x$alkyl)heterocyclo$C_m$alkyl, m-(x-(2-(alkoxy)benzamido)$C_x$alkylamino)-m-oxo$C_m$alkyl, m-(x-(3-(alkoxy)benzamido)$C_x$alkylamino)-m-oxo$C_m$alkyl, m-(x-(4-(alkoxy)benzamido)$C_x$alkylamino)-m-oxo$C_m$alkyl, a ligand of formula 6

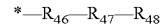
(6)

or a combination thereof, wherein $R_{46}$ is $C_6$ to $C_{16}$ alkylene, $R_{47}$ is 1,y-bis(1-methylpiperidin-4-yl)$C_y$alkylene, $R_{48}$ is $C_6$ to $C_{16}$ alkyl, m is an integer from 3 to 12, x is an integer from 1 to 12, y is an integer from 1 to 14, and z is an integer from 1 to 16.

Another aspect is a crosslinked amine polymer comprising repeat units of polyethyleneimine and a crosslinking agent, wherein the polyethyleneimine has the formula:

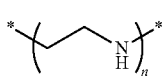
(15)

wherein n is an integer, and the crosslinking agent is X—$R_1$—X or epihalohydrin wherein $R_1$ is independently $C_2$ to $C_{50}$ alkylene or $C_2$ to $C_{50}$ alkylene wherein one or more of the —$CH_2$— groups of the alkylene group is replaced with an amide, a carbonyl, an ether, an ester, a cycloalkyl, an aryl, or a heterocyclo functional group, each X is independently a leaving group, and a portion of the nitrogen atoms of the crosslinked amine polymer are substituted with a ligand selected from aminoalkyl, aryl, arylalkyl, cycloalkyl, (cycloalkyl)alkyl, heterocyclo, heterocycloalkyl, (trialkylammonio)alkyl, 2-(protected amino)-m-(heterocyclo)-1-oxo$C_m$alkyl, 2-(protected amino)-1-oxo$C_m$alkyl, 2-(protected amino)-3-methyl-1-oxo$C_m$alkyl, 2-(protected amino)-4-methyl-1-oxo$C_m$alkyl, 2-(protected amino)-1-oxo-m-aryl$C_m$alkyl, 2-(protected amino)-m-(alkylthio)-1-oxo$C_m$alkyl, 2-(protected amino)-m-(aryl)-1-oxo$C_m$alkyl, 2-(protected amino)-m-carboxy-1-oxo$C_m$alkyl, 2-(protected amino)-m-guanidino-1-oxo$C_m$alkyl, 2-(protected amino)-(m-1)-hydroxy-1-oxo$C_m$alkyl, 2-(protected amino)-m-hydroxy-1-oxo$C_m$alkyl, 2-(protected amino)-m-mercapto-1-oxo$C_m$alkyl, m-(alkylamino)-m-oxo$C_m$alkyl, m-(alkylheterocyclo)$C_m$alkyl, m-amino-2-(protected amino)-1-oxo$C_m$alkyl, m-amino-2-(protected amino)-1,m-dioxo$C_m$alkyl, m-(x-amino$C_x$alkyl)heterocyclo$C_m$alkyl, (m-1)-amino-m-(heterocyclo)-1-oxo$C_m$alkyl, m-(arylalkylamino)-m-oxo$C_m$alkyl, m-(x-(alkylthio)$C_x$alkylamino)-m-oxo$C_m$alkyl, m-(x-amino$C_x$alkylamino)-m-oxo$C_m$alkyl, m-(x-amino-x-oxo$C_x$alkylamino)-m-oxo$C_m$alkyl, m-(x-carboxy$C_x$alkylamino)-m-oxo$C_m$alkyl, m-(heterocycloalkylamino)-m-oxo$C_m$alkyl, m-(x-hydroxy$C_x$alkylamino)-m-oxo$C_m$alkyl, m-((x-1)-hydroxy$C_x$alkylamino)-m-oxo$C_m$alkyl, m-(x-mercapto$C_x$alkylamino)-m-oxo$C_m$alkyl, m-(x-trialkylammonio$C_x$alkyl)heterocyclo$C_m$alkyl, m-(x-(2-(alkoxy)benzamido)$C_x$alkylamino)-m-oxo$C_m$alkyl, m-(x-(3-(alkoxy)benzamido)$C_x$alkylamino)-m-oxo$C_m$alkyl, m-(x-(4-(alkoxy)benzamido)$C_x$alkylamino)-m-oxo$C_m$alkyl, a ligand of formula 6

$$*—R_{46}—R_{47}—R_{48} \qquad (6)$$

or a combination thereof, wherein $R_{46}$ is $C_6$ to $C_{16}$ alkylene, $R_{47}$ is 1,y-bis(1-methylpiperidin-4-yl)$C_y$alkylene, $R_{48}$ is $C_6$ to $C_{16}$ alkyl, m is an integer from 3 to 12, x is an integer from 1 to 12, y is an integer from 1 to 14, and z is an integer from 1 to 16.

Other objects and features will be in part apparent and in part pointed out hereinafter.

DESCRIPTION OF THE PREFERRED EMBODIMENTS

The present invention is a polymer useful for binding bile salts, pharmaceutical compositions comprising the polymer, and methods of treating hypercholesterolemia, diabetes or other conditions that might benefit from bile acid sequestration in the gastrointestinal tract and/or increased fecal excretion of bile acids and/or bile acid metabolites, by administering the polymer to an animal subject in need thereof. The polymers exhibit increased affinity and/or capacity for binding bile salts and/or their retention as compared to commercial bile acid sequestrants. The polymers have a combination of hydrogen bonding and electrostatic properties, charged nitrogen atoms, hydrophobicity and/or polymer architecture to provide such increased affinity and/or capacity for bile salts. The terms "bile acid" and "bile salt" are used interchangeably herein and those of skill in the art will understand that a bile acid will be present in salt form and, to a lesser degree, in the protonated form in the gastrointestinal tract.

One aspect of the invention is a crosslinked amine polymer comprising a reaction product of a polymerization mixture comprising monomers, the polymer having the general structure of formula 1:

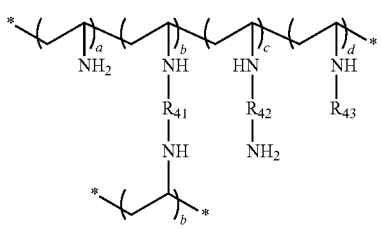
(1)

wherein $R_{41}$ is $C_5$ to $C_{12}$ alkylene or $C_5$ to $C_{12}$ alkylene wherein one or more of the —$CH_2$— groups of the alkylene group is replaced with an amide, a carbonyl, an ether, an ester, a cycloalkyl, an aryl, or a heterocyclo functional group; $R_{42}$ is $C_3$ to $C_{12}$ alkylene or $C_3$ to $C_{12}$ alkylene wherein one or more of the —$CH_2$— groups of the alkylene group is replaced with an amide, a carbonyl, an ether, an ester, a cycloalkyl, an aryl, or a heterocyclo functional group; $R_{43}$ is $C_3$ to $C_{12}$ alkyl, aralkyl or $C_3$ to $C_{12}$ alkyl wherein one or more of the —$CH_2$— groups of the alkyl group is replaced with an amide, a carbonyl, an ether, an ester, a cycloalkyl, an aryl, or a heterocyclo functional group; b is 1.5 to 25 mole percent based on the ratio of monomers added to the polymerization mixture; and each of a, c and d is independently 0 to 97 mole percent based on the ratio of monomers added to the polymerization mixture.

In some embodiments, the amine polymer can have the following values of a, b, c, and d: a is 15 to 80 mole percent, b is 1 to 20 mole percent, c is 1 to 65 mole percent and d is 1 to 25 mole percent; a is 15 to 75 mole percent, b is 1 to 15 mole percent, c is 5 to 60 mole percent and d is 10 to 20 mole percent; a is 35 to 85 mole percent, b is 5 to 15 mole percent, c is 5 to 30 mole percent and d is 5 to 20 mole percent; a is 30 to 95 mole percent, b is 1 to 20 mole percent, and either c is 1 to 65 mole percent and d is 0 mole percent or c is 0 mole percent and d is 1 to 25 mole percent; a is 35 to 90 mole percent, b is 1 to 15 mole percent, c is 1 to 65 mole percent and d is 0 mole percent; a is 70 to 95 mole percent, b is 1 to 20 mole percent, c is 0 mole percent and d is 1 to 25 mole percent; a is 35 to 90 mole percent, b is 1 to 15 mole percent, c is 1 to 65 mole percent and d is 0 mole percent; a is 70 to 95 mole percent, b is 1 to 20 mole percent, c is 0 mole percent and d is 1 to 25 mole percent; a is 80 to 99 mole percent, b is 1 to 20 mole percent, and c and d are 0 mole percent; a is 85 to 99 mole percent, b is 1 to 15 mole percent, and c and d are 0 mole percent; a is 85 to 99 mole percent, b is 1 to 15 mole percent, and c and d are 0 mole percent.

The crosslinked amine polymer can also comprise a reaction product of a polymerization mixture comprising a monomer of Formula 2

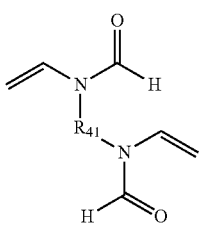
(2)

wherein $R_{41}$ is $C_8$ to $C_{12}$ alkylene or $C_8$ to $C_{12}$ alkylene wherein one or more of the —$CH_2$— groups of the alkylene group is replaced with an amide, a carbonyl, an ether, an ester, a cycloalkyl, an aryl, or a heterocyclo functional group.

The crosslinked amine polymer can also comprise a reaction product of a polymerization mixture comprising a monomer of Formula 3

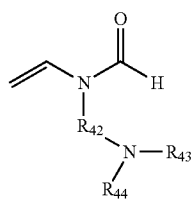
(3)

wherein $R_{42}$ is $C_3$ to $C_{12}$ alkylene or $C_3$ to $C_{12}$ alkylene wherein one or more of the —$CH_2$— groups of the alkylene group is replaced with an amide, a carbonyl, an ether, an ester, a cycloalkyl, an aryl, or a heterocyclo functional group; $R_{43}$ is hydrogen or a protecting group; and $R_{44}$ is a protecting group.

The crosslinked amine polymer can also comprise a reaction product of a polymerization mixture comprising a monomer of Formula 4 and 1 to 25 mole percent of a monomer of Formula 2 based on the total monomers added to the polymerization mixture, the monomers having the formula:

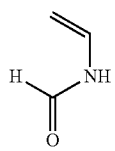
(4)

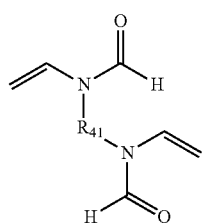
(2)

wherein $R_{41}$ is $C_5$ to $C_{12}$ alkylene or $C_5$ to $C_{12}$ alkylene wherein one or more of the —$CH_2$— groups of the alkylene group is replaced with an amide, a carbonyl, an ether, an ester, a cycloalkyl, an aryl, or a heterocyclo functional group.

For the crosslinked amine polymer being a reaction product of a polymerization mixture comprising Formulae 2 and 4, the polymerization mixture can further comprise from 1 to 65 mole percent of a monomer of Formula 3

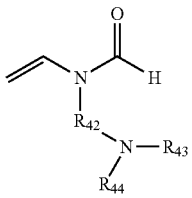

(3)

wherein $R_{42}$ is $C_3$ to $C_{12}$ alkylene or $C_3$ to $C_{12}$ alkylene wherein one or more of the —$CH_2$— groups of the alkylene group is replaced with an amide, a carbonyl, an ether, an ester, a cycloalkyl, an aryl, or a heterocyclo functional group; $R_{43}$ is hydrogen or a protecting group; and $R_{44}$ is a protecting group.

The crosslinked amine polymers polymerization mixture further comprises from 1 to 25 mole percent of a monomer of Formula 5

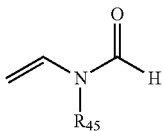

(5)

wherein $R_{45}$ is $C_3$ to $C_{12}$ alkyl, aralkyl or $C_3$ to $C_{12}$ alkyl wherein one or more of the —$CH_2$— groups of the alkyl group is replaced with an amide, a carbonyl, an ether, an ester, a cycloalkyl, an aryl, or a heterocyclo functional group.

The amine polymers can be prepared from a polymerization mixture comprising the following: 15 to 80 mole percent of the monomer 4, 1 to 20 mole percent of the monomer 2, 0 to 65 mole percent of the monomer 3 and 0 to 25 mole percent of the monomer 5; 15 to 80 mole percent of the monomer 4, 1 to 20 mole percent of the monomer 2, 1 to 65 mole percent of the monomer 3 and 1 to 25 mole percent of the monomer 5; 15 to 75 mole percent of the monomer 4, 1 to 15 mole percent of the monomer 2, 5 to 60 mole percent of the monomer 3 and 10 to 20 mole percent of the monomer 5; 15 to 75 mole percent of the monomer 4, 1 to 15 mole percent of the monomer 2, 5 to 60 mole percent of the monomer 3 and 10 to 20 mole percent of the monomer 5; 30 to 95 mole percent of the monomer 4, 1 to 20 mole percent of the monomer 2, and either 1 to 65 mole percent of the monomer 3 and 0 mole percent of the monomer 5 or 0 mole percent of the monomer 3 and 1 to 25 mole percent of the monomer 5; 35 to 90 mole percent of the monomer 4, 1 to 15 mole percent of the monomer 2, and 1 to 65 mole percent of the monomer 3; 70 to 95 mole percent of the monomer 4, 1 to 20 mole percent of the monomer 2, and 1 to 25 mole percent of the monomer 5; 35 to 90 mole percent of the monomer 4, 1 to 15 mole percent of the monomer 2, and 1 to 65 mole percent of the monomer 3; 70 to 95 mole percent of the monomer 4, 1 to 20 mole percent of the monomer 2, and 1 to 25 mole percent of the monomer 5; 80 to 99 mole percent of the monomer 4, and 1 to 20 mole percent of the monomer 2; 85 to 99 mole percent of the monomer 4, and 1 to 15 mole percent of the monomer 2; 85 to 99 mole percent of the monomer 4, and 1 to 15 mole percent of the monomer 2.

Another crosslinked amine polymer can comprise a reaction product of a polymerization mixture comprising a monomer of Formula 4 and a monomer of Formula 2

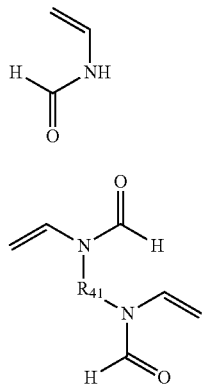

(4)

(2)

wherein $R_{41}$ is $C_3$ to $C_{16}$ alkylene or $C_3$ to $C_{16}$ alkylene wherein one or more of the —$CH_2$— groups of the alkylene group is replaced with an amide, a carbonyl, an ether, an ester, a cycloalkyl, an aryl, or a heterocyclo functional group; wherein a portion of the nitrogen atoms of the crosslinked amine polymer are substituted with a ligand selected from aminoalkyl, aryl, arylalkyl, cycloalkyl, (cycloalkyl)alkyl, heterocyclo, heterocycloalkyl, (trialkylammonio)alkyl, 2-(protected amino)-m-(heterocyclo)-1-oxo$C_m$ alkyl, 2-(protected amino)-1-oxo$C_m$alkyl, 2-(protected amino)-3-methyl-1-oxo$C_m$alkyl, 2-(protected amino)-4-methyl-1-oxo$C_m$alkyl, 2-(protected amino)-1-oxo-m-aryl$C_m$ alkyl, 2-(protected amino)-m-(alkylthio)-1-oxo$C_m$alkyl, 2-(protected amino)-m-(aryl)-1-oxo$C_m$alkyl, 2-(protected amino)-m-carboxy-1-oxo$C_m$alkyl, 2-(protected amino)-m-guanidino-1-oxo$C_m$alkyl, 2-(protected amino)-(m-1)-hydroxy-1-oxo$C_m$alkyl, 2-(protected amino)-m-hydroxy-1-oxo$C_m$alkyl, 2-(protected amino)-m-mercapto-1-oxo$C_m$alkyl, m-(alkylamino)-m-oxo$C_m$alkyl, m-(alkylheterocyclo)$C_m$alkyl, m-amino-2-(protected amino)-1-oxo$C_m$alkyl, m-amino-2-(protected amino)-1,m-dioxo$C_m$alkyl, m-(x-amino$C_x$alkyl)heterocyclo$C_m$alkyl, (m-1)-amino-m-(heterocyclo)-1-oxo$C_m$alkyl, m-(arylalkylamino)-m-oxo$C_m$alkyl, m-(x-(alkylthio)$C_x$alkylamino)-m-oxo$C_m$alkyl, m-(x-amino$C_x$alkylamino)-m-oxo$C_m$alkyl, m-(x-amino-x-oxo$C_x$alkylamino)-m-oxo$C_m$alkyl, m-(x-carboxy$C_x$alkylamino)-m-oxo$C_m$alkyl, m-(heterocycloalkylamino)-m-oxo$C_m$alkyl, m-(x-hydroxy$C_x$alkylamino)-m-oxo$C_m$alkyl, m-((x-1)-hydroxy$C_x$alkylamino)-m-oxo$C_m$alkyl, m-(x-mercapto$C_x$alkylamino)-m-oxo$C_m$alkyl, m-(x-trialkylammonio$C_x$alkyl)heterocyclo$C_m$alkyl, m-(x-(2-(alkoxy)benzamido)$C_x$alkylamino)-m-oxo$C_m$alkyl, m-(x-(3-(alkoxy)benzamido)$C_x$alkylamino)-m-oxo$C_m$alkyl, m-(x-(4-(alkoxy)benzamido)$C_x$alkylamino)-m-oxo$C_m$alkyl, a ligand of formula 6

$$*—R_{46}—R_{47}—R_{48} \quad (6)$$

or a combination thereof, wherein $R_{46}$ is $C_6$ to $C_{16}$ alkylene, $R_{47}$ is 1,y-bis(1-methylpiperidin-4-yl)$C_z$alkylene, $R_{48}$ is $C_6$ to $C_{16}$ alkyl, m is an integer from 3 to 12, x is an integer from 1 to 12, y is an integer from 1 to 14, and z is an integer from 1 to 16.

Another crosslinked amine polymer comprises repeat units derived from reaction of a vinyl amine repeat unit and a crosslinking agent, wherein the vinyl amine repeat unit has the formula:

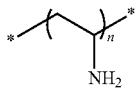

(7)

and the crosslinking agent is X—$R_1$—X or epihalohydrin wherein $R_1$ is $C_3$ to $C_{16}$ alkylene or $C_3$ to $C_{16}$ alkylene wherein one or more of the —$CH_2$— groups of the alkylene group is replaced with an amide, a carbonyl, an ether, an ester, a cycloalkyl, an aryl, or a heterocyclo functional group, each X is independently a leaving group, and a portion of the nitrogen atoms of the crosslinked amine polymer are substituted with a ligand selected from aminoalkyl, aryl, arylalkyl, cycloalkyl, (cycloalkyl)alkyl, heterocyclo, heterocycloalkyl, (trialkylammonio)alkyl, 2-(protected amino)-m-(heterocyclo)-1-oxo$C_m$alkyl, 2-(protected amino)-1-oxo$C_m$alkyl, 2-(protected amino)-3-methyl-1-oxo$C_m$alkyl, 2-(protected amino)-4-methyl-1-oxo$C_m$alkyl, 2-(protected amino)-1-oxo-m-aryl$C_m$alkyl, 2-(protected amino)-m-(alkylthio)-1-oxo$C_m$alkyl, 2-(protected amino)-m-(aryl)-1-oxo$C_m$alkyl, 2-(protected amino)-m-carboxy-1-oxo$C_m$alkyl, 2-(protected amino)-m-guanidino-1-oxo$C_m$alkyl, 2-(protected amino)-(m-1)-hydroxy-1-oxo$C_m$alkyl, 2-(protected amino)-m-hydroxy-1-oxo$C_m$alkyl, 2-(protected amino)-m-mercapto-1-oxo$C_m$alkyl, m-(alkylamino)-m-oxo$C_m$alkyl, m-(alkylheterocyclo)$C_m$alkyl, m-amino-2-(protected amino)-1-oxo$C_m$alkyl, m-amino-2-(protected amino)-1,m-dioxo$C_m$alkyl, m-(x-amino$C_x$alkyl)heterocyclo$C_m$alkyl, (m-1)-amino-m-(heterocyclo)-1-oxo$C_m$alkyl, m-(arylalkylamino)-m-oxo$C_m$alkyl, m-(x-(alkylthio)$C_x$-alkylamino)-m-oxo$C_m$alkyl, m-(x-amino$C_x$alkylamino)-m-oxo$C_m$alkyl, m-(x-amino-x-oxo$C_x$alkylamino)-m-oxo$C_m$alkyl, m-(x-carboxy$C_x$alkylamino)-m-oxo$C_m$alkyl, m-(heterocycloalkylamino)-m-oxo$C_m$alkyl, m-(x-hydroxy-$C_x$alkylamino)-m-oxo$C_m$alkyl, m-((x-1)-hydroxy$C_x$alkylamino)-m-oxo$C_m$alkyl, m-(x-mercapto$C_x$alkylamino)-m-oxo$C_m$alkyl, m-(x-trialkylammonio$C_x$alkyl)heterocyclo$C_m$alkyl, m-(x-(2-(alkoxy)benzamido)$C_x$alkylamino)-m-oxo$C_m$alkyl, m-(x-(3-(alkoxy)benzamido)$C_x$alkylamino)-m-oxo$C_m$alkyl, m-(x-(4-(alkoxy)benzamido)$C_x$alkylamino)-m-oxo$C_m$alkyl, a ligand of formula 6

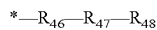

(6)

or a combination thereof, wherein $R_{46}$ is $C_6$ to $C_{16}$ alkylene, $R_{47}$ is 1,y-bis(1-methylpiperidin-4-yl)$C_y$alkylene, $R_{48}$ is $C_6$ to $C_{16}$ alkyl, m is an integer from 3 to 12, x is an integer from 1 to 12, y is an integer from 1 to 14, and z is an integer from 1 to 16.

A crosslinked acrylamide polymer can comprise a reaction product of a polymerization mixture comprising monomers, the polymer having the general structure of formula 9:

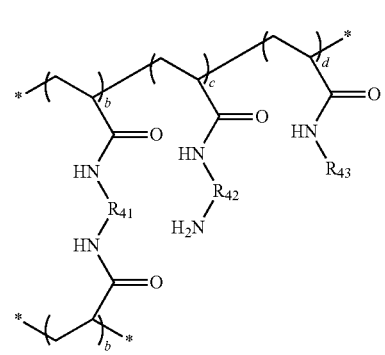

(9)

wherein $R_{41}$ is $C_5$ to $C_{12}$ alkylene or $C_5$ to $C_{12}$ alkylene wherein one or more of the —$CH_2$— groups of the alkylene group is replaced with an amide, a carbonyl, an ether, an ester, a cycloalkyl, an aryl, or a heterocyclo functional group; $R_{42}$ is $C_3$ to $C_{12}$ alkylene or $C_3$ to $C_{12}$ alkylene wherein one or more of the —$CH_2$— groups of the alkylene group is replaced with an amide, a carbonyl, an ether, an ester, a cycloalkyl, an aryl, or a heterocyclo functional group; $R_{43}$ is $C_3$ to $C_{12}$ alkyl, aralkyl or $C_3$ to $C_{20}$ alkyl wherein one or more of the —$CH_2$— groups of the alkyl group is replaced with an amide, a carbonyl, an ether, an ester, a cycloalkyl, an aryl, or a heterocyclo functional group; b is 1 to 25 mole percent based on the ratio of monomers added to the polymerization mixture; and each of c and d is independently 0 to 99 mole percent based on the ratio of monomers added to the polymerization mixture.

Another crosslinked acrylamide polymer comprises a reaction product of a polymerization mixture comprising a monomer of Formula 10 and 1 to 25 mole percent of a monomer of Formula 11 based on the total monomers added to the polymerization mixture, the monomers having the formula:

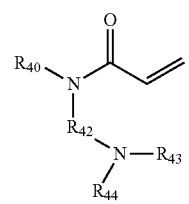

(10)

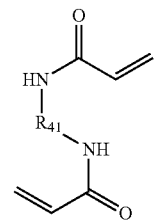

(11)

wherein $R_{40}$ is hydrogen or —$R_{42}NR_{43}R_{44}$; $R_{41}$ is $C_5$ to $C_{12}$ alkylene or $C_5$ to $C_{12}$ alkylene wherein one or more of the —$CH_2$— groups of the alkylene group is replaced with an amide, a carbonyl, an ether, an ester, a cycloalkyl, an aryl, or a heterocyclo functional group; $R_{42}$ is $C_2$ to $C_{12}$ alkylene or $C_2$ to $C_{12}$ alkylene wherein one or more of the —$CH_2$— groups of the alkylene group is replaced with an amide, a carbonyl, an ether, an ester, a cycloalkyl, an aryl, or a heterocyclo functional group; $R_{43}$ is hydrogen or a protecting group; and $R_{44}$ is a protecting group.

The amine polymer can comprise repeat units of polyallylamine and a crosslinking unit of —$R_{50}$— derived from reaction of a crosslinking agent and the polyallylamine, the polyallylamine of formula 14 having the formula:

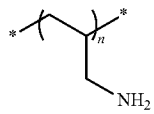
(14)

wherein n is an integer; and $R_{50}$ is $C_8$ to $C_{50}$ alkylene wherein one or more of the —$CH_2$— groups of the alkylene group is replaced with an amide, an ether, an ester, a cycloalkyl, or a heterocyclo functional group.

Another crosslinked amine polymer comprises repeat units derived from reaction of an allyl amine repeat unit and a crosslinking agent, wherein the allyl amine repeat unit has the formula:

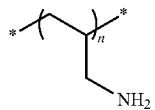
(14)

wherein n is an integer, and the crosslinking agent is X—$R_1$—X or epihalohydrin wherein $R_1$ is independently $C_2$ to $C_{50}$ alkylene or $C_2$ to $C_{50}$ alkylene wherein one or more of the —$CH_2$— groups of the alkylene group is replaced with an amide, a carbonyl, an ether, an ester, a cycloalkyl, an aryl, or a heterocyclo functional group, each X is independently a leaving group, and a portion of the nitrogen atoms of the crosslinked amine polymer are substituted with a ligand selected from aminoalkyl, aryl, arylalkyl, cycloalkyl, (cycloalkyl)alkyl, heterocyclo, heterocycloalkyl, (trialkylammonio)alkyl, 2-(protected amino)-m-(heterocyclo)-1-oxo$C_m$alkyl, 2-(protected amino)-1-oxo$C_m$alkyl, 2-(protected amino)-3-methyl-1-oxo$C_m$alkyl, 2-(protected amino)-4-methyl-1-oxo$C_m$alkyl, 2-(protected amino)-1-oxo-m-aryl$C_m$alkyl, 2-(protected amino)-m-(alkylthio)-1-oxo$C_m$alkyl, 2-(protected amino)-m-(aryl)-1-oxo$C_m$alkyl, 2-(protected amino)-m-carboxy-1-oxo$C_m$alkyl, 2-(protected amino)-m-guanidino-1-oxo$C_m$alkyl, 2-(protected amino)-(m-1)-hydroxy-1-oxo$C_m$alkyl, 2-(protected amino)-m-hydroxy-1-oxo$C_m$alkyl, 2-(protected amino)-m-mercapto-1-oxo$C_m$alkyl, m-(alkylamino)-m-oxo$C_m$alkyl, m-(alkylheterocyclo)$C_m$alkyl, m-amino-2-(protected amino)-1-oxo$C_m$alkyl, m-amino-2-(protected amino)-1,m-dioxo$C_m$alkyl, m-(x-amino$C_x$alkyl)heterocyclo$C_m$alkyl, (m-1)-amino-m-(heterocyclo)-1-oxo$C_m$alkyl, m-(arylalkylamino)-m-oxo$C_m$alkyl, m-(x-(alkylthio)$C_x$alkylamino)-m-oxo$C_m$alkyl, m-(x-amino$C_x$alkylamino)-m-oxo$C_m$alkyl, m-(x-amino-x-oxo$C_x$alkylamino)-m-oxo$C_m$alkyl, m-(x-carboxy$C_x$alkylamino)-m-oxo$C_m$alkyl, m-(heterocycloalkylamino)-m-oxo$C_m$alkyl, m-(x-hydroxy$C_x$alkylamino)-m-oxo$C_m$alkyl, m-((x-1)-hydroxy$C_x$alkylamino)-m-oxo$C_m$alkyl, m-(x-mercapto$C_x$alkylamino)-m-oxo$C_m$alkyl, m-(x-trialkylammonio$C_x$alkyl)heterocyclo$C_m$alkyl, m-(x-(2-(alkoxy)benzamido)$C_x$alkylamino)-m-oxo$C_m$alkyl, m-(x-(3-(alkoxy)benzamido)$C_x$alkylamino)-m-oxo$C_m$alkyl, m-(x-(4-(alkoxy)benzamido)$C_x$alkylamino)-m-oxo$C_m$alkyl, a ligand of formula 6

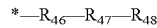
(6)

or a combination thereof, wherein $R_{46}$ is $C_6$ to $C_{16}$ alkylene, $R_{47}$ is 1,y-bis(1-methylpiperidin-4-yl)$C_y$alkylene, $R_{48}$ is $C_6$ to $C_{16}$ alkyl, m is an integer from 3 to 12, x is an integer from 1 to 12, y is an integer from 1 to 14, and z is an integer from 1 to 16.

Another crosslinked amine polymer comprises repeat units of polyethyleneimine and a crosslinking agent, wherein the polyethyleneimine has the formula:

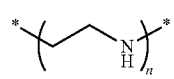
(15)

wherein n is an integer, and the crosslinking agent is X—$R_1$—X or epihalohydrin wherein $R_1$ is independently $C_2$ to $C_{50}$ alkylene or $C_2$ to $C_{50}$ alkylene wherein one or more of the —$CH_2$— groups of the alkylene group is replaced with an amide, a carbonyl, an ether, an ester, a cycloalkyl, an aryl, or a heterocyclo functional group, each X is independently a leaving group, and a portion of the nitrogen atoms of the crosslinked amine polymer are substituted with a ligand selected from aminoalkyl, aryl, arylalkyl, cycloalkyl, (cycloalkyl)alkyl, heterocyclo, heterocycloalkyl, (trialkylammonio)alkyl, 2-(protected amino)-m-(heterocyclo)-1-oxo$C_m$alkyl, 2-(protected amino)-1-oxo$C_m$alkyl, 2-(protected amino)-3-methyl-1-oxo$C_m$alkyl, 2-(protected amino)-4-methyl-1-oxo$C_m$alkyl, 2-(protected amino)-1-oxo-m-aryl$C_m$alkyl, 2-(protected amino)-m-(alkylthio)-1-oxo$C_m$alkyl, 2-(protected amino)-m-(aryl)-1-oxo$C_m$alkyl, 2-(protected amino)-m-carboxy-1-oxo$C_m$alkyl, 2-(protected amino)-m-guanidino-1-oxo$C_m$alkyl, 2-(protected amino)-(m-1)-hydroxy-1-oxo$C_m$alkyl, 2-(protected amino)-m-hydroxy-1-oxo$C_m$alkyl, 2-(protected amino)-m-mercapto-1-oxo$C_m$alkyl, m-(alkylamino)-m-oxo$C_m$alkyl, m-(alkylheterocyclo)$C_m$alkyl, m-amino-2-(protected amino)-1-oxo$C_m$alkyl, m-amino-2-(protected amino)-1,m-dioxo$C_m$alkyl, m-(x-amino$C_x$alkyl)heterocyclo$C_m$alkyl, (m-1)-amino-m-(heterocyclo)-1-oxo$C_m$alkyl, m-(arylalkylamino)-m-oxo$C_m$alkyl, m-(x-(alkylthio)$C_x$alkylamino)-m-oxo$C_m$alkyl, m-(x-amino$C_x$alkylamino)-m-oxo$C_m$alkyl, m-(x-amino-x-oxo$C_x$alkylamino)-m-oxo$C_m$alkyl, m-(x-carboxy$C_x$alkylamino)-m-oxo$C_m$alkyl, m-(heterocycloalkylamino)-m-oxo$C_m$alkyl, m-(x-hydroxy$C_x$alkylamino)-m-oxo$C_m$alkyl, m-((x-1)-hydroxy$C_x$alkylamino)-m-oxo$C_m$alkyl, m-(x-mercapto$C_x$alkylamino)-m-oxo$C_m$alkyl, m-(x-trialkylammonio$C_x$alkyl)heterocyclo$C_m$alkyl, m-(x-(2-(alkoxy)benzamido)$C_x$alkylamino)-m-oxo$C_m$alkyl, m-(x-(3-(alkoxy)benzamido)$C_x$alkylamino)-m-oxo$C_m$alkyl, m-(x-(4-(alkoxy)benzamido)$C_x$alkylamino)-m-oxo$C_m$alkyl, a ligand of formula 6

(6)

or a combination thereof, wherein $R_{46}$ is $C_6$ to $C_{16}$ alkylene, $R_{47}$ is 1,y-bis(1-methylpiperidin-4-yl)$C_y$alkylene, $R_{48}$ is $C_6$ to $C_{16}$ alkyl, m is an integer from 3 to 12, x is an integer from 1 to 12, y is an integer from 1 to 14, and z is an integer from 1 to 16.

Another crosslinked amine polymer comprises the reaction product of a branched polyethyleneimine and a crosslinking agent, wherein the crosslinking agent is X—$R_1$—X wherein $R_1$ is independently $C_8$ to $C_{50}$ alkylene or $C_8$ to $C_{50}$ alkylene wherein one or more of the —CH₂— groups of the alkylene group is replaced with an amide, a carbonyl, an ether, an ester, a cycloalkyl, an aryl, or a heterocyclo functional group, and each X is independently a leaving group. Suitable branched polyethyleneimine is commercially available from BASF SE at a variety of molecular weights as Lupasol® or Lupamin® and from Polysciences, Inc. (Warrington, Pa.).

In preferred embodiments, X is halo, epoxy, diaziridino, mesylate, sulfate, phosphate, aldehyde, ketone, or a combination thereof. Leaving groups are well known and can be selected from those known in the art, such as those in Larock, Comprehensive Organic Transformations (VCH 1989), e.g., p. 397 et seq. In some of the embodiments, $R_1$ is $C_{10}$ to $C_{14}$ alkylene, particularly $C_{10}$ to $C_{12}$ alkylene, and more particularly decylene.

Ligands

The polymers described herein can also have a portion of the nitrogen atoms of the amine polymer substituted with a ligand of alkyl, aminoalkyl, aryl, arylalkyl, oxoalkyl, cycloalkyl, (cycloalkyl)alkyl, guanidino, heterocyclo, heterocycloalkyl, (trialkylammonio)alkyl, 2-(protected amino)-m-(heterocyclo)-1-oxoC$_m$alkyl, 2-(protected amino)-1-oxoC$_m$alkyl, 2-(protected amino)-3-methyl-1-oxoC$_m$alkyl, 2-(protected amino)-4-methyl-1-oxoC$_m$alkyl, 2-(protected amino)-1-oxo-m-arylC$_m$alkyl, 2-(protected amino)-m-(alkylthio)-1-oxoC$_m$alkyl, 2-(protected amino)-m-(aryl)-1-oxoC$_m$alkyl, 2-(protected amino)-m-carboxy-1-oxoC$_m$alkyl, 2-(protected amino)-m-guanidino-1-oxoC$_m$alkyl, 2-(protected amino)-(m-1)-hydroxy-1-oxoC$_m$alkyl, 2-(protected amino)-m-hydroxy-1-oxoC$_m$alkyl, 2-(protected amino)-m-mercapto-1-oxoC$_m$alkyl, m-(alkylamino)-m-oxoC$_m$alkyl, m-(alkylheterocyclo)C$_m$alkyl, m-amino-2-(protected amino)-1-oxoC$_m$alkyl, m-amino-2-(protected amino)-1,m-dioxoC$_m$alkyl, m-(x-aminoC$_x$alkyl)heterocycloC$_m$alkyl, (m-1)-amino-m-(heterocyclo)-1-oxoC$_m$alkyl, m-(arylalkylamino)-m-oxoC$_m$alkyl, m-(x-(alkylthio)C$_x$alkylamino)-m-oxoC$_m$alkyl, m-(x-aminoC$_x$alkylamino)-m-oxoC$_m$alkyl, m-(x-amino-x-oxoC$_x$alkylamino)-m-oxoC$_m$alkyl, m-(x-carboxyC$_x$alkylamino)-m-oxoC$_m$alkyl, m-(heterocycloalkylamino)-m-oxoC$_m$alkyl, m-(x-hydroxyC$_x$alkylamino)-m-oxoC$_m$alkyl, m-((x-1)-hydroxyC$_x$alkylamino)-m-oxoC$_m$alkyl, m-(x-mercaptoC$_x$alkylamino)-m-oxoC$_m$alkyl, m-(x-trialkylammonioC$_x$alkyl)heterocycloC$_m$alkyl, m-(x-(2-(alkoxy)benzamido)C$_x$alkylamino)-m-oxoC$_m$alkyl, m-(x-(3-(alkoxy)benzamido)C$_x$alkylamino)-m-oxoC$_m$alkyl, m-(x-(4-(alkoxy)benzamido)C$_x$alkylamino)-m-oxoC$_m$alkyl, a ligand of formula 4

$$*—R_{46}—R_{47}—R_{48} \quad (4)$$

or a combination thereof, wherein $R_{46}$ is $C_6$ to $C_{16}$ alkylene, $R_{47}$ is 1,y-bis(1-methylpiperidin-4-yl)C$_y$alkylene, $R_{48}$ is $C_6$ to $C_{16}$ alkyl, m is an integer from 3 to 12, x is an integer from 1 to 12, y is an integer from 1 to 14, and z is an integer from 1 to 16.

In some embodiments, the ligand is arylalkyl selected from naphthalen-2-ylalkyl or naphthalen-1-ylalkyl; heterocycloalkyl selected from m-(1-methylpyrrolidinium-1-yl)C$_m$alkyl, m-(2-(1H-indol-3-yl)ethylamino)-m-oxoC$_m$alkyl, m-(2-methylthiazol-3-ium-3-yl)C$_m$alkyl, m-(benzo[d]thiazol-3-ium-3-yl)C$_m$alkyl, m-(pyridinium-1-yl)Cmalkyl, m-(tetrahydro-1H-thiophenium-1-yl)C$_m$alkyl, z-(1,2-dialkyl-1H-imidazol-3-ium-3-yl)C$_z$alkyl, m-(2,3-dialkyl-1H-imidazol-3-ium-1-yl)C$_m$alkyl, z-(1-alkyl-1H-imidazol-3-ium-3-yl)C$_z$alkyl, m-(3-alkyl-1H-imidazol-3-ium-1-yl) C$_m$alkyl, or z-(thiazol-3-ium-3-yl)C$_z$alkyl; 2-(protected amino)-m-(heterocyclo)-1-oxoC$_m$alkyl selected from 2-(protected amino)-m-(1H-indol-3-yl)-1-oxoC$_m$-alkyl or 2-(protected amino)-m-(1H-imidazol-4-yl)-1-oxoC$_m$alkyl; 2-(protected amino)-1-oxo-m-phenylC$_m$alkyl; 2-(protected amino)-m-(hydroxyphenyl)-1-oxoC$_m$alkyl; m-(alkylheterocyclo)C$_m$alkyl selected from m-(3-alkyl-1H-imidazol-3-ium-1-yl)C$_m$alkyl, m-(1-alkyl-1H-imidazol-3-ium-3-yl) C$_m$alkyl, m-(1-alkyl-2-methyl-1H-imidazol-3-ium-3-yl) C$_m$alkyl, or m-(3-alkyl-2-methyl-1H-imidazol-3-ium-1-yl) C$_m$alkyl; m-(x-aminoC$_x$alkyl)heterocycloC$_m$alkyl selected from m-(3-(x-aminoC$_x$alkyl)-1H-imidazol-3-ium-1-yl) C$_m$alkyl or m-(1-(x-aminoC$_x$alkyl)-1H-imidazol-3-ium-3-yl) C$_m$alkyl(m-1)-amino-m-(1H-indol-2-yl)-1-oxoC$_m$alkyl; m-(arylalkylamino)-m-oxoC$_m$alkyl selected from m-(hydroxyphenalkylamino)-m-oxoC$_m$alkyl or m-(phenalkylamino)-m-oxo-C$_m$alkyl; m-(x-(heterocyclo)C$_x$alkyl)heterocycloC$_m$alkyl selected from m-(1-(x-(1-methyl-1H-imidazol-3-ium-3-yl)C$_x$alkyl)-1H-imidazol-3-ium-3-yl) C$_m$alkyl, m-(1-(x-(3-methyl-1H-imidazol-3-ium-1-yl)C$_x$-alkyl)-1H-imidazol-3-ium-3-yl) C$_m$alkyl, m-(3-(x-(1-methyl-1H-imidazol-3-ium-3-yl)C$_x$alkyl)-1H-imidazol-3-ium-1-yl) C$_m$alkyl, or m-(3-(x-(3-methyl-1H-imidazol-3-ium-1-yl)C$_x$alkyl)-1H-imidazol-3-ium-1-yl) C$_m$alkyl; m-(x-(1H-imidazol-4-yl)C$_x$alkylamino)-m-oxoC$_m$alkyl; or m-(x-trialkylammonioC$_x$alkyl)heterocycloC$_m$alkyl selected from m-(3-(x-trialkylammonio)C$_x$alkyl)-1H-imidazol-3-ium-1-yl)C$_m$alkyl or m-(1-(x-trialkylammonio)C$_x$alkyl)-1H-imidazol-3-ium-3-yl)C$_m$alkyl wherein m is an integer from 3 to 12, x is an integer from 1 to 12, and z is an integer from 1 to 16.

In some instances, the ligand is derived from an amino acid. Such ligands include, but are not limited to, 2-(protected amino)-m-(heterocyclo)-1-oxoC$_m$alkyl, m-amino-2-(protected amino)-1,m-dioxoC$_m$alkyl, m-amino-2-(protected amino)-1-oxoC$_m$alkyl, 2-(protected amino)-1-oxoC$_m$alkyl, 2-(protected amino)-m-(alkylthio)-1-oxoC$_m$alkyl, 2-(protected amino)-m-(hydroxyphenyl)-1-oxoC$_m$alkyl, 2-(protected amino)-1-oxo-m-phenylC$_m$alkyl, 2-(protected amino)-m-(1H-imidazol-4-yl)-1-oxoC$_m$alkyl, 2-(protected amino)-m-carboxy-1-oxoC$_m$alkyl, 2-(protected amino)-3-methyl-1-oxoC$_m$alkyl, 2-(protected amino)-4-methyl-1-oxoC$_m$alkyl, 2-(protected amino)-m-mercapto-1-oxoC$_m$alkyl, 2-(protected amino)-(m-1)-hydroxy-1-oxoC$_m$alkyl, 2-(protected amino)-m-hydroxy-1-oxoC$_m$alkyl, 2-(protected amino)-m-guanidino-1-oxoC$_m$alkyl, m-(x-(alkylthio)C$_x$alkylamino)-m-oxoC$_m$alkyl, m-(hydroxyphenalkylamino)-m-oxoC$_m$alkyl, m-oxo-m-(phenalkylamino) C$_m$alkyl, m-(x-(1H-imidazol-4-yl)C$_x$alkylamino)-m-oxoC$_m$alkyl, m-(x-carboxyC$_x$alkylamino)-m-oxoC$_m$alkyl, m-(alkylamino)-m-oxoC$_m$alkyl, m-(x-mercaptoC$_x$alkylamino)-m-oxoC$_m$alkyl, m-((x-1)-hydroxyC$_x$alkylamino)-m-oxoC$_m$alkyl, m-(x-hydroxyC$_x$alkylamino)-m-oxoC$_m$alkyl, m-(x-aminoC$_x$alkylamino)-m-oxoC$_m$alkyl, or m-(x-amino-x-oxoC$_x$alkylamino)-m-oxoC$_m$alkyl, wherein m is an integer from 3 to 12, and x is an integer from 1 to 12.

Some of the polymers described herein have a portion of the nitrogen atoms of the amine polymer substituted with a ligand of 2-(tert-butoxycarbonylamino)-3-(1H-indol-3-yl)-1-oxopropyl, 5-(2-(4-(nonyloxy)benzamido)ethylamino)-5-oxopentyl, (4,5-dihydro-1H-imidazolyl, 10-(pyridinium-1-yl)decyl, 2-(1H-indol-3-yl)ethyl, 5-(2-(1H-indol-3-yl)ethylamino)-5-oxopentyl, 2-amino-3-(1H-indol-2-yl)-1-oxopropyl, 3-(1,2-dimethyl-1H-imidazol-3-ium-3-yl)propyl, 10-(1,2-dimethyl-1H-imidazol-3-ium-3-yl)decyl, 10-(1-methyl-1H-imidazol-3-ium-3-yl)decyl, 3-(thiazol-3-ium-3-yl)propyl, 3-aminopropyl, 3-cyclohexylpropyl, 3-phenylpropyl, 3-(trimethylammonio)propyl, 3-(1-methylpyrrolidinium-1-yl)propyl, 3-(2-methylthiazol-3-ium-3-yl)

propyl, 3-(benzo[d]thiazol-3-ium-3-yl)propyl, 3-(tetrahydro-1H-thiophenium-1-yl)propyl, 3-(3-methyl-1H-imidazol-3-ium-1-yl)propyl, 3-(1-methyl-1H-imidazol-3-ium-3-yl)propyl, 3-(3-(3-aminopropyl)-1H-imidazol-3-ium-1-yl)propyl, 3-(1-(3-aminopropyl)-1H-imidazol-3-ium-3-yl) propyl, 3-(3-(5-trimethylammonio)pentyl)-1H-imidazol-3-ium-1-yl)propyl, 3-(1-(5-trimethylammonio)pentyl)-1H-imidazol-3-ium-3-yl)propyl, 3-(3-decyl-1H-imidazol-3-ium-1-yl)propyl, 3-(1-decyl-1H-imidazol-3-ium-3-yl) propyl, 3-(3-(9-(3-methyl-1H-imidazol-3-ium-1-yl)nonyl)-1H-imidazol-3-ium-1-yl)propyl, 3-(1-(9-(1-methyl-1H-imidazol-3-ium-3-yl)nonyl)-1H-imidazol-3-ium-3-yl) propyl, 3-(1-(9-(3-methyl-1H-imidazol-3-ium-1-yl)nonyl)-1H-imidazol-3-ium-3-yl)propyl, 3-(3-(9-(1-methyl-1H-imidazol-3-ium-3-yl)nonyl)-1H-imidazol-3-ium-1-yl) propyl, 4-(3-decyl-1H-imidazol-3-ium-1-yl)butyl, 4-(1-decyl-1H-imidazol-3-ium-3-yl)butyl, 10-(1-decyl-2-methyl-1H-imidazol-3-ium-3-yl)decyl, 10-(3-decyl-2-methyl-1H-imidazol-3-ium-1-yl)decyl, 3-(1,2-dimethyl-1H-imidazol-3-ium-3-yl)propyl, 3-(2,3-dimethyl-1H-imidazol-3-ium-1-yl) propyl, 10-(2,3-dimethyl-1H-imidazol-3-ium-1-yl)decyl, 10-(1,2-dimethyl-1H-imidazol-3-ium-3-yl)decyl, 10-(1-methyl-1H-imidazol-3-ium-3-yl)decyl, 10-(3-methyl-1H-imidazol-3-ium-1-yl)decyl, 10-(1-butyl-1H-imidazol-3-ium-3-yl)decyl, 10-(3-butyl-1H-imidazol-3-ium-1-yl)decyl, 10-(pyridinium-1-yl)decyl, 10-(1-methylpyrrolidinium-1-yl)decyl, naphthalen-2-ylmethyl, naphthalen-1-ylmethyl, 4-amino-2-(tert-butoxycarbonylamino)-1,4-dioxobutyl, 2-(tert-butoxycarbonylamino)-1-oxoethyl, 2-(tert-butoxycarbonylamino)-4-(methylthio)-1-oxobutyl, 5-(3-(methylthio)propylamino)-5-oxopentyl, 2-(tert-butoxycarbonylamino)-3-(4-hydroxyphenyl)-1-oxopropyl, 5-(4-hydroxyphenethylamino)-5-oxopentyl, 2-(tert-butoxycarbonylamino)-1-oxo-3-phenylpropyl, 5-oxo-5-(phenethylamino)pentyl, 2-(tert-butoxycarbonylamino)-3-(1H-imidazol-4-yl)-1-oxopropyl, 5-(2-(1H-imidazol-4-yl) ethylamino)-5-oxopentyl, 2-(tert-butoxycarbonylamino)-3-carboxy-1-oxopropyl, 5-(2-carboxyethylamino)-5-oxopentyl, 2-(tert-butoxycarbonylamino)-3-methyl-1-oxobutyl, 5-(isobutylamino)-5-oxopentyl,(3R)-2-(tert-butoxycarbonylamino)-3-methyl-1-oxopentyl,(R)-5-(2-methylbutylamino)-5-oxopentyl, 2-(tert-butoxycarbonylamino)-3-mercapto-1-oxopropyl, 5-(2-mercaptoethylamino)-5-oxopentyl,(3R)-2-(tert-butoxycarbonylamino)-3-hydroxy-1-oxobutyl,(R)-5-(2-hydroxypropylamino)-5-oxopentyl, 6-amino-2-(tert-butoxycarbonylamino)-1-oxohexyl, 5-(5-aminopentylamino)-5-oxopentyl, 5-amino-2-(tert-butoxycarbonylamino)-1,5-dioxopentyl, 5-(4-amino-4-oxobutylamino)-5-oxopentyl, 2-(tert-butoxycarbonylamino)-5-guanidino-1-oxopentyl, 5-(4-guanidinobutylamino)-5-oxopentyl, 2-(tert-butoxycarbonylamino)-3-hydroxy-1-oxopropyl, 5-(2-hydroxyethylamino)-5-oxopentyl, 2-(tert-butoxycarbonylamino)-4-methyl-1-oxopentyl, 5-(isopentylamino)-5-oxopentyl, 2-(tert-butoxycarbonylamino)-4-carboxy-1-oxobutyl, 5-(3-carboxypropylamino)-5-oxopentyl, 2-(tert-butoxycarbonylamino)-1-oxopropyl, 5-(ethylamino)-5-oxopentyl, a ligand of formula 4

*—$R_{46}$—$R_{47}$—$R_{48}$ (4)

or a combination thereof, wherein $R_{46}$ is decylene, $R_{47}$ is 1,3-bis(1-methylpiperidin-4-yl)propane, and $R_{48}$ is decyl.

Some of the amine polymers described herein have a portion of the nitrogen atoms of the amine polymer substituted with a ligand of 2-(tert-butoxycarbonylamino)-3-(1H-indol-3-yl)-1-oxopropyl, 5-(2-(4-(nonyloxy)benzamido)ethylamino)-5-oxopentyl, (4,5-dihydro-1H-imidazolyl, 10-(pyridinium-1-yl)decyl, 2-(1H-indol-3-yl)ethyl, 5-(2-(1H-indol-3-yl)ethylamino)-5-oxopentyl, 2-amino-3-(1H-indol-2-yl)-1-oxopropyl, 3-(1,2-dimethyl-1H-imidazol-3-ium-3-yl)propyl, 10-(1,2-dimethyl-1H-imidazol-3-ium-3-yl)decyl, 10-(1-methyl-1H-imidazol-3-ium-3-yl)decyl, 3-(thiazol-3-ium-3-yl)propyl, 3-aminopropyl, 3-cyclohexylpropyl, 3-phenylpropyl, 3-(trimethylammonio)propyl, 3-(1-methylpyrrolidinium-1-yl)propyl, 3-(2-methylthiazol-3-ium-3-yl) propyl, 3-(benzo[d]thiazol-3-ium-3-yl)propyl, 3-(tetrahydro-1H-thiophenium-1-yl)propyl, 3-(3-methyl-1H-imidazol-3-ium-1-yl)propyl, 3-(1-methyl-1H-imidazol-3-ium-3-yl)propyl, 3-(3-(3-aminopropyl)-1H-imidazol-3-ium-1-yl)propyl, 3-(1-(3-aminopropyl)-1H-imidazol-3-ium-3-yl) propyl, 3-(3-(5-trimethylammonio)pentyl)-1H-imidazol-3-ium-1-yl)propyl, 3-(1-(5-trimethylammonio)pentyl)-1H-imidazol-3-ium-3-yl)propyl, 3-(3-decyl-1H-imidazol-3-ium-1-yl)propyl, 3-(1-decyl-1H-imidazol-3-ium-3-yl) propyl, 3-(3-(9-(3-methyl-1H-imidazol-3-ium-1-yl)nonyl)-1H-imidazol-3-ium-1-yl)propyl, 3-(1-(9-(1-methyl-1H-imidazol-3-ium-3-yl)nonyl)-1H-imidazol-3-ium-3-yl) propyl, 3-(1-(9-(3-methyl-1H-imidazol-3-ium-1-yl)nonyl)-1H-imidazol-3-ium-3-yl)propyl, 3-(3-(9-(1-methyl-1H-imidazol-3-ium-3-yl)nonyl)-1H-imidazol-3-ium-1-yl) propyl, 4-(3-decyl-1H-imidazol-3-ium-1-yl)butyl, 4-(1-decyl-1H-imidazol-3-ium-3-yl)butyl, 10-(1-decyl-2-methyl-1H-imidazol-3-ium-3-yl)decyl, 10-(3-decyl-2-methyl-1H-imidazol-3-ium-1-yl)decyl, 3-(1,2-dimethyl-1H-imidazol-3-ium-3-yl)propyl, 3-(2,3-dimethyl-1H-imidazol-3-ium-1-yl) propyl, 10-(2,3-dimethyl-1H-imidazol-3-ium-1-yl)decyl, 10-(1,2-dimethyl-1H-imidazol-3-ium-3-yl)decyl, 10-(1-methyl-1H-imidazol-3-ium-3-yl)decyl, 10-(3-methyl-1H-imidazol-3-ium-1-yl)decyl, 10-(1-butyl-1H-imidazol-3-ium-3-yl)decyl, 10-(3-butyl-1H-imidazol-3-ium-1-yl)decyl, 10-(pyridinium-1-yl)decyl, 10-(1-methylpyrrolidinium-1-yl)decyl, naphthalen-2-ylmethyl, naphthalen-1-ylmethyl, a ligand of formula 4

*—$R_{46}$—$R_{47}$—$R_{48}$ (4)

or a combination thereof, wherein $R_{46}$ is decylene, $R_{47}$ is 1,3-bis(1-methylpiperidin-4-yl)propane, and $R_{48}$ is decyl.

In the above ligands having protected amino groups, the protecting group is independently —C(O)O$R_{49}$, —C(O)$R_{50}$, or $R_{43}$ and $R_{44}$ together with the attached nitrogen atom form a succinimide or phthalimide ring, wherein $R_{49}$ is alkyl or aryl, and $R_{50}$ is amino, hydrogen, alkyl, or haloalkyl.

The polymers having a portion of the nitrogen atoms of the polymer substituted with a ligand can have about 5 mole % to about 60 mole % ligand based on the moles of amine or amide monomer, about 5 mole % to about 50 mole % ligand based on the moles of amine or amide monomer, or about 10 mole % to about 30 mole % ligand based on the moles of amine or amide monomer.

Polymer Preparation Processes

Poly(vinylamine) polymers were prepared by contacting N-vinylformamide, a crosslinker, and a polymerization initiator in a polar aprotic solvent. After the vinylformamide and crosslinking monomer are contacted, the reaction mixture is heated to from about 40° C. to about 80° C. or about 60° C. for about 12 to 24 hours. After the reaction is complete, the polymer product is washed with an aqueous acidic solution, followed by a basic solution and then lyophilized until dry.

Poly(vinylamine) polymers modified with hydrophobic ligands were prepared by contacting N-vinylformamide, a crosslinker, a polymerization initiator, and a hydrophobic ligand in a polar aprotic solvent. After the vinylformamide and crosslinking monomer are contacted, the reaction mixture is heated to from about 40° C. to about 80° C. or about 60° C. for about 12 to 24 hours. After the reaction is complete, the polymer product is washed with an aqueous acidic solution, followed by a basic solution and then lyophilized until dry.

The polymers of the invention have various chemical, structural and physical properties that contribute to their capacity for binding bile acids and/or their affinity for binding bile acids preferentially over fatty acids, phosphates and/or other compounds present in the gastrointestinal tract.

The polymer can be administered in the form of a salt, or as a partial salt, or as salt free base. The "salt" has nitrogen atoms or groups in all or some of the repeat units that are protonated to create a positively charged nitrogen atom associated with a negatively charged counterion. The anionic counterions can be selected to minimize adverse effects on the patient. Examples of suitable counterions include $Cl^-$, $Br^-$, $CH_3OSO_3^-$, $HSO_4^-$, $SO_4^{2-}$, nitrate, $HCO_3^-$, $CO_3^{2-}$, acetate, lactate, phosphate, hydrophosphate, fumarate, malate, pyruvate, malonate, benzoate, glucuronate, oxalate, acetylglycinate, succinate, propionate, butyrate, ascorbate, citrate, tartrate, maleate, folate, an amino acid derivative, a nucleotide, a lipid, a phospholipid, or a combination thereof. The counterions can be the same as, or different from, each other. For example, the reaction product can contain two different types of counterions. In most cases, not all of the nitrogen atoms will be in a salt form, with the percent of nitrogen atoms in a salt form being dictated by certain properties, such as flowability, storage time, and weight.

To determine the in vitro binding affinity for bile salts under conditions that are intended to mimic in certain respects those conditions found in the lower small intestine, the polymer is analyzed using assay A. The A assay combines the polymer to be analyzed in a desired concentration with a solution that mimics certain conditions present in the lower small intestine as described in Protocol 1 in the examples. After a period of time, the polymers are recovered by centrifugation and the supernatants are sampled, filtered to remove any remaining particulates and assayed for ion concentrations by liquid chromatography (LC). By comparing the equilibrium concentrations of glycocholate ($GC_{eq}$), glycodeoxycholate ($GDC_{eq}$), oleyl glycerol ($OG_{eq}$) and/or oleic acid ($OA_{eq}$) in the presence of the polymer to their concentrations in test solution in the absence of the polymer, the amount of each component bound under these experimental conditions in mmoles/g polymer is calculated. The in vitro bile salt binding affinity under the conditions of the A assay in Protocol 1 results in a maximum of about 0.75 mmol/gram polymer. Thus, the in vitro bile salt binding affinity for the polymers of this invention is from about 0.15 to about 0.75 mmol/gram polymer, particularly from about 0.3 to about 0.75 mmol/gram polymer, and more particularly, from about 0.46 to about 0.75 mmol/gram polymer when measured in the Assay A solution. Further, in some embodiments, the in vitro bile salt binding affinity for the amine polymers of this invention is greater than 0.55 mmol/gram polymer, greater than 0.60 mmol/gram polymer, or greater than 0.65 mmol/gram polymer.

In some cases the concentration of phosphate ions was also determined on a strong anion exchange column by liquid chromatography using a basic mobile phase in order to measure the phosphate binding affinity. The polymers of the invention bind phosphate in vitro in an amount of less than 0.2 mmol/gram of polymer, particularly up to about 0.15 mmol/gram polymer, and more particularly, up to about 0.10 mmol/gram polymer when measured using an A assay.

To determine the in vitro binding capacity for bile salts under conditions that are intended to mimic in certain respects those conditions found in the upper small intestine after a meal, the polymer is analyzed using Assay B. In Assay B, the polymer to be analyzed is combined in a desired concentration with a solution that mimics certain conditions present in the upper small intestine as described in Protocol 2 in the examples. The same general procedure as described above was used to calculate the amount of each component bound. The in vitro bile salt binding capacity under the conditions of the B assay in Protocol 2 results in a maximum of about 3.7 mmol/gram polymer. Thus, the in vitro bile salt binding capacity for the polymers is from about 0.64 to about 3.7 mmol/gram polymer, particularly from about 1.3 to about 3.7 mmol/gram polymer, and more particularly from about 2.22 to about 3.7 mmol/gram polymer when measured in the assay B solution.

To determine the in vivo binding retention for bile salts, the polymer is analyzed in a hamster model. The hamster model provides a complex and relevant measure of the polymer's binding capacity for bile acids, its binding affinity for bile acids over other anions, and its ability to retain bound bile acids and to increase the excretion of bile acids and bile acids metabolites from the gastrointestinal tract into the feces. Preferably, Golden Syrian hamsters may be used as they have a similar bile acid profile to that of humans. Male Golden Syrian hamsters are acclimated and then placed on a high-fat, high-sucrose western diet, D12079B (Research Diet, New Brunswick, N.J.) for several days before the study is started. The polymers to be analyzed are blended into western diet at the desired dose to prepare the test diets. The hamsters are held in individual metabolic cages allowing the separation and collection of feces. Animals from the test groups are switched to the test diets, while animals from the untreated group are kept on western diet without added polymer. Food intake is measured for four consecutive days. For each hamster, feces from the last three days of the treatment period are collected, pooled, lyophilized, and then homogenized by grinding in a mortar and pestle. The feces samples are then extracted for fecal bile salt analysis. In some cases, a baseline treatment period is conducted where all groups of animals are placed in metabolic cages as described above and fed only on western diet without added test article. Feces are collected as described above and the effect of the polymer on bile salt fecal excretion is determined by comparing baseline versus treatment periods. Otherwise, the effect of polymers on bile salt fecal excretion is determined by comparing untreated versus test groups. Hamster fecal bile salts are analyzed as described in the examples. The polymers can have a calculated in vivo binding capacity at least 25%, 50%, 75%, 100%, 125%, 150%, 175% or 200% greater than colesevelam hydrochloride when measured at a dosage of 0.5% of the total feed intake in male Golden Syrian hamsters fed a Western diet.

The polymers can have a calculated in vivo bile salt binding capacity of at least about 0.35 mmol bile salt/gram of polymer when measured in humans. The polymers can have an in vivo binding capacity in a human of at least 0.35 mmol bile salt per gram of polymer, at least 0.4 mmol bile salt per gram of polymer, at least 0.5 mmol bile salt per gram of polymer, at least 0.6 mmol bile salt per gram of polymer, or more.

Polymers of the invention are crosslinked materials, meaning that they do not generally dissolve in solvents however they can swell with solvents or absorb the solvent. As used herein, "swelling ratio" refers to the number of grams of solvent taken up by one gram of crosslinked polymer when equilibrated in an aqueous environment. The swelling ratio is sensitive to the polymer solvent interaction parameter as described in Flory Huggins (Flory P. J. "Principles of Polymer Chemistry, Cornell Ithica Pub. 1953). When more than one measurement of swelling is taken for a given polymer, the mean of the measurements is taken to be the swelling ratio. The swelling ratio in water, or in physiological isotonic buffer, which is representative of the gastrointestinal tract (for example United States Pharmacopeia Simulated Intestinal Fluid or Simulated Gastric Fluid), is typically in the range of about 1 to about 10 g of swelling solution (solvent)/g of polymer, particularly about 2 to 6, and more particularly about 2 to about 4. The counterion content of the polymer can affect the swelling ratio, in the examples listed below, a chloride counterion is used, and the chloride content is stated. The counterion content can be as much as 25 wt % of the total weight of the polymer and as little as <1% of the total weight of the polymer.

The polymers can be particles having a mean diameter from about 10 microns to about 200 microns. In some of the embodiments, the polymer particles are substantially spherical beads. These beads can have a mean diameter from about 10 microns to about 200 microns. As used herein, the term "substantially" means generally rounded particles having an average aspect ratio of about 1.0 to about 2.0. Aspect ratio is the ratio of the largest linear dimension of a particle to the smallest linear dimension of the particle. Aspect ratios may be easily determined by those of ordinary skill in the art. This definition includes spherical particles, which by definition have an aspect ratio of 1.0. In some embodiments, the particles have an average aspect ratio of about 1.0, 1.2, 1.4, 1.6, 1.8 or 2.0. The particles may be round or elliptical when observed at a magnification wherein the field of view is at least twice the diameter of the particle.

The substantially spherical beads can be prepared using methods known to a person skilled in the art. For example, a preferred mode of synthesis is a heterogeneous process. Such processes are also referred to as polymerization in dispersed media and include direct or inverse suspension, emulsion, precipitation, dispersion or micro emulsion polymerization, reaction in aerosol or using bulk polymerization methods. In inverse suspension, the continuous phase can be selected from apolar solvents such as silicone, toluene, benzene, hydrocarbon solvents or oils, halogenated solvents, supercritical carbon dioxide, and the like. The discrete phase for the inverse suspension system comprises solubilizing the monomer and crosslinker in water; this can be achieved by the addition of an acid such as hydrochloric acid to form the amine salt, which renders the organic amine substantially more water soluble and dispersing the amine solution in a water-immiscible solvent to form an emulsion. With a direct suspension or emulsion process, water can be used as the continuous phase, although salt brines are also useful to "salt out" the monomer and crosslinker into the discrete phase, as described in U.S. Pat. No. 5,414,068. The monomers can be dispersed either neat or as a solution in the continuous phase using a cosolvent. The crosslinking monomer can be added to the reaction in a semicontinuous fashion (staged addition) allowing the polymerization reaction to occur. Isolation of the beads can be carried out by filtration, washing and drying. Size can be further controlled or modified by reduction processes such as extrusion and grinding.

Polymers can be obtained by methods known to those in the art, examples of which are illustrated in the Examples herein. The crosslinked polymer particle is generally a reaction product of a reaction mixture that is subjected to reaction conditions. The reaction mixture may also generally contain components that are not chemically incorporated into the product. The reaction mixture typically comprises monomers. The polymer may be further modified by reaction with a hydrolysis agent.

In general, the reactions are conducted such that a polymer network is generated, which is insoluble but can be solvated into a gel. When the interpenetrating solvent is water, the insoluble material is described as a hydrogel. The reaction is carried either in solution, in bulk (i.e. using the neat monomers and crosslinking compounds) or in dispersed media. The reaction may start with the introduction of for example, temperature change or irradiation. In general polymers can be prepared by chain growth or step growth. Step growth polymerization involves the polymerization of monomers that contain unsaturated functional groups, including radical polymerization, cationic polymerization and anionic polymerization. Polyvinylamine (starting monomer is polyvinylformamide) and polyallylamine are prepared via radical polymerization. Step growth polymerization involves the reaction of bifunctional or polyfunctional monomers that grow via, dimers, trimers to longer oligomers. Network formation occurs when the polymer chains react with each other. Parameters that effect the network formation reaction include temperature, solvent choice, the concentrations of monomers and crosslinkers, and the ratio of the monomer to the crosslinking monomer. The addition of a base maybe desired in some cases.

The polymer particles have a mean diameter of from about 10 μm to about 200 μm. Specific ranges are where the polymer particles have a mean diameter of from about 20 μm to about 200 μm, from about 20 μm to about 150 μm, or from about 20 μm to about 125 μm. Other ranges include from about 35 μm to about 150 μm, from about 35 μm to about 125 μm, from about 50 μm to about 125 μm, or from about 50 μm to about 100 μm. Particle sizes, including mean diameters, distributions, etc. can be determined using techniques known to those of skill in the art. For example, U.S. Pharmacopeia (USP)<429> discloses methods for determining particle sizes.

Various polymer particles also have less than about 4 volume percent of the particles that have a diameter of less than about 10 μm; particularly, less than about 2 volume percent of the particles that have a diameter of less than about 10 μm; more particularly, less than about 1 volume percent of the particles that have a diameter of less than about 10 μm; and even more particularly, less than about 0.5 volume percent of the particles that have a diameter of less than about 10 μm. In other cases, specific ranges are less than about 4 volume percent of the particles that have a diameter of less than about 20 μm; less than about 2 volume percent of the particles that have a diameter of less than about 20 μm; less than about 1 volume percent of the particles that have a diameter of less than about 20 μm; less than about 0.5 volume percent of the particles that have a diameter of less than about 20 μm; less than about 2 volume percent of the particles that have a diameter of less than about 30 μm; less than about 1 volume percent of the particles that have a diameter of less than about 30 μm; less than about 1 volume percent of the particles that have a diameter of less than about 30 μm; less than about 1 volume percent of the particles that have a diameter of less than about 40 μm; or less than about 0.5 volume percent of the particles that have a diameter of less than about 40 μm. In various embodiments, the polymer has a particle size distribution wherein not more than about 5 volume % of the particles have a diameter less than about 30 μm (i.e., D(0.05)<30 μm), not more than about 5 volume % of the particles have a diameter greater than about 250 μm (i.e., D(0.05)>250 μm), and at least about 50 volume % of the particles have a diameter in the range from about 70 to about 150 μm.

The particle distribution of the polymer can be described as the span. The span of the particle distribution is defined as (D(0.9)−D(0.1))/D(0.5), where D(0.9) is the value wherein 90% of the particles have a diameter below that value, D(0.1) is the value wherein 10% of the particles have a diameter below that value, and D(0.5) is the value wherein 50% of the particles have a diameter above that value and 50% of the particles have a diameter below that value as measured by laser diffraction. The span of the particle distribution is typically from about 0.5 to about 1, from about 0.5 to about 0.95, from about 0.5 to about 0.90, or from about 0.5 to about 0.85. Particle size distributions can be measured using Niro Method No. A 8 d (revised September 2005), available from GEA Niro, Denmark, using the Malvern Mastersizer.

It has now been found that when using the polymers and the compositions of the present invention, a once-a-day dose is substantially equivalent to a twice-a-day dose, which is also substantially equivalent to a three-times-a-day dose. Generally, the once per day or twice per day administration of a daily amount of the polymer or the composition has a bile acid removal that is not statistically significantly different from the removal of the same polymer or composition at the same daily amount administered three times per day.

Additionally, the invention is directed to methods of removing bile acids from an animal subject by administering an polymer or a pharmaceutical composition comprising a polymer, wherein less than 25% of subjects taking the polymer or composition once per day experience mild or moderate gastrointestinal adverse events at a dose of 6.0 grams/day or less. Gastrointestinal adverse events may include flatulence, diarrhea, abdominal pain, constipation, stomatitis, nausea and/or vomiting. In some aspects, the polymer or composition is administered twice a day and less than 25% of subjects taking the polymer or composition twice per day experience mild or moderate gastrointestinal adverse events. In some instances, the subjects taking the polymer or composition once per day or twice per day experience no severe gastrointestinal adverse events. The polymers or pharmaceutical compositions of the present invention have about 50% or more tolerability as compared to the same polymer or composition of the same daily amount administered three times a day. For example, for every two patients in which administration of the polymer three times a day is well tolerated, there is at least one patient in which administration of the polymer once a day or twice a day is well tolerated.

When administration is well tolerated, there should be little or no significant dose modification or dose discontinuation by the subject. In some embodiments, well tolerated means there is no apparent dose response relationship for gastrointestinal adverse events. In some of these embodiments, well tolerated means that the following gastrointestinal adverse effects are not reported from a statistically significant number of subjects, including those effects selected from the group consisting of flatulence, diarrhea, abdominal pain, constipation, stomatitis, nausea and vomiting.

In other embodiments, the present invention provides a method of removing bile acids from the gastrointestinal tract of an animal subject in need thereof, comprising administering an effective amount of a polymer or a composition comprising the polymer, wherein the polymer or composition is as well tolerated as administering substantially the same amount of the same polymer or composition three times per day. In some instances, the subject is experiencing hypercholesteremia and thus the method treats hypercholesteremia. In other instances, the method lowers serum cholesterol.

Without wanting to be bound by any particular theory, the tolerability of the polymer or composition comprising the polymers results from physical properties that the polymers may possess, including a viscosity when hydrated and sedimented of from about 10,000 Pa·s to about 2,500,000 Pa·s, from about 10,000 Pa·s to about 2,000,000 Pa·s, from about 10,000 Pa·s to about 1,500,000 Pa·s, from about 10,000 Pa·s to about 1,000,000 Pa·s, from about 10,000 Pa·s to about 500,000 Pa·s, or from about 10,000 Pa·s to about 250,000 Pa·s, from about 30,000 Pa·s to about 3,000,000 Pa·s, from about 30,000 Pa·s to about 2,000,000 Pa·s, or from about 30,000 Pa·s to about 1,000,000 Pa·s, the viscosity being measured at a shear rate of 0.01 $\sec^{-1}$. This viscosity is measured using a wet polymer prepared by mixing the polymer thoroughly with a slight excess of simulated intestinal fluid (per USP <26>), allowing the mixture to sediment for 3 days at 37° C., and decanting free liquid from the sedimented wet polymer. The steady state shear viscosity of this wet polymer can be determined using a Bohlin VOR Rheometer (available from Malvern Instruments Ltd., Malvern, U.K.) or equivalent with a parallel plate geometry (upper plate of 15 mm diameter and lower plate of 30 mm diameter, and gap between plates of 1 mm) and the temperature maintained at 37° C.

The polymers may further have a hydrated and sedimented yield stress of from about 150 Pa to about 4000 Pa, from about 150 Pa to about 3000 Pa, from about 150 Pa to about 2500 Pa, from about 150 Pa to about 1500 Pa, from about 150 Pa to about 1000 Pa, from about 150 Pa to about 750 Pa, or from about 150 Pa to about 500 Pa, from about 200 Pa to about 4000 Pa, from about 200 Pa to about 2500 Pa, from about 200 Pa to about 1000 Pa, or from about 200 Pa to about 750 Pa. Dynamic stress sweep measurements (i.e., yield stress) can be made using a Reologica STRESSTECH Rheometer (available from Reologica Instruments AB, Lund, Sweden) or equivalent in a manner known to those of skill in the art. This rheometer also has a parallel plate geometry (upper plate of 15 mm diameter, lower plate of 30 mm diameter, and gap between plates of 1 mm) and the temperature is maintained at 37° C. A constant frequency of 1 Hz with two integration periods can be used while the shear stress is increased from 1 to $10^4$ Pa.

Polymers used in this invention may also have desirable compressibility and bulk density when in the form of a dry powder. Some of the particles of the polymers in the dry form have a bulk density of from about 0.8 $g/cm^3$ to about 1.5 $g/cm^3$, from about 0.82 $g/cm^3$ to about 1.5 $g/cm^3$, from about 0.84 $g/cm^3$ to about 1.5 $g/cm^3$, from about 0.86 $g/cm^3$ to about 1.5 $g/cm^3$, from about 0.8 $g/cm^3$ to about 1.2 $g/cm^3$, or from about 0.86 $g/cm^3$ to about 1.2 $g/cm^3$. The bulk density affects the volume of polymer needed for administration to a patient. For example, a higher bulk density means that a lower volume will provide the same number of grams of polymer. This lower volume can improve patient compliance by allowing the patient to perceive they are taking a smaller amount due to the smaller volume.

A powder composed of the particles of the polymer in dry form has a compressibility index of from about 3 to about 30, from about 3 to about 25, from about 3 to about 20, from about 3 to about 15, from about 3 to about 13, from about 5 to about 25, from about 5 to about 20, or from about 5 to about 15. The compressibility index is defined as 100*(TD−BD)/TD, wherein BD and TD are the bulk density and tap density, respectively. Bulk density (BD) and tapped density (TD) are used to calculate a compressibility index (CI). Standardized procedures for this measurement are specified as USP <616>. A quantity of the powder is weighed into a graduated cylinder. The mass M and initial (loosely packed) volume Vo are recorded. The cylinder is then placed on an apparatus which raises and then drops the cylinder, from a height of 3 mm±10%, at a rate of 250 times (taps) per minute. The volume is measured after 500 taps and then again after an additional 750 taps (1250 total). If the difference in volumes after 500 and 1250 taps is less than 2%, then the final volume is recorded as Vf and the experiment is complete. Otherwise, tapping is repeated in increments of 1250 taps at a time, until the volume change before and after tapping is less than 2%. The following quantities are calculated from the data:

Bulk Density (BD)=$M/Vo$

Tapped Density (TD)=$M/Vf$

Compressibility Index (CI, also called Can's Index)
=100*(TD−BD)/TD.

The powder form of the polymers settles into its smallest volume more easily than polymers conventionally used to treat hypercholesteremia. This makes the difference between the bulk density and the tap density (measured powder density after tapping a set number of times) from about 3% to about 30%, from about 3% to about 25%, from about 3% to about 20%, from about 3% to about 15%, from about 3% to about 10%, from about 5% to about 35%, from about 5% to about 30%, or from about 5% to about 20% of the bulk density.

The polymers and pharmaceutical compositions described herein retain a significant amount of the bound bile salts throughout the small intestine, and specifically, the bile salts bound by the polymer are not released prior to entry into the colon or excretion of the polymer in the feces. The term "significant amount" as used herein is not intended to mean that the entire amount of the bound bile salt are retained prior to fecal excretion or entry in to the colon. A sufficient amount of the bound bile salts are retained, such that a therapeutic and/or prophylactic benefit is obtained. For example, it may be sufficient for a polymer to retain bile acids such that there is a significant increase in the amount of bile acids entering the colon. The bile acids may then be released from the polymer but may still substantially be excreted either intact or as metabolites in the feces and thus for purposes of this invention have been sufficiently retained. Retention of bile acids may be measured by measuring the amounts of bile acids in the feces or in colonic aspirates or extracts above baseline levels (i.e., above the amount of bile acids retained in the feces when no polymer is administered to the animal subject). Particular amounts of bound bile salts that can be retained range from about 5% to about 100% above baseline levels. The polymer or pharmaceutical composition should retain at least about 5% of the bound bile salts, more particularly at least about 10%, even more particularly at least about 25% and most particularly at least about 50% of the bound bile salts above baseline levels.

Retention of bile acids by the polymer can be calculated either directly by in vitro methods or indirectly by in vivo methods. The period of retention is generally during the time that the polymer or composition is being used therapeutically or prophylactically. When the polymer or composition is used to bind and remove bile salts from the gastrointestinal tract, the retention period is the time of residence of the polymer or composition in the gastrointestinal or the average residence time of the polymer or composition in the small intestine.

The polymers and pharmaceutical compositions described herein may result in an increased ratio of primary to secondary bile acids excreted in the feces. Bile acids may be characterized by their site of synthesis and modification; primary bile acids (for example cholic acid and chenodeoxycholic acid) are synthesized in hepatocytes from cholesterol and secondary or tertiary bile acids (for example deoxycholic acid and lithocholic acid) are the products of bacterial dehydroxylation in the terminal ileum and colon. Primary bile acids may be deconjugated and/or dehydroxylated to convert them to secondary or tertiary bile acids; for example deoxycholate (from cholate) and lithocholate (from chenodeoxycholate). A change in the ratio of excreted bile acids towards primary or unmetabolized bile acids is a measure of in vivo retention of bile acids by polymers. The polymers, in an in vivo measurement, can produce on average at least 11% primary bile acids in the feces based on total bile acids in the feces.

Generally, the polymers are not significantly absorbed from the gastrointestinal tract. Depending upon the size distribution of the polymer particles, clinically insignificant amounts of the polymers may be absorbed. More specifically, about 90% or more of the polymer is not absorbed, about 95% or more is not absorbed, even more specifically about 97% or more is not absorbed, and most specifically about 98% or more of the polymer is not absorbed.

The polymers can be used to remove bile salts from an animal subject by administering an effective amount of the polymer to an animal subject in need thereof. The bile salts can be bound and retained by the polymer and then removed from the gastrointestinal tract in the feces. Further, the polymers can be used to reduce serum LDL-cholesterol, or serum non-HDL-cholesterol, in an animal subject. In some instances, the mean serum LDL can be decreased by at least 15%, at least 20%, at least 25%, at least 30% or more after 2, 4, 12, 26, 52 or more weeks of treatment with the polymer at a daily dose at which the subject experiences no severe gastrointestinal adverse events. In some instances, the daily dose of the polymer is about 6.0 g/day, 5.0 g/day, 4.0 g/day, 3.0, 2.5, or 2.0 g/day or less.

Further, the polymers can be administered to improve glycemic control in a human subject with Type II diabetes mellitus. Preferably, when a human subject with Type II diabetes mellitus is treated, glycated hemoglobin ($Hb_{A1c}$) can be decreased by at least 0.5%, at least 0.6%, at least 0.7%, at least 0.8%, at least 0.9%, at least 1.0% or more after 18, 26, 52 or more weeks of treatment with the polymer at a daily dose at which the subject experiences no severe gastrointestinal adverse events. In some instances, the daily dose of the polymer is about 6.0 g/day, 5.0 g/day, 4.0 g/day, 3.0, 2.5, or 2.0 g/day or less. Also, the fasting plasma glucose can be decreased by at least 14 mg/dL (0.8 mmol/L), at least 16 mg/dL (0.9 mmol/L), at least 18 mg/dL (1 mmol/L), at least 20 mg/dL (1.1 mmol/L) or more after 2, 4, 12, 26, 52 or more weeks of treatment with the polymer at a daily dose at which the subject experiences no severe gastrointestinal adverse events. In some instances, the daily dose of the polymer is about 6.0 g/day, 5.0 g/day, 4.0 g/day, 3.0, 2.5, or 2.0 g/day or less.

Further, the polymers can be used to ameliorate, treat or slow progression of Alzheimer's disease.

The polymers can also be used to treat non-alcoholic statohepatitis, cholestatic pruritus, irritable bowel syndrome with diarrhea (IBS-D), idiopathic bile acid malabsorption, genetic or congenital Fibroblast Growth Factor 19 (FGF19) deficiency or a combination thereof. When the polymers are used to treat cholestatic pruritus, they can be used in combination with an oral or topical antipruritic containing, for example, an antihistamine, a corticosteroid, a local anesthetic, a counterirritant, an opioid, an opioid receptor antagonist, or other therapies including but not limited to crotamiton, doxepin, mirtazapine, capsaicin, tacrolimus, linoleic acid, gabapentin, activated charcoal, thalidomide, naltrexone, erythropoietin, nicergoline, naltrexone, nalmefene, butorphanol, naloxone, rifampin, ondansetron, ursodeoxycholate, S-adenosyl-L-methionine, serotonin-selective reuptake inhibitors, phenobarbital, dronabinol, phototherapy, or a combination thereof.

When the polymers are used to treat IBS-D, they can be used in combination with antidiarrheals such as opiates, opioid or opioid analogs including loperamide, codeine, diphenoxylate, serotonin receptor antagonists such as alosetron, ramosetron and cilansetron, serotonin-selective reuptake inhibitors, tricyclic antidepressants such as amitriptyline and desipramine or drugs reducing the levels of serotonin (5-HT), antispasmodic drugs including anticholinergics such as hyoscyamine or dicyclomine, chloride secretion blockers such as crofelemer and probiotics.

As used herein, an animal subject can be a human or other mammal in need of either bile salt removal, reduction of serum LDL-cholesterol, or non HDL-cholesterol concentration, increase in HDL-C or improved glycemic control.

The methods, polymers and compositions described herein are suitable for removal of bile salts from an animal subject wherein the subject is in need of such bile salt removal. For example, patients experiencing hypercholesterolemia or hyperlipidemia benefit from such bile salt removal. The methods described herein are applicable to these patients regardless of the underlying condition that is causing the high serum cholesterol levels or need for bile acid removal.

The polymers can be administered once, twice, or three times a day. If the polymer is administered once a day, it may be administered just before, with, or just after the largest meal of the day. Also, if administered once a day, it may be administered in connection with the largest, on average during a twenty-four hour period, release of bile acids from the gall bladder, which is typically in the morning. Further, it is preferred that the polymer is administered at least 3 hours before or after any agents that might have an adverse interaction with the polymers.

The dosage regimen to treat hypercholesterolemia, atherosclerosis, diabetes, Alzheimer's disease, non-alcoholic steatohepatits, cholestatic pruritus, IBS-D, idiopathic bile acid malabsorption or reduce plasma cholesterol with the combination therapy and pharmaceutical compositions of the present invention can be selected using a variety of factors. These include the type, age, weight, sex, diet, and medical condition of the patient, the severity of the disease, the route of administration, pharmacological consideration such as the activity, efficacy, pharmacokinetics and toxicology profiles of the particular compound employed, whether a drug delivery system is utilized, and whether the polymer is administered as part of a drug combination. Thus, the dosage regimen actually employed may vary widely.

Initial treatment of a patient suffering from a hyperlipidemic condition such as hypercholesterolemia and/or atherosclerosis can begin with the dosages indicated above. Treatment should generally be continued as necessary over a period of several weeks to several months or years until the condition has been controlled or eliminated. Patients undergoing treatment with the polymers disclosed herein can be routinely monitored by, for example, measuring serum LDL and total cholesterol levels by any of the methods well known in the art, to determine the effectiveness of the combination therapy. Repeated analysis of such data permits modification of the treatment regimen during therapy so that optimal effective amounts of each type of agent are administered at any point in time, and so that the duration of treatment can be determined as well. In this way, the treatment regimen/dosing schedule can be rationally modified over the course of therapy so that the lowest amount of polymer and optionally, combination treatment, is administered and so that administration is continued only so long as is necessary to successfully treat the hyperlipidemic condition such as hypercholesterolemia and atherosclerosis.

If necessary, the polymers or pharmaceutical compositions may be administered in combination with other therapeutic agents. The choice of therapeutic agents that can be co-administered with the compounds of the invention will depend, in part, on the condition being treated. For example, various agents can be co-administered with the polymer, including agents used in reducing serum LDL-cholesterol or non-HDL-cholesterol, which comprise a hydroxymethylglutaryl-coenzyme A (HMG CoA) reductase inhibitor, a fibrate, a cholesterol absorption inhibitor, niacin (i.e. nicotinic acid or derivatives thereof), a phytosterol, an intestinal lipase inhibitor, an intestinal or secreted phospholipase A2 inhibitor, inhibitors of the synthesis or normal activity of Apo-B100, agonists of the synthesis or normal activity of ApoA, or any agent that modulates cholesterol absorption or metabolism, or a combination thereof. In some instances, the HMG CoA reductase inhibitor comprises a statin, such as atorvastatin, cerivastatin, fluvastatin, lovastatin, mevastatin, pitavastatin, pravastatin, rosuvastatin, simvastatin, or a combination thereof. The cholesterol absorption inhibitor can comprise ezetimibe. The fibrate can be benzafibrate, ciprofibrate, clofibrate, gemfibrozil, fenofibrate, or a combination thereof. The intestinal lipase inhibitor can comprise orlisatat. In some instances, the polymers or pharmaceutical compositions may be administered in combination with a HMG CoA reductase inhibitor and niacin (e.g., lovastatin and niacin), or a HMG CoA reductase inhibitor and a cholesterol absorption inhibitor (e.g., simvastatin and ezetimibe), or a HMG CoA reductase inhibitor and an intestinal lipase inhibitor.

In another example, other agents can be co-administered with the polymer, including agents used in preventing or treating diabetes, obesity or other dyslipidemias, such as a sulfonylurea, a biguanidine, a glitazone, a thiazolidindione, an activator of peroxisome proliferator-activated receptors (PPARs), an alpha-glucosidase inhibitor, a potassium channel antagonist, an aldose reductase inhibitor, a glucagon antagonist, a retinoid X receptor (RXR) antagonist, a farnesoid X receptor (FXR) agonist, a FXR antagonist, glucagon-like peptide-1 (GLP-1), a GLP-1 analog, a dipeptidyl peptidase IV (DPP-IV) inhibitor, amylin, an amylin analog, an SGLT2 inhibitor, insulin, an insulin secretagogue, a thyroid hormone, a thyroid hormone analog, an alpha glucosidase inhibitor or a combination thereof. The biguanidine can be metformin, buformin, phenformin, or a combination thereof. The thiazolidindione can be pioglitazone, rivoglitazone, rosiglitazone, troglitazone, or a combination thereof. The sulfonylurea can be acetohexamide, chlorpropamide, tolbutamide, tolazamide, glipizide, gliclazide, glibenclamide, gliquidone, glyclopyramide, glimepiride, or a combination thereof. The DPP-IV inhibitor can be alogliptin, linagliptin, saxagliptin, sitagliptin, vildagliptin, or a combination thereof. The GLP-1 analog can be exenatide, liraglutide, albiglutide, or a combination thereof. The alpha glucosidase inhibitor can be acarbose, miglitol or voglibose.

The term dyslipidemia is taken to mean a deviation in at least one of total serum cholesterol, LDL-cholesterol, non-HDL cholesterol, HDL-cholesterol or triglyceride from that considered normal by the National Cholesterol Education Program or other suitable bodies. In another example, other agents can be co-administered with the polymer, including an anti-platelet agent, a beta-blocker, a renin-angiotensin-aldosterone system (RAAS) inhibitor, a RAAS modulator (e.g., angiotensin converting enzyme inhibitors, renin inhibitors, angiotensin receptor blockers, aldosterone antagonists or sodium channel blockers, including amiloride, triamterene, trimethoprim, and pentamidine) or a combination thereof.

The polymers can also be administered with other cholesterol-lowering agents such as acifran, azacosterol, benfluorex, β-benzalbutyramide, carnitine, chondroitin sulfate, clomestrone, detaxtran, dextran sulfate sodium, 5,8,11,14, 17-eicosapentaenoic acid, eritadenine, furazabol, meglutol, melinamide, mytatrienediol, ornithine, γ-oryzanol, pantethine, pentaerythritol tetraacetate, α-phenybutyramide, priozadil, probucol, β-sitosterol, sultosilic acid, piperazine salt, tiadenol, triparanol, xenbucin, or a combination thereof.

Other agents that can be advantageously used for treatment in combination with the polymers are a squalene epoxidase inhibitor, a squalene synthetase inhibitor (or squalene synthase inhibitor), an acyl-coenzyme A, cholesterol acyltransferase (ACAT) inhibitor (including selective inhibitors of ACAT-1 or ACAT-2, as well as dual inhibitors of ACAT-1 and ACAT-2), a microsomal triglyceride transfer protein (MTP) inhibitor, probucol, a cholesterol absorption inhibitor (e.g., ezetimibe and 1-(4-fluorophenyl)-3(R)-3(S)-(4-fluorophenyl)-3-hydroxypropyl), 4(S)-4-hydroxyphenol (-2-azetidinone) described in U.S. Pat. Nos. 5,727,115 and 5,846,966), a LDL receptor inducer, a platelet aggregation inhibitor (e.g., a glycoprotein IIb/IIIa fibrinogen receptor antagonist), aspirin, vitamin $B_6$ (or pyridoxine), vitamin $B_{12}$ (or cyanocobalamin), a water-soluble pharmaceutical salt or ester of folic acid (e.g., sodium salt and the methylglucamine salt), an anti-oxidant vitamin (e.g., vitamin C and E and beta-carotene), or a combination thereof.

The term "treating" as used herein includes achieving a therapeutic benefit. By therapeutic benefit is meant eradication, amelioration, or prevention of the underlying disorder being treated. For example, in a hypercholesterolemia patient, therapeutic benefit includes eradication or amelioration of the underlying hypercholesterolemia. Also, a therapeutic benefit is achieved with the eradication, amelioration, or prevention of one or more of the physiological symptoms associated with the underlying disorder such that an improvement is observed in the patient, notwithstanding that the patient may still be afflicted with the underlying disorder. In some treatment regimens, the polymer or composition of the invention may be administered to a patient at risk of developing hypercholesterolemia or diabetes or to a patient reporting one or more of the physiological symptoms of hypercholesterolemia or diabetes, even though a diagnosis of hypercholesterolemia or diabetes may not have been made.

The pharmaceutical compositions of the present invention include compositions wherein the polymers are present in an effective amount, i.e., in an amount effective to achieve therapeutic or prophylactic benefit. The actual amount effective for a particular application will depend on the patient (e.g., age, weight, etc.), the condition being treated, and the route of administration. Determination of an effective amount is well within the capabilities of those skilled in the art, especially in light of the disclosure herein. The effective amount for use in humans can be estimated from animal models. For example, a dose for humans can be formulated to achieve gastrointestinal concentrations that have been found to be effective in animals. In various embodiments, the human patient takes about 0.5 g to about 10 g per day, preferably about 0.5 g to about 5 g per day, more preferably, about 0.5 g to about 3 g per day, about 0.5 g to about 2.5 g per day, and most preferably about 0.5 g to about 2.0 g per day.

The polymers and compositions described herein can be used as food products and/or food additives. They can be added to foods prior to consumption or during packaging.

The polymers or pharmaceutically acceptable salts thereof, or compositions described herein, can be delivered to the patient using a wide variety of routes or modes of administration. The most preferred routes for administration are oral, intestinal, or rectal. Rectal routes of administration are known to those of skill in the art. Intestinal routes of administration generally refer to administration directly into a segment of the gastrointestinal tract, e.g., through a gastrointestinal tube or through a stoma. The most preferred route for administration is oral.

The polymers (or pharmaceutically acceptable salts thereof) may be administered per se or in the form of a pharmaceutical composition wherein the active compound(s) is in admixture or mixture with one or more pharmaceutically acceptable excipients. Pharmaceutical compositions for use in accordance with the present invention may be formulated in a conventional manner using one or more pharmaceutically acceptable excipients comprising carriers, diluents, and auxiliaries which facilitate processing of the active compounds into preparations which can be used physiologically. Proper composition is dependent upon the route of administration chosen.

For oral administration, the polymers or compositions of the invention can be formulated readily by combining the polymer or composition with pharmaceutically acceptable excipients well known in the art. Such excipients enable the compositions of the invention to be formulated as powders, tablets, pills, dragees, capsules, liquids, gels, syrups, slurries, suspensions, wafers, and the like, for oral ingestion by a patient to be treated. Pharmaceutical preparations for oral use can be obtained as a solid excipient, optionally grinding a resulting mixture, and processing the mixture of granules, after adding suitable auxiliaries, if desired, to obtain tablets or dragee cores. Suitable excipients are, in particular, fillers such as sugars, including lactose or sucrose; cellulose preparations such as, for example, maize starch, wheat starch, rice starch, potato starch, gelatin, gum tragacanth, methyl cellulose, hydroxypropyl methylcellulose, sodium carboxymethylcellulose, and/or polyvinyl pyrrolidone (PVP); and various flavoring agents known in the art. If desired, disintegrating agents may be added, such as the cross-linked polyvinyl pyrrolidone, agar, or alginic acid or a salt thereof such as sodium alginate.

Additionally, the polymer composition can comprise one or more fat-soluble vitamins such as vitamin A, D, E, K, or a combination thereof. An amount of the fat-soluble vitamin can be added to the composition sufficient to deliver about the daily dietary intake level (i.e., the Reference Daily Intake (RDI)), which is currently 3000 IU, 400 IU, 30 IU, 80 μg, respectively, for vitamin A, D, E, and K.

In various embodiments, the active ingredient (e.g., polymer) constitutes over about 20%, more particularly over about 50%, even more particularly over about 75%, and most particularly more than about 90% by weight of the oral dosage form, the remainder comprising suitable excipient(s).

The polymers or pharmaceutical compositions can be administered in the form of a chewable or mouth-disintegrating tablet, a liquid, a powder, a powder contained within a sachet, a soft gelatin capsule, or a hard gelatin capsule. In some embodiments, the polymers of the invention are provided as pharmaceutical compositions in the form of liquid compositions. In various embodiments, the pharmaceutical composition contains a polymer dispersed in a suitable liquid excipient. Suitable liquid excipients are known in the art; see, e.g., Remington's Pharmaceutical Sciences.

An effective amount of the polymers of the invention can be administered to the animal subject in less than four unit doses per day, such as in less than four tablets per day. The "dosage unit" or "unit dose" is a tablet, capsule or other oral dosage form containing an amount of the polymer. The polymer is generally administered in 4, 3, 2 or 1 unit doses in a 24-hour period, which provides a daily dose of the polymer to the subject under treatment.

In various preferred embodiments, the polymer is a free-flowing powder.

Unless otherwise indicated, an "alkyl" group as described herein alone or as part of another group is an optionally substituted linear saturated monovalent hydrocarbon radical containing from one to twenty carbon atoms and preferably one to twelve carbon atoms, or an optionally substituted branched saturated monovalent hydrocarbon radical containing three to twenty carbon atoms, and preferably three to eight carbon atoms. Examples of unsubstituted alkyl groups include methyl, ethyl, n-propyl, i-propyl, n-butyl, i-butyl, s-butyl, t-butyl, n-pentyl, i-pentyl, s-pentyl, t-pentyl, and the like.

The term "amide" as used herein represents a bivalent (i.e., difunctional) amido linkage

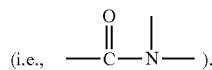

The term "aryl" as used herein alone or as part of another group denotes an optionally substituted monovalent aromatic hydrocarbon radical, preferably a monovalent monocyclic or bicyclic group containing from 6 to 12 carbons in the ring portion, such as phenyl, biphenyl, naphthyl, substituted phenyl, substituted biphenyl or substituted naphthyl. Phenyl and substituted phenyl are the more preferred aryl groups. The term "aryl" also includes heteroaryl.

The term "cycloalkyl" as used herein denotes optionally an optionally substituted cyclic saturated monovalent bridged or non-bridged hydrocarbon radical containing from three to eight carbon atoms in one ring and up to 20 carbon atoms in a multiple ring group. Exemplary unsubstituted cycloalkyl groups include cyclopropyl, cyclobutyl, cyclopentyl, cyclohexyl, cycloheptyl, cyclooctyl, adamantyl, norbornyl, and the like.

The term "-ene" as used as a suffix as part of another group denotes a bivalent radical in which a hydrogen atom is removed from each of two terminal carbons of the group, or if the group is cyclic, from each of two different carbon atoms in the ring. For example, alkylene denotes a bivalent alkyl group such as methylene (—$CH_2$—) or ethylene (—$CH_2CH_2$—), and arylene denotes a bivalent aryl group such as o-phenylene, m-phenylene, or p-phenylene.

The term "ether" as used herein represents a bivalent (i.e., difunctional) ether linkage (i.e., —O—).

The term "ester" as used herein represents a bivalent (i.e., difunctional) ester linkage (i.e., —C(O)O—).

The term "heteroaryl," as used herein alone or as part of another group, denotes an optionally substituted monovalent monocyclic or bicyclic aromatic radical of 5 to 10 ring atoms in protonated or unprotonated form, where one or more, preferably one, two, or three, ring atoms are heteroatoms independently selected from N, O, and S, and the remaining ring atoms are carbon. Exemplary heteroaryl moieties include benzofuranyl, benzo[d]thiazolyl, benzo[d]thiazolium, isoquinolinyl, isoquinolinium, quinolinyl, quinolinium, thiophenyl, imidazolyl, imidazolium, oxazolyl, oxazolium, furanyl, thiazolyl, thiazolium, pyridinyl, pyridinium, furyl, thienyl, pyridyl, pyrrolyl, pyrrolidinium, indolyl, indolinium, and the like.

The term "heterocyclo," as used herein alone or as part of another group, denotes a saturated or unsaturated monovalent monocyclic group of 4 to 8 ring atoms in protonated or unprotonated form, in which one or two ring atoms are heteroatom(s), independently selected from N, O, and S, and the remaining ring atoms are carbon atoms. Additionally, the heterocyclic ring may be fused to a phenyl or heteroaryl ring, provided that the entire heterocyclic ring is not completely aromatic. Exemplary heterocyclo groups include the heteroaryl groups described above, pyrrolidino, pyrrolidinium, piperidino, piperidinium, morpholino, morpholinium, piperazino, piperazinium, and the like.

The term "hydrocarbon" as used herein describes a compound or radical consisting exclusively of the elements carbon and hydrogen.

The term "substituted" as in "substituted aryl," "substituted alkyl," and the like, means that in the group in question (i.e., the alkyl, aryl or other group that follows the term), at least one hydrogen atom bound to a carbon atom is replaced with one or more substituent groups such as hydroxy (—OH), alkylthio, phosphino, amido (—CON($R_A$)($R_B$), wherein $R_A$ and $R_B$ are independently hydrogen, alkyl, or aryl), amino(-N($R_A$)($R_B$), wherein $R_A$ and $R_B$ are independently hydrogen, alkyl, or aryl), halo (fluoro, chloro, bromo, or iodo), silyl, nitro (—$NO_2$), an ether (—$OR_A$ wherein $R_A$ is alkyl or aryl), an ester (—OC(O)$R_A$ wherein $R_A$ is alkyl or aryl), keto (—C(O)$R_A$ wherein $R_A$ is alkyl or aryl), heterocyclo, and the like. When the term "substituted" introduces a list of possible substituted groups, it is intended that the term apply to every member of that group. That is, the phrase "optionally substituted alkyl or aryl" is to be interpreted as "optionally substituted alkyl or optionally substituted aryl."

Having described the invention in detail, it will be apparent that modifications and variations are possible without departing from the scope of the invention defined in the appended claims.

EXAMPLES

Example 1: Preparation of N,N'—(C$_m$alkane-1,m-diyl)bis(N-vinylformamide) crosslinking monomers

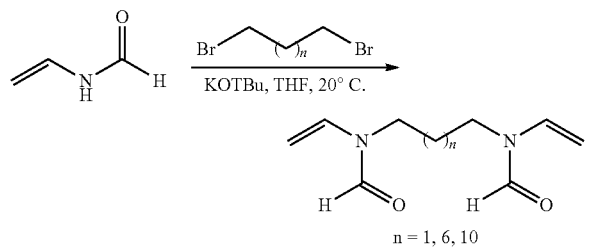

n = 1, 6, 10

A dry 250 ml Schlenk flask was equipped with a magnetic stir bar, dropping funnel, and sealed with a rubber septum. The flask was purged with nitrogen and charged with N-vinylformamide (3.24 g, 45.6 mmol) and anhydrous THF (100 ml). The flask was cooled to 10° C. in an ice bath, and potassium tert-butoxide totaling 5.57 g (45.6 mmol) was added in three separate portions over 45 minutes through the top of the flask under nitrogen flow. 1,8-Dibromooctane (4.00 ml, 21.7 mmol) was added slowly dropwise to the reaction mixture over 30 minutes. After addition, the reaction was allowed to warm up to room temperature and stir overnight. The solvent was removed in vacuo, and diluted with 150 ml of water. The water layer was extracted with diethyl ether (3×100 ml), dried over magnesium sulfate, and concentrated in vacuo. The N,N'-(octane-1,8-diyl)bis(N-vinylformamide) material was further purified by column chromatography over silica (diethyl ether/ethyl acetate, 4:1 v/v). Yield: 40%; $^1$NMR (CDCl$_3$, δ=ppm) δ: 8.29, 8.12 (s, 2H); 7.26-7.14, 6.59-6.51 (m, 2H); 4.62-4.53 (m, 2H); 4.45-4.40 (m, 2H); 3.58-3.52, 3.46-3.42 (t, 4H); 1.62-1.53 (m, 4H); 1.31-1.26 (m, 12H).

N,N'-(propane-1,3-diyl)bis(N-vinylformamide) was prepared by the same method. The material was purified by column chromatography over silica (dichloromethane, ethyl acetate, 7:1 v/v). Yield were in the range of 80% $^1$NMR (CDCl$_3$, δ=ppm) δ: 8.31, 8.17 (s, 2H); 7.26-7.14, 6.61-6.53 (m, 2H); 4.60-4.54 (m, 2H); 4.53-4.44 (m, 2H); 3.65-3.60, 3.53-3.48 (t, 4H); 1.96-1.84 (m, 2H).

N,N'-(dodecane-1,12-diyl)bis(N-vinylformamide) The material was purified by column chromatography over silica (anhydrous diethylether). Yields were in the range of 80%; $^1$NMR (CDCl$_3$, δ=ppm) δ: 8.28, 8.12 (s, 2H); 7.25-7.19, 6.59-6.51 (m, 2H); 4.63-4.35 (m, 2H); 4.42-4.40 (m, 2H); 3.57-3.52, 3.47-3.42 (t, 4H); 1.59-1.50 (m, 8H); 1.29-1.25 (m, 12H). The crosslinking monomers have the following structures:

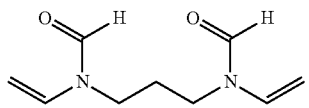

N,N'-(propane-1,3-diyl)bis(N-vinylformamide)

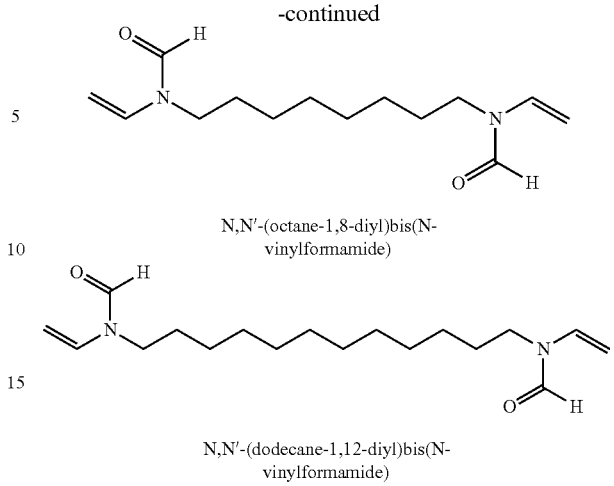

N,N'-(octane-1,8-diyl)bis(N-vinylformamide)

N,N'-(dodecane-1,12-diyl)bis(N-vinylformamide)

Example 2: Preparation of N-(3-tert-butoxycarbonylamino)propyl-N-vinylformamide (N-Boc aminopropyl N-VFA) amine monomer A dry 250 ml Schlenk flask was equipped with a magnetic stir bar, dropping funnel, and sealed with a rubber septum. The flask was purged with nitrogen and charged with N-vinylformamide (3.24 g, 45.6 mmol) and anhydrous THF (100 ml). The flask was cooled to 10° C. in an ice bath, and potassium tert-butoxide totaling 5.57 g (45.6 mmol) was added in three separate portions over 45 minutes through the top of the flask under nitrogen flow. tert-butyl 3-bromopropylcarbamate (43 mmol) was added slowly dropwise to the reaction mixture over 30 minutes. After addition, the reaction was allowed to warm up to room temperature and stir overnight. The solvent was removed in vacuo, and diluted with 150 ml of water. The water layer was extracted with diethyl ether (3×100 ml), dried over magnesium sulfate, and concentrated in vacuo. The material was further purified by column chromatography over silica (hexanes/ethyl acetate, 4:1 v/v). Yields were in the range of 60-80% and purity and structure were validated by $^1$H NMR.

Example 3: Preparation of N-(12-(bis-tert-butoxycarbonyl)amino)dodecyl-N-vinylformamide (N-bis Boc aminododecyl N-VFA) amine monomer A dry 250 ml Schlenk flask was equipped with a magnetic stir bar, dropping funnel, and sealed with a rubber septum. The flask was purged with nitrogen and charged with di-tert-butyl-iminodicarboxylate (45.6 mmol) and anhydrous THF (100 ml). The flask was cooled to 10° C. in an ice bath, potassium tert-butoxide totaling 5.57 g (45.6 mmol) were added in three separate portions over 45 minutes through the top of the flask under nitrogen flow. 1,12-dibromododecane (100 mmol) was added in three separate portions to the reaction mixture over 30 minutes. After addition, the reaction was allowed to warm up to room temperature and stir overnight. The solvent was removed in vacuo, and diluted with 150 ml of water. The water layer was extracted with diethyl ether (3×100 ml), dried over magnesium sulfate, and concentrated in vacuo. The material was further purified by column chromatography over silica (hexanes/ethyl acetate, 4:1 v/v). Yields were in the range of 60-80% and purity and structure were validated by 1H NMR.

N-(3-tert-butoxycarbonylamino)propyl-N-vinylformamide (N-Boc aminopropyl N-VFA) was made by the same process using 1,12-dibromopropane rather than 1,12-dibromododecane.

These amine monomers have the following structures:

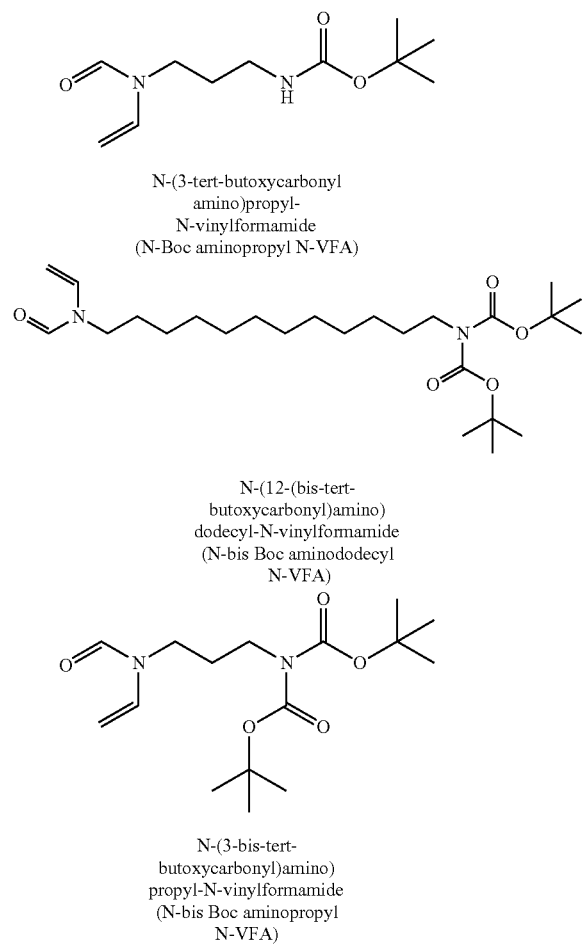

N-(3-tert-butoxycarbonyl
amino)propyl-
N-vinylformamide
(N-Boc aminopropyl N-VFA)

N-(12-(bis-tert-
butoxycarbonyl)amino)
dodecyl-N-vinylformamide
(N-bis Boc aminododecyl
N-VFA)

N-(3-bis-tert-
butoxycarbonyl)amino)
propyl-N-vinylformamide
(N-bis Boc aminopropyl
N-VFA)

Example 4: Synthesis of Polyvinylamine Polymers

Protocol 1: Conditions Mimicking the Lower Small Intestine (A Assay).

Amine polymers were measured in conditions mimicking those found in the lower small intestine (Northfield, T C and McColl, I (1973) "Postprandial concentrations of free and conjugated bile salts down the length of the normal human small intestine", Gut 14: 513-518, Borgstrom, B, et al. (1957) "Studies of intestinal digestion and absorption in the human", J Clin Invest 36: 1521-1536.)

The following test solution was prepared: 50 mM N,N-Bis(2-hydroxyethyl)-2-aminoethanesulfonic acid (BES), 50 mM sodium BES, 6.5 mM sodium phosphate, 0.93 mM sodium glycocholate, 0.93 mM sodium glycodeoxycholate, 150 mM sodium chloride, pH 7.0. The test solution was stored at −20° C. Before use the test solution was thawed in a 37° C. water bath, stirred vigorously on a stir plate for greater than 20 minutes, and filtered through a Nalgene 0.45 micron cellulose nitrate filter unit. This was found to provide reproducible results. Amine polymers to be analyzed were freeze-dried a minimum of 18 hours and were accurately dispensed into 16×100 mm borosilicate test tubes, with each tube containing between 23 and 28 mg of test sample. The precise weight was noted and the above solution was added using a 10 ml disposable pipette, so that the polymer concentration was 2.5 mg/ml. The tubes were covered with a sheet of Teflon, clamped and tumbled end-over-end (30-40 revolutions per minute) inside an atmospheric chamber at 37° C. for three hours. The polymers were recovered by centrifugation at 500×g for 10 minutes and the supernatants were sampled, filtered through a 96 well 0.45 micron Whatman Unifilter 800 by centrifugation at 1000×g for 10 minutes to remove any remaining particulates. Filtrates were transferred to either glass IC vials with rubber septa or 96 well polypropylene deep well sample plates.

To determine the concentration of glycocholate (GC) and glycodeoxycholate (GDC) in the filtrate, 50 μL of the sample solution was injected onto a HPLC system, equipped with Phenomenex Luna C8 (2) column (100 Å, 5 μm, 50×2.00 mm) and a UV detector. The sample was analyzed using a gradient of water, 25 mM phosphate buffer (pH=3) and acetonitrile at a flow rate of 0.4 mL/min. The signal of GC and GDC was detected at a wavelength of 205 nm from the UV detector. Calibration solutions comprised of GC and GDC standards of different concentrations were also injected onto the same HPLC system. The calibration curve of each component was then constructed by plotting the peak area vs. concentration. Based on the peak area of the GC and GDC found in the sample and the corresponding calibration curve, the concentration of each component in the sample was calculated in mM.

By comparing the equilibrium concentrations of glycocholate (GCeq) and glycodeoxycholate (GDCeq), in the presence of the polymer to their concentrations in test solution in the absence of the polymer, the amount of each component bound under these experimental conditions in mmoles/g polymer was calculated.

In some cases, the concentration of phosphate was also determined by injection of 20 ul of filtrate onto strong anion exchange columns (Dionex AG11-HC 50×4 mm ID and Dionex AS11-HC 250×4 mm ID) using a Waters Alliance 2795 Separation Module equipped with a 6 column switching valve installed inside a column oven and a Dionex Conductivity Detector CD25 (with DS3 flow cell and ASRS Ultra 11 4 mm Suppressor). The mobile phase was 30 mM KOH buffer with a 1 ml/min flow rate and a run time of 15 minutes per sample. Phosphate standards of different concentrations were also injected onto the same system and the calibration curve was then constructed by plotting the peak area vs. concentration. Based on the peak area found in the sample and the corresponding calibration curve, the concentration of phosphate in the sample was calculated in mM.

By comparing the equilibrium concentrations of phosphate (Peq) and in the presence of the polymer to their concentrations in test solution in the absence of the polymer, the amount of phosphate bound under these experimental conditions in mmoles/g polymer was calculated.

Protocol 2: Conditions Mimicking the Upper Small Intestine (Assay B).

Amine polymers were also measured in conditions mimicking those found in the upper small intestine after a meal (Fordtran, J S and Locklear, T W (1966) "Ionic constituents and osmolality of gastric and small-intestinal fluids after eating", Am J Dig Dis 11: 503-521; Northfield, T C and McColl, I (1973) "Postprandial concentrations of free and conjugated bile salts down the length of the normal human small intestine", Gut 14: 513-518; Evans, D F, et al. (1988) "Measurement of gastrointestinal pH profiles in normal ambulant human subjects", Gut 29: 1035-1041). The bile salt binding performance of test polymers was evaluated at a polymer concentration of 2.5 mg/ml in the manner described in Protocol 1 above, with the exception that the following test solution was used: 50 mM N,N-Bis(2-hydroxyethyl)-2-aminoethanesulfonic acid (BES), 50 mM sodium BES, 6.5 mM sodium phosphate, 4.6 mM sodium glycocholate, 4.6 mM sodium glycodeoxycholate, 1.2 mM oleyl glycerol, 9 mM oleic acid, 150 mM sodium chloride, pH 7.0. Freeze-dried polymer was precisely dispensed into the 16×100 mm borosilicate test tubes, with each tube containing between 28 and 33 mg of test sample. In certain cases, the concentration of polymer was adjusted from 2.5 mg/ml to 1 mg/ml. Otherwise the procedure was identical to that described in Protocol 1 above, except filtrates submitted for analytical analysis were only dispensed into glass IC vials.

To determine the concentration of glycocholate (GC), glycodeoxycholate (GDC), oleyl glycerol (OG) and oleic acid (OA) concentrations in filtrate samples, 20 µL was injected onto a HPLC system that was equipped with a Phenomenex Luna C8 (2) column (100 Å, 5 µm, 50×2.00 mm) and a UV detector. The sample was analyzed using a gradient of water, 25 mM phosphate buffer (pH=3) and acetonitrile at a flow rate of 0.4 mL/min. The signal of GC, GDC, OG and OA is detected at a wavelength of 205 nm from the UV detector. Calibration solutions comprised of GC, GDC, OG and OA standards of different concentrations were also injected onto the same HPLC system. The calibration curve of each component was then constructed by plotting the peak area vs. concentration. Based on the peak area of the GC, GDC, OG or OA found in the sample and the corresponding calibration curve, the concentration of each component in the sample is calculated in mM.

By comparing the equilibrium concentrations of glycocholate (GCeq), glycodeoxycholate (GDCeq), oleyl glycerol (OGeq) and/or oleic acid (OAeq) in the presence of the polymer to their concentrations in test solution in the absence of the polymer, the amount of each component bound under these experimental conditions in mmoles/g polymer was calculated.

Hamster Model. To collect in vivo data, Male Golden Syrian hamsters (8-9 weeks old) were obtained from Charles River Laboratories (Wilmington, Mass.). Upon arrival, the animals were placed on rodent diet Teklad 2018 (Madison, Wis.). Food and water were provided ad libitum throughout the course of the study. Animals were acclimated for at least seven days, and then randomized by body weight into groups of at least five animals each. All animals were then placed on a high-fat, high-sucrose western diet, D12079B (Research Diet, New Brunswick, N.J.) for three days before the study started. Amine polymers were blended into western diet at a dose of 0.5% to prepare the test diets. To initiate the study, all hamsters were moved into individual metabolic cages allowing the separation and collection of feces. Animals from the test groups were switched to the test diets, while animals from the untreated group were kept on western diet without added amine polymer. Food intake was measured for the next four consecutive days. For each hamster, feces from the last three days of the treatment period were collected, pooled, lyophilized, and then homogenized by grinding in a mortar and pestle. The feces samples were then extracted for fecal bile salt analysis.

In some cases, a baseline treatment period was conducted where all groups of animals were placed in metabolic cages as described above and fed only on western diet without added test article. Feces were collected as described above and the effect of amine polymer on bile salt fecal excretion was determined by comparing baseline versus treatment periods. Otherwise, the effect of amine polymer on bile salt fecal excretion was determined by comparing untreated versus test groups.

Hamster fecal bile salts were analyzed using a modification of the procedure reported by Porter and colleagues (Porter, J L. et al. 2003. Accurate enzymatic measurement of fecal bile salts in patients with malabsorption. J Lab Clin Med. 141:411-8). For each extraction, a 100 mg aliquot of dry feces was weighed into a 16×100 mm Pyrex test tube. 1 ml ethylene glycol with 0.7N NaOH was then added. The test tube was capped with a marble and heated at 190-200° C. for 2 h. After cooling, 1 ml of 20% NaCl and 0.2 ml 6N HCl were added. After brief mixing, 6 ml diethyl ether was added. The tube was capped, vortexed for 5 min, and then centrifuged at 1,000×g for 5 min. The diethyl ether phase was transferred into a 20 ml glass vial. Two additional extractions with 6 ml diethyl ether were performed and the extracts were pooled. The ether was completely evaporated under a stream of air. The residue was then dissolved in 3 ml methanol and bile salts (cholic acid, 3-OH-12Oxo-Cholanic Acid, chenodeoxycholic acid deoxycholic acid and lithocholic acid) were quantified by LC-MS.

The synthesis of poly(vinylamine) gels were conducted in a nitrogen filled glovebox using automated liquid dispensing robots. Crosslinkers were dispensed into 14 mL glass tubes and purged with nitrogen in the glovebox port for 40 minutes. N-vinylformamide (NVF), 2,2-Azobis(2-methylpropionitrile)(AIBN) (5 wt. % azobisisobutyronitrile in dimethylformamide (DMF) or dimethyl sulfoxide (DMSO)) and solvent (DMF or DMSO) were added to each vial. The vial plate was sealed and heated on a stirring plate for 24 h at 60° C. The solid polymer gels were then swollen and ground in DMF, washed with water (3×) and lyophilized until dry. The formamide group was subsequently hydrolyzed by dispensing a solution of potassium hydroxide (5M, 30% v/v water, 30% v/v methanol, 40% v/v isopropanol) to the powders in each vial, sealing the vial plate, and heating at 70° C. for 48 hours. The gels were rewashed with aqueous HCl (1 M), water, sodium hydroxide (1M), water (3×) and lyophilized until dry.

Poly(vinylamine) gels with incorporated hydrophobic comonomers were synthesized in a nitrogen filled glovebox using automated liquid dispensing robots. The comonomers and crosslinkers were dispensed into 14 mL glass tubes and purged with nitrogen in the glovebox port for 40 minutes. N-vinylformamide, 2,2-Azobis(2-methylpropionitrile) (5 wt. % AIBN in DMF or DMSO) and solvent (DMF or DMSO) were added to each vial. The vial plate was sealed and heated on a stirring plate for 24 hours at 60° C. The solid polymer gels were then swollen and ground in a mixture of water and ethanol, washed with methanol (3×) and water (3×) and lyophilized until dry. The formamide group was subsequently hydrolyzed by dispensing a solution of HCl (4M in dioxane) and water (2:1 v/v, respectively) to the powders in each vial, sealing the vial plate, and heating at 75° C. for 48 hours. The gels were rewashed with sodium hydroxide (1M), water (3×) and lyophilized until dry.

The ingredients were dispensed using liquid dispensing robotic tool. The N-Vinylformamide (NVF) monomer (Monomer 1) was dispensed neat into 14 ml vials. The additional monomers components (Monomer 2 and Monomer 3) were dispensed as 50 weight % solutions in either DMF or DMSO solvent. Solutions of crosslinker and AIBN initiator were dispensed into the 14 ml vial as 50 weight %, and 5 weight %, respectively. The solid content of the final reaction mixture was at 40 weight % of the total mass. The vials were equipped with magnetic stirrer, capped and heated at 65° C. for 20 hour. A clear hard gel formed in most of the vials. Gels were swelled and ground with DMF, washed three times with water and lyophilized to dryness. The formamide group was subsequently hydrolyzed by dispensing a solution of hydrochloric acid (HCl) (4M in dioxane) and water (2:1 v/v, respectively) to the powders in each vial, sealing the vial plate, and heating at 75° C. for 48 hours. Further hydrolysis in potassium hydroxide (5M, 30% v/v water, 30% v/v methanol, 40% v/v isopropanol) at 75° C. for 48 hours afforded complete hydrolysis of the formamide group. Gels were rewashed with water (4×) and lyophilized until dry.

The general procedure outlined above was followed to prepare various libraries. N-Vinylformamide (Monomer 1) was reacted with hydrophobic Monomer 2 and/or pendant Amine Monomer 3. The crosslinkers used in these libraries are listed in the table below together with weight (mg) of the different reactants. The initiator 2, 2-Azobis (2-methylpropionitrile) (AIBN) was at 0.5 mole % with respect to the monomers and crosslinker combined. Dimethyl formamide (DMF), dimethyl sulfoxide (DMSO) and water were used as solvent as indicated in the table. For library 3-, N-vinylformamide (Monomer 1) was reacted with different crosslinkers. The initiator, AIBN or 2,2'-azobis(2-amidinopropane) (AAPH), was at 0.5 mole % with respect to the monomers and crosslinker combined. Dimethyl sulfoxide or water was used as solvent.

For libraries 10, 7, 9, and 8, the general procedure outlined above was followed to prepare this library on a large scale for Hamster study. The ingredients were dispensed in a 60 ml vial.

| Sample # | Monomer 1 (M1) (mg) N-Vinyl formamide | Monomer 2 (M2) (mg) N-Decyl-N-Vinyl formamide | Monomer 3 (M3) (mg) (N-bis Boc Amino dodecyl N-VFA) | (N-bis Boc amino propyl N-VFA) | (N-Boc amino propyl N-VFA) | Crosslinker (XL) (mg) 1,3- propyl bis(N-Vinyl formamide) | 1,8- octylene bis(N-Vinyl formamide) | 1,12- dodecyl Bis(N-Vinyl formamide) | Mole Ratio M1:M2:M3:XL | Initiator (mg) AIBN | AAPH | Solvent (mg) DMF | DMSO | Water |
|---|---|---|---|---|---|---|---|---|---|---|---|---|---|---|
| 1-A1 | 320.8 | | | | 112.7 | 68.3 | | | 84:0:9:7 | 4.5 | | 826.3 | | |
| 1-A2 | 190.8 | | | | 258.6 | 52.3 | | | 65:0:28:7 | 3.4 | | 826.3 | | |
| 1-A3 | 80.6 | | | | 382.3 | 38.6 | | | 38:0:55:7 | 2.5 | | 826.3 | | |
| 1-A4 | 238.7 | 127.3 | | | 96.8 | 58.7 | | | 71:13:9:7 | 3.9 | | 826.3 | | |
| 1-A5 | 140.4 | 100.7 | | | 229.7 | 46.4 | | | 53:13:27:7 | 3.1 | | 826.3 | | |
| 1-A6 | 51.6 | 76.7 | | | 349.8 | 35.3 | | | 26:13:54:7 | 2.3 | | 826.3 | | |
| 1-B1 | 304.1 | | | | 106.8 | | 93.9 | | 84:0:9:7 | 4.3 | | 826.3 | | |
| 1-B2 | 183.1 | | | | 248.2 | | 72.7 | | 65:0:28:7 | 3.3 | | 826.3 | | |
| 1-B3 | 78.2 | | | | 370.8 | | 54.3 | | 37:0:55:7 | 2.5 | | 826.3 | | |
| 1-B4 | 228.0 | 121.6 | | | 92.4 | | 81.2 | | 71:13:9:7 | 3.7 | | 826.3 | | |
| 1-B5 | 135.4 | 97.1 | | | 221.4 | | 64.8 | | 53:13:27:7 | 3.0 | | 826.3 | | |
| 1-B6 | 50.2 | 74.6 | | | 340.1 | | 49.8 | | 26:13:54:7 | 2.3 | | 826.3 | | |
| 1-C1 | 292.0 | | | | 102.6 | | | 118.2 | 83:0:9:8 | 4.1 | | 826.3 | | |
| 1-C2 | 177.5 | | | | 240.5 | | | 92.4 | 65:0:27:8 | 3.2 | | 826.3 | | |
| 1-C3 | 76.4 | | | | 362.1 | | | 69.6 | 37:0:55:8 | 2.4 | | 826.3 | | |
| 1-C4 | 220.1 | 117.3 | | | 89.2 | | | 102.8 | 71:13:9:8 | 3.6 | | 826.3 | | |
| 1-C5 | 131.6 | 94.4 | | | 215.3 | | | 82.7 | 53:13:27:8 | 2.9 | | 826.3 | | |
| 1-C6 | 49.1 | 73.0 | | | 332.8 | | | 63.9 | 25:13:54:8 | 2.2 | | 826.3 | | |
| 2-A1 | 175.7 | 149.3 | | | 80.6 | 71.3 | | | 65:19:9:7 | 3.1 | | 720.0 | | |
| 2-A2 | 135.0 | 133.8 | | | 144.5 | 63.9 | | | 56:19:19:7 | 2.8 | | 720.0 | | |
| 2-A3 | 101.9 | 121.2 | | | 196.4 | 57.9 | | | 46:19:28:7 | 2.5 | | 720.0 | | |
| 2-A4 | 74.5 | 110.8 | | | 239.4 | 52.9 | | | 37:19:37:7 | 2.3 | | 720.0 | | |
| 2-A5 | 51.5 | 102.0 | | | 275.6 | 48.7 | | | 28:19:46:7 | 2.1 | | 720.0 | | |
| 2-A6 | 31.8 | 94.6 | | | 306.5 | 45.2 | | | 19:19:56:7 | 2.0 | | 720.0 | | |
| 2-B1 | 112.1 | 133.3 | | | 216.0 | 15.9 | | | 49:20:29:2 | 2.6 | | 720.0 | | |
| 2-B2 | 108.5 | 129.0 | | | 209.1 | 30.8 | | | 48:19:29:4 | 2.6 | | 720.0 | | |
| 2-B3 | 105.1 | 125.0 | | | 202.5 | 44.8 | | | 47:19:28:6 | 2.6 | | 720.0 | | |
| 2-B4 | 101.9 | 121.2 | | | 196.4 | 57.9 | | | 46:19:28:7 | 2.5 | | 720.0 | | |
| 2-B5 | 98.9 | 117.7 | | | 190.6 | 70.2 | | | 45:18:27:9 | 2.5 | | 720.0 | | |
| 2-B6 | 96.1 | 114.3 | | | 185.2 | 81.9 | | | 45:18:27:11 | 2.5 | | 720.0 | | |
| 2-C1 | 170.1 | 144.5 | | | 78.0 | | 84.3 | | 65:19:9:7 | 3.0 | | 720.0 | | |
| 2-C2 | 131.1 | 130.0 | | | 140.4 | | 75.8 | | 56:19:19:7 | 2.7 | | 720.0 | | |
| 2-C3 | 99.3 | 118.1 | | | 191.3 | | 68.9 | | 46:19:28:7 | 2.5 | | 720.0 | | |
| 2-C4 | 72.8 | 108.2 | | | 233.7 | | 63.1 | | 37:19:37:7 | 2.3 | | 720.0 | | |
| 2-C5 | 50.4 | 99.8 | | | 269.5 | | 58.2 | | 28:19:46:7 | 2.1 | | 720.0 | | |
| 2-C6 | 31.2 | 92.6 | | | 300.2 | | 54.0 | | 19:19:56:7 | 1.9 | | 720.0 | | |
| 2-D1 | 111.3 | 132.3 | | | 214.4 | | 19.3 | | 49:20:29:2 | 2.6 | | 720.0 | | |
| 2-D2 | 105.9 | 126.0 | | | 204.2 | | 41.3 | | 48:19:29:4 | 2.6 | | 720.0 | | |
| 2-D3 | 101.1 | 120.2 | | | 194.8 | | 61.4 | | 47:19:28:7 | 2.5 | | 720.0 | | |
| 2-D4 | 96.7 | 115.0 | | | 186.3 | | 79.6 | | 46:18:27:9 | 2.4 | | 720.0 | | |
| 2-D5 | 92.6 | 110.1 | | | 178.5 | | 96.4 | | 45:18:27:11 | 2.4 | | 720.0 | | |
| 3-A1 | 466.6 | | | | | 47.8 | | | 96:4 | 5.6 | | | 780.0 | |
| 3-A2 | 438.6 | | | | | | 76.1 | | 96:4 | 5.3 | | | 780.0 | |
| 3-A3 | 450.6 | | | | | | | 64.0 | 96:4 | 5.4 | | | 780.0 | |
| 3-A4 | 463.3 | | | | | 47.5 | | | 96:4 | | 9.2 | | | 780.0 |
| 3-B1 | 430.1 | | | | | 84.5 | | | 93:7 | 5.3 | | | 780.0 | |
| 3-B2 | 386.6 | | | | | | 128.5 | | 93:7 | 4.8 | | | 780.0 | |

-continued

| Sample # | Monomer 1 (M1) (mg) N-Vinyl formamide | Monomer 2 (M2) (mg) N-Decyl-N-Vinyl formamide | Monomer 3 (M3) (mg) (N-bis Boc Amino dodecyl N-VFA) | (N-bis Boc amino propyl N-VFA) | (N-Boc amino propyl N-VFA) | Crosslinker (XL) (mg) 1,3-propyl bis(N-Vinyl formamide) | 1,8-octylene bis(N-Vinyl formamide) | 1,12-dodecyl Bis(N-Vinyl formamide) | Mole Ratio M1:M2:M3:XL | Initiator (mg) AIBN | AAPH | Solvent (mg) DMF | DMSO | Water |
|---|---|---|---|---|---|---|---|---|---|---|---|---|---|---|
| 3-B3 | 404.8 | | | | | | 110.2 | | 93:7 | 5.0 | | | 780.0 | |
| 3-B4 | 427.3 | | | | | 84.0 | | | 93:7 | | 8.8 | | | 780.0 |
| 3-C1 | 399.0 | | | | | 115.9 | | | 90:10 | 5.1 | | | 780.0 | |
| 3-C2 | 345.7 | | | | | | | 169.9 | 90:10 | 4.4 | | | 780.0 | |
| 3-C3 | 367.4 | | | | | | 147.8 | | 90:10 | 4.7 | | | 780.0 | |
| 3-C4 | 396.4 | | | | | 115.2 | | | 90:10 | | 8.4 | | | 780.0 |
| 3-D1 | 372.0 | | | | | 143.1 | | | 87:13 | 4.9 | | | 780.0 | |
| 3-D2 | 312.5 | | | | | | | 203.3 | 87:13 | 4.2 | | | 780.0 | |
| 3-D3 | 336.4 | | | | | | 179.1 | | 87:13 | 4.5 | | | 780.0 | |
| 3-D4 | 369.7 | | | | | 142.2 | | | 87:13 | | 8.1 | | | 780.0 |
| 4-A1 | 317.0 | | | 162.7 | | 36.1 | | | 87:0:10:4 | 4.2 | | | 780.0 | |
| 4-A2 | 165.4 | | | 327.5 | | 24.2 | | | 67:0:29:4 | 2.8 | | | 780.0 | |
| 4-A3 | 63.3 | | | 438.6 | | 16.2 | | | 38:0:58:4 | 1.9 | | | 780.0 | |
| 4-B1 | 308.7 | | | 158.5 | | | 48.7 | | 87:0:10:4 | 4.1 | | | 780.0 | |
| 4-B2 | 162.5 | | | 321.8 | | | 33.0 | | 67:0:29:4 | 2.8 | | | 780.0 | |
| 4-B3 | 62.5 | | | 433.4 | | | 22.2 | | 38:0:58:4 | 1.9 | | | 780.0 | |
| 4-B4 | 282.2 | | | 144.9 | | | 89.0 | | 83:0:9:7 | 3.9 | | | 780.0 | |
| 4-B5 | 152.8 | | | 302.5 | | | 62.0 | | 65:0:28:7 | 2.7 | | | 780.0 | |
| 4-B6 | 60.0 | | | 415.6 | | | 42.6 | | 37:0:56:7 | 1.9 | | | 780.0 | |
| 4-C1 | 302.4 | | | 155.2 | | | | 58.3 | 87:0:10:4 | 4.0 | | | 780.0 | |
| 4-C2 | 160.2 | | | 317.3 | | | | 39.7 | 67:0:29:4 | 2.8 | | | 780.0 | |
| 4-C3 | 61.9 | | | 429.3 | | | | 26.9 | 38:0:58:4 | 1.9 | | | 780.0 | |
| 4-C4 | 271.9 | | | 139.6 | | | | 104.8 | 83:0:9:7 | 3.8 | | | 780.0 | |
| 4-C5 | 148.8 | | | 294.7 | | | | 73.8 | 65:0:28:7 | 2.7 | | | 780.0 | |
| 4-C6 | 58.9 | | | 408.2 | | | | 51.1 | 37:0:56:7 | 1.8 | | | 780.0 | |
| 4-D1 | 231.4 | 105.8 | | 137.1 | | 42.1 | | | 75:12:10:4 | 3.6 | | | 780.0 | |
| 4-D2 | 121.8 | 74.9 | | 291.0 | | 29.8 | | | 56:12:29:4 | 2.5 | | | 780.0 | |
| 4-D3 | 40.9 | 52.1 | | 404.6 | | 20.7 | | | 27:12:58:4 | 1.8 | | | 780.0 | |
| 4-D5 | 123.7 | 76.1 | | 295.7 | | 21.9 | | | 56:12:29:4 | 2.6 | | | 780.0 | |
| 5-A1 | 360.3 | 56.4 | | | | | | 98.7 | 90:5:6 | 4.6 | | | 780.0 | |
| 5-A2 | 342.7 | 138.9 | | | | | | 33.8 | 86:12:2 | 4.6 | | | 780.0 | |
| 5-A3 | 373.1 | 58.4 | | | | | 83.7 | | 90:5:6 | 4.8 | | | 780.0 | |
| 5-A4 | 346.8 | 140.6 | | | | | 28.0 | | 86:12:2 | 4.6 | | | 780.0 | |
| 5-A5 | 390.6 | 61.1 | | | | 63.2 | | | 90:5:6 | 5.0 | | | 780.0 | |
| 5-A6 | 332.3 | 134.7 | | | | 48.4 | | | 84:11:5 | 4.6 | | | 780.0 | |
| 5-B1 | 318.4 | 105.2 | | | | | | 92.1 | 85:9:6 | 4.3 | | | 780.0 | |
| 5-B2 | 312.2 | 126.6 | | | | | | 76.9 | 84:11:5 | 4.3 | | | 780.0 | |
| 5-B3 | 329.0 | 108.7 | | | | | 77.9 | | 85:9:6 | 4.5 | | | 780.0 | |
| 5-B4 | 320.8 | 130.1 | | | | | 64.7 | | 84:11:5 | 4.4 | | | 780.0 | |
| 5-B5 | 343.3 | 113.4 | | | | 58.7 | | | 85:9:6 | 4.7 | | | 780.0 | |
| 5-B6 | 314.6 | 127.6 | | | | 73.3 | | | 81:11:7 | 4.5 | | | 780.0 | |
| 5-C1 | 281.8 | 147.9 | | | | | | 86.3 | 80:14:6 | 4.1 | | | 780.0 | |
| 5-C2 | 286.7 | 116.2 | | | | | | 113.0 | 81:11:7 | 4.1 | | | 780.0 | |
| 5-C3 | 290.6 | 152.5 | | | | | 72.8 | | 80:14:6 | 4.2 | | | 780.0 | |
| 5-C4 | 298.4 | 121.0 | | | | | 96.3 | | 81:11:7 | 4.2 | | | 780.0 | |
| 5-C5 | 326.2 | 132.3 | | | | 57.0 | | | 83:11:6 | 4.5 | | | 780.0 | |
| 5-C6 | 293.8 | 119.1 | | | | 102.7 | | | 79:11:11 | 4.3 | | | 780.0 | |
| 5-D1 | 249.5 | 185.5 | | | | | | 81.2 | 75:19:6 | 3.8 | | | 780.0 | |
| 5-D2 | 258.5 | 104.8 | | | | | | 152.9 | 79:11:11 | 3.8 | | | 780.0 | |
| 5-D3 | 256.8 | 190.9 | | | | | 68.4 | | 75:19:6 | 3.9 | | | 780.0 | |
| 5-D4 | 273.1 | 110.7 | | | | | 132.2 | | 79:11:11 | 4.0 | | | 780.0 | |
| 5-D5 | 266.5 | 198.1 | | | | 51.2 | | | 75:19:6 | 4.1 | | | 780.0 | |
| 6-A1 | 200.0 | | 174.5 | | | | | 29.6 | 85:12:3 | 2.7 | | | 610.1 | |
| 6-A2 | 200.0 | | 503.7 | | | | | 36.3 | 70:27:3 | 3.3 | | | 1115.0 | |
| 6-A3 | 200.0 | | 1025.8 | | | | | 46.9 | 54:43:3 | 4.3 | | | 1915.5 | |
| 7-A1 | 2668.6 | 1400.2 | | | 2520.8 | | | 1361.5 | 63:11:19:7 | 49.0 | | | 12000.0 | |
| 7-A2 | 2344.6 | 1230.2 | | 3186.0 | | | | 1196.2 | 63:11:19:7 | 43.0 | | | 12000.0 | |
| 8-A1 | 2881.1 | | 4607.6 | | | | | 468.5 | 78:19:3 | 42.8 | | | 12000.0 | |
| 8-A2 | 1454.2 | | 6201.7 | | | | | 315.3 | 58:39:3 | 28.8 | | | 12000.0 | |
| 9-A1 | 3595.2 | | | | | | | 1559.1 | 91:9 | 45.7 | | | 7800.0 | |
| 10-A1 | 3550.8 | 1863.1 | | | | 535.5 | | | 81:14:5 | 50.7 | | | 9000.0 | |
| 10-A2 | 2769.0 | 1452.9 | | | | | 1734.8 | | 74:13:13 | 43.3 | | | 9000.0 | |
| 10-A3 | 3614.9 | 1194.2 | | | | | | 1140.8 | 83:9:7 | 50.1 | | | 9000.0 | |
| 10-A4 | 3689.2 | 577.3 | | | | | | 1684.1 | 86:5:9 | 49.3 | | | 9000.0 | |
| 10-A5 | 3285.3 | 1085.3 | | | | | | 1583.0 | 82:9:9 | 46.4 | | | 9000.0 | |

Bile acid binding capacity, affinity, and retention for each resulting polymer were determined via the A assay, B assay and hamster model as described above, and results are reported in the table below:

| Sample # | Bile acid binding capacity B Assay (mmol/g) | Bile acid binding affinity A Assay (mmol/g) | Bile acid retention Hamster (mmol/g) | % Primary Bile Acid in feces* | Swelling (g/g) |
|---|---|---|---|---|---|
| 1-A2 | 3.38 | 0.37 | | | |
| 1-A4 | 3.28 | 0.68 | | | |
| 1-A5 | 3.31 | 0.68 | | | |
| 1-B1 | 3.26 | 0.44 | | | |
| 1-B2 | 3.31 | 0.43 | | | |
| 1-B4 | 3.14 | 0.69 | | | |
| 1-B5 | 3.26 | 0.69 | | | |
| 1-C1 | 3.18 | 0.61 | | | |
| 1-C2 | 3.30 | 0.59 | | | |
| 1-C4 | 2.07 | 0.67 | | | |
| 1-C5 | 3.23 | 0.69 | | | |
| 1-C6 | 3.31 | 0.69 | | | |
| 2-A2 | 3.13 | 0.68 | | | |
| 2-A4 | 3.27 | 0.70 | | | |
| 2-A6 | 2.77 | 0.63 | | | |
| 2-B2 | 3.12 | 0.69 | | | |
| 2-B4 | 3.29 | 0.70 | | | |
| 2-B6 | 3.10 | 0.68 | | | |
| 2-C2 | 3.12 | 0.70 | | | |
| 2-C4 | 3.18 | 0.69 | | | |
| 2-D1 | 3.13 | 0.70 | | | |
| 2-D3 | 3.18 | 0.70 | | | |
| 2-D4 | 3.08 | 0.69 | | | |
| 3-A1 | 3.46 | 0.39 | | | |
| 3-A2 | 3.42 | 0.60 | | | |
| 3-A3 | 3.44 | 0.44 | | | |
| 3-A4 | 3.47 | 0.39 | | | |
| 3-B1 | 3.44 | 0.40 | | | |
| 3-B2 | 3.33 | 0.65 | | | |
| 3-B3 | 3.42 | 0.47 | | | |
| 3-B4 | 3.47 | 0.40 | | | |
| 3-C1 | 3.44 | 0.41 | | | |
| 3-C2 | 3.20 | 0.67 | | | |
| 3-C3 | 3.35 | 0.48 | | | |
| 3-C4 | 3.46 | 0.41 | | | |
| 3-D1 | 3.42 | 0.41 | | | |
| 3-D2 | 3.09 | 0.68 | | | |
| 3-D3 | 3.28 | 0.49 | | | |
| 3-D4 | 3.39 | 0.42 | | | |
| 4-A1 | 3.38 | 0.37 | | | |
| 4-B1 | 3.43 | 0.41 | | | |
| 4-B2 | 3.47 | 0.38 | | | |
| 4-B5 | 3.47 | 0.41 | | | |
| 4-C1 | 3.45 | 0.54 | | | |
| 4-C2 | 3.45 | 0.50 | | | |
| 4-C4 | 3.38 | 0.61 | | | |
| 4-C5 | 3.44 | 0.59 | | | |
| 4-D1 | 3.41 | 0.68 | | | |
| 4-D2 | 3.44 | 0.67 | | | |
| 5-A1 | 3.35 | 0.69 | | | |
| 5-A2 | 3.33 | 0.69 | | | |
| 5-A3 | 3.42 | 0.67 | | | |
| 5-A4 | 3.35 | 0.70 | | | |
| 5-A5 | 3.46 | 0.66 | | | |
| 5-A6 | 3.34 | 0.70 | | | |
| 5-C1 | 3.18 | 0.69 | | | |
| 5-C2 | 3.23 | 0.69 | | | |
| 5-C3 | 3.29 | 0.69 | | | |
| 5-C4 | 3.35 | 0.69 | | | |
| 5-C5 | 3.38 | 0.69 | | | |
| 5-C6 | 3.38 | 0.70 | | | |
| 5-D1 | 2.72 | 0.68 | | | |
| 5-D2 | 3.17 | 0.69 | | | |
| 5-D3 | 3.10 | 0.67 | | | |
| 5-D4 | 3.25 | 0.69 | | | |
| 5-D5 | 3.12 | 0.70 | | | |
| 6-A1 | 3.33 | 0.64 | | | |
| 6-A2 | 3.25 | 0.68 | | | |
| 6-A3 | 3.18 | 0.69 | | | |
| 7-A1 | 3.31 | 0.71 | 0.5 | 15.1 | 2.25 |
| 7-A2 | 3.36 | 0.71 | 0.39 | 8.4 | 1.79 |
| 8-A1 | 3.33 | 0.66 | 0.18 | 5.1 | 4.89 |
| 8-A2 | 3.25 | 0.68 | 0.39 | 6.7 | 2.06 |
| 9-A1 | 3.42 | 0.64 | 0.28 | 20.7 | 1.03 |
| 10-A1 | 3.17 | 0.73 | 0.27 | 23.6 | 3.93 |
| 10-A2 | 3.25 | 0.73 | 0.3 | 22.6 | 1.24 |
| 10-A3 | 3.39 | 0.73 | 0.26 | 31.2 | 1.12 |
| 10-A4 | 3.35 | 0.72 | | | 1.02 |
| 10-A5 | 3.21 | 0.73 | 0.18 | 45.8 | 0.8 |

*% Primary Bile Acids in feces as % of total measured: i.e. (Cholic acid + chenodeoxycholic acid) × 100/(Cholic acid + chenodeoxycholic acid + 3-OH-12Oxo-Cholanic Acid + deoxycholic acid + lithocholic acid)

Example 5: Synthesis of Comparative PVA Polymers

The general procedure outlined above was followed to prepare polymers from divinyl ether crosslinking monomers rather than bisvinylformamide crosslinking monomers.

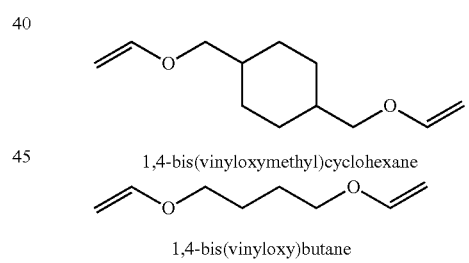

1,4-bis(vinyloxymethyl)cyclohexane 1,4-bis(vinyloxy)butane

N-Vinylformamide (Monomer 1) was reacted with crosslinkers listed in the table below. The initiator AIBN was at 0.5 mole % with respect to the monomers and crosslinker. Dimethyl formamide was used as solvent.

| | | Crosslinker | | | | |
|---|---|---|---|---|---|---|
| Sample # | Monomer 1 N-Vinyl Formamide (mg) | 1,4-bis(vinyloxy)-Butane (mg) | 1,4-bis(vinyloxy-methyl)-Cyclohexane (mg) | Mole Ratio Monomer1: Crosslinker | initiator AIBN (mg) | solvent DMF (mg) |
| 11-A1 | 460.1 | 9.2 | | 99:1 | 10.7 | 720 |
| 11-A2 | 441.2 | 28.2 | | 97:3 | 10.5 | 720 |
| 11-A3 | 423.9 | 45.8 | | 95:5 | 10.3 | 720 |
| 11-A4 | 407.9 | 62 | | 92:8 | 10.1 | 720 |
| 11-A5 | 393 | 77 | | 90:10 | 10 | 720 |

|  | | Crosslinker | | | | |
|---|---|---|---|---|---|---|
| Sample # | Monomer 1 N-Vinyl Formamide (mg) | 1,4-bis(vinyloxy)-Butane (mg) | 1,4-bis(vinyloxy-methyl)-Cyclohexane (mg) | Mole Ratio Monomer1: Crosslinker | initiator AIBN (mg) | solvent DMF (mg) |
| 11-A6 | 379.2 | 91 |  | 88:12 | 9.8 | 720 |
| 11-B1 | 456.7 |  | 12.6 | 99:1 | 10.7 | 720 |
| 11-B2 | 431.6 |  | 38.1 | 97:3 | 10.3 | 720 |
| 11-B3 | 409 |  | 61 | 95:5 | 10 | 720 |
| 11-B4 | 388.7 |  | 81.6 | 92:8 | 9.7 | 720 |
| 11-B5 | 370.4 |  | 100.2 | 90:10 | 9.4 | 720 |
| 11-B6 | 353.7 |  | 117.2 | 88:12 | 9.2 | 720 |

Bile acid binding capacity, affinity, and retention for each resulting polymers were determined via the A assay and B assay as described above, and results are reported in the table below.

| Sample # | Bile acid binding capacity B assay (mmol/g) | Bile acid binding affinity A assay (mmol/g) | swelling (g/g) |
|---|---|---|---|
| 11-A2 | 2.86 | 0.35 |  |
| 11-A3 | 3.37 | 0.37 | 29.05 |
| 11-A4 | 3.37 | 0.38 |  |
| 11-A5 | 3.42 | 0.40 |  |
| 11-A6 | 3.39 | 0.41 | 15.42 |
| 11-B2 | 3.15 | 0.37 |  |
| 11-B3 | 3.36 | 0.38 | 31.22 |
| 11-B4 | 3.45 | 0.39 |  |
| 11-B5 | 3.45 | 0.40 | 31.6 |
| 11-B6 | 3.45 | 0.42 |  |

Example 6: Synthesis of Acrylamide Monomers

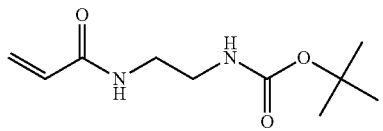

tert-butyl 2-acrylamidoethylcarbamate tert-Butyl 2-acrylamidoethylcarbamate synthesis

To a three neck 500 ml round flask, equipped with over head stirrer and nitrogen inlet, was charged with 15 g of N-t-butoxycarbonyl ethylenediamine (FW 160.2, 92.7 mmole). 70 ml of methylene chloride was then added followed by 30 ml of triethylamine (FW 101.2, 208.6 mmole). The resulted mixture was stirred under nitrogen blanket for 30 minutes in an ice cold bath. A solution made of 11.0 ml acryloyl chloride (FW 90.5, 139.1 mmole) in 50 ml methylene chloride was then added to the 500 ml round flask slowly through an additional funnel over 45 minutes. The temperature of the mixture was maintained below 5° C. The resulting mixture was stirred in ice bath for an additional one hour then warmed to ambient temperature overnight. A brownish solution with white precipitate was obtained. The mixture was extracted three times with 250 ml 0.5 M HCl aqueous solution. The organic layer was dried over magnesium sulfate (MgSO4) powder. Then, methylene chloride solvent was evaporated to dryness. A brownish powder 10 g (62% yield) was obtained. NMR spectra showed the desired product with impurities. A column chromatography was performed on the product over Silica gel 60. The eluent was made of ethyl acetate/methylene chloride mixture (v/v 40/60) respectively. The first fraction was collected and the column was eluted with 100% ethyl acetate solvent to collect the second fraction. The first fraction was passed through silica gel 60 column again (ethyl acetate/methylene chloride mixture (v/v 40:60)). The two fractions were combined and evaporated to dryness. A pure white powder was obtained 8.35 g (yield 49%).

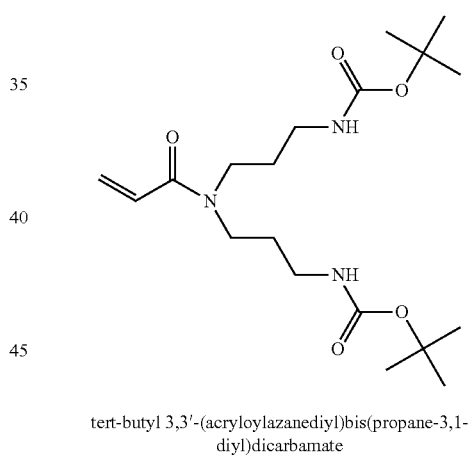

tert-butyl 3,3'-(acryloylazanediyl)bis(propane-3,1-diyl)dicarbamate tert-Butyl 3,3'-(acryloylazanediyl)bis(propane-3,1-diyl)dicarbamate synthesis A dry 1 L Schlenk flask was equipped with a magnetic stir bar, dropping funnel, and sealed with a rubber septum. tert-Butyl 3,3'-azanediylbis(propane-3,1-diyl)dicarbamate (22.0 g, 66.4 mmol) was dissolved in dichloromethane (450 ml) and triethylamine (13.9 mL, 99.6 mmol) and added to the flask. The mixture was cooled to 0° C. in an ice/water bath, and acryloyl chloride (4.0 g, 48.7 mmol) was added over 90 minutes via dropping funnel through the top of the flask under nitrogen flow. After addition, the reaction was allowed to stir at 55° C. for 6 hours. The reaction was cooled and solvent was removed in vacuo. The residue was diluted with 150 ml of hexanes and 60 mL of ethyl acetate and placed in a separatory funnel. The bottom layer was removed and purified by column chromatography over silica (dichloromethane/methanol, 9:1 v/v). Yield: 68%. 1H NMR δ: 6.60-6.50 (m, 1H); 6.40-6.30 (m, 1H); 5.71 (d, 1H); 5.43 (br s, 1H); 4.65 (br s, 1H); 3.50-3.29 (m, 4H); 3.18-3.01 (m, 4H); 1.83-1.62 (m, 4H); 1.42 (s, 18H).

Example 7: Preparation of N,N'-(decane-1,10-diyl)diacrylamide crosslinking monomer

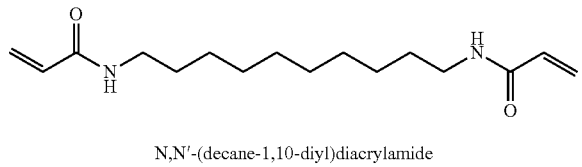 [SMILES: C=CC(=O)NCCCCCCCCCCNC(=O)C=C]

N,N'-(decane-1,10-diyl)diacrylamide

Into a dry 1000-mL, three-necked round-bottom flask equipped with an overhead stirrer and a dropping funnel were placed 8.6 g (0.05 mol) of 1,10-diaminodecane, 34 g (0.33 mol) of triethylamine and 200 mL of acetone (Aldrich acetone HPLC≥99.9%). The mixture was cooled to 15° C. in an ice bath under nitrogen and a total of 27 g (0.3 mol) of acryloyl chloride (97% Aldrich) was added dropwise with constant stirring over a period of 1 hour. The reaction was monitored with an internal temperature probe. When the addition was complete, the reaction was allowed to warm to ambient temperature and was stirred overnight. The reaction was terminated by the addition of 1 equivalent of water to the acryloyl chloride and allowed to stir for 30 minutes. The triethylamine hydrochloride salt was removed by passing the reaction solution through a filter. The reaction mixture was concentrated under reduced pressure and washed with 5% sodium bicarbonate, bubble evolved and a precipitate resulted. The white precipitate was washed with an excess of water and diethyl ether. The white precipitate was dissolved in a small amount of methanol and the product was precipitated again into water. The white precipitate was washed with diethyl ether and then dried under vacuum. The resulting powder was further purified by column chromatography over silica (dichloromethane/methanol, 9:1 v/v). The resulting yields were in the range of 50-70%. 1H NMR (CD3OD, 25° C., δ ppm, [6.2, 5.6, Olefin], [3.2-3.4 br-CH2-acrylamide, 1.6 br, 1.3 br-alkane]. MS m/e (MH+), calcd 280.22. found 281.3. A similar synthesis procedure can be used to make other N,N'—($C_m$alkane-1,m-diyl)diacrylamides.

Example 8: Synthesis of Polyacrylamide Hydrogels

Polyacrylamide gels were prepared in an inert atmosphere as solution polymerization in library format. Reactions were conducted using dispensing robots with liquid and powder dispensing capacities. The tert-butyl 2-acrylamidoethylcarbamate monomer (Monomer 1) was dispensed as powder into 14 ml vials. Solutions of crosslinker and initiator 2,2-Azobis (2-methylpropionitrile) (AIBN) were dispensed into the 14 ml vial as 50 weight %, and 10 weight %, respectively. The solid content of the final reaction mixture was at 40 weight % of the total mass. The vials were equipped with magnetic stirrer, capped and heated at 65° C. for 20 hour.

Hard gels formed in most of the vials. Gels were swelled and ground with dimethylformamide (DMF), washed three times with water and lyophilized to dryness.

The tert-butoxycarbonyl group was subsequently hydrolyzed by dispensing a solution of hydrochloric acid (HCl) (4M in dioxane) to the powders in each vial, sealing the vial plate, and heating at 75° C. for 24 hours. Gels were rewashed with water (4×) and lyophilized until dry.

| | | Crosslinker | | | | |
|---|---|---|---|---|---|---|
| Sample # | Monomer 1 tert-butyl 2-acrylamido-ethylcarbamate (mg) | Divinyl Benzene (mg) | N,N-Methylene-bis-Acrylamide (mg) | Mole Ratio Monomer1: Crosslinker | Initiator AIBN (mg) | Solvent DMF (mg) |
| 12-A1 | 796.1 | 3.9 | | 99:1 | 6.2 | 1193.8 |
| 12-A2 | 791.0 | 9.0 | | 98:2 | 6.2 | 1193.8 |
| 12-A3 | 786.0 | 14.0 | | 97:3 | 6.2 | 1193.8 |
| 12-A4 | 781.0 | 19.0 | | 96:4 | 6.2 | 1193.8 |
| 12-B1 | 795.4 | | 4.6 | 99:1 | 6.2 | 1193.9 |
| 12-B2 | 789.4 | | 10.6 | 98:2 | 6.2 | 1193.8 |
| 12-B3 | 783.4 | | 16.6 | 97:3 | 6.2 | 1193.8 |
| 12-B4 | 777.6 | | 22.4 | 96:4 | 6.2 | 1193.8 |

Example 9: Gel polymerization of tert-butyl 3,3'-(acryloylazanediyl)bis(propane-3,1-diyl)dicarbamate with hydrophobic comonomers Polyacrylamide gels copolymerized with hydrophobic comonomers were synthesized in a nitrogen filled glovebox using automated liquid dispensing robots. The constituents were weight out in a 40 ml glass vial, sealed with a rubber septum, and purged by bubbling nitrogen through the solution for 45 minutes. The vials were heated for 18 hours at 65° C. on an aluminum block mounted on a heated stirring plate. The solid polymer gels were then swollen and ground in a mixture of water and DMF, washed with methanol (3×), water (3×), and then lyophilized until dry. The tert-butoxycarbonyl protecting group was subsequently hydrolyzed by adding a solution of 40 ml of an HCl solution (4M in dioxane) to the powders in each vial, sealing the vial, and heating at 50° C. for 24 hours, then raising the temperature to 65° C. and heating for an additional 2 hours. The resins were neutralized and washed with 0.5M potassium hydroxide (3×). A solution of potassium hydroxide (5M, 30% v/v water, 30% v/v methanol, 40% v/v isopropanol) was added to each vial, the vials were resealed and heated at 75° C. for 24 hours. The gels were washed with methanol (2×), followed by water (3×), and lyophilized until dry.

| Sample # | Monomer1 (M1) tert-butyl 3,3'-(acryloyl-azanediyl)-bis(propane-3,1-diyl)-dicarbamate (mg) | Monomer 2 (M2) N-Decyl-Acrylamide (mg) | Crosslinker (XL) N,N'-(decane-1,10-diyl) Diacrylamide (mg) | Mole Ratio M1:M2:XL | Initiator AIBN (mg) | Solvent DMSO (mg) |
|---|---|---|---|---|---|---|
| 13-A1 | 6000.0 | | 130.9 | 97:0:3 | 26.3 | 9235.9 |
| 13-A2 | 6000.0 | | 436.4 | 91:0:9 | 28.1 | 9696.8 |
| 13-A3 | 6000.0 | 822.6 | 163.7 | 78:19:3 | 32.9 | 10528.8 |

Bile acid binding capacity, affinity, and retention for each resulting polymer were determined via the A assay, B assay and hamster model as described above, and results are reported in the table below.

| Sample # | Bile acid binding affinity A Assay (mmol/g) | Bile acid binding capacity B Assay (mmol/g) | Bile acid retention Hamster (mmol/g) | % Primary Bile Acid in feces* | Swelling (g/g) |
|---|---|---|---|---|---|
| 13-A1 | 0.42 | 3.31 | | | 11.5 |
| 13-A2 | 0.44 | 3.23 | 0.29 | 7.2 | 6.7 |
| 13-A3 | 0.67 | 2.94 | 0.31 | 5.7 | 2.2 |

*% Primary Bile Acids in feces as % of total measured: i.e. (Cholic acid + chenodeoxycholic acid) × 100/(Cholic acid + chenodeoxycholic acid + 3-OH-12Oxo-Cholanic Acid + deoxycholic acid + lithocholic acid)

Example 10: Synthesis of Crosslinked Polyallylamine Polymer Using Dihaloalkyl Crosslinker The reactions were carried out using appropriate size round bottom flasks with a nitrogen inlet port and hot plates equipped with silicon oil baths. In a typical reaction, polyallylamine polymer (15,000 MW) was dissolved in methanol to make a 17 wt % solution and then dispensed into a round bottom flask. 1,8-Dibromooctane was added to the flask drop wise with stirring. The reaction flask was capped using a rubber septum and nitrogen flow was introduced from the nitrogen inlet port. The reaction flask was then heated for 25 minutes at 55° C. Once the gel was formed, the reaction temperature was increased to 60° C. for 18 hours. The crosslinked polymer formed was swollen and ground in methanol and washed with methanol (two times), 0.3M sodium hydroxide, water (three times) and methanol (3 times) and then dried in vacuum oven at 50° C. for 2 days. The sample was further washed with 1M sodium chloride (2 times) and water (3 times) and lyophilized until dry and was submitted for in vitro screening.

Bile acid binding capacity, affinity, and retention for each resulting polymer were determined via the A assay, B assay and hamster model as described above, and results are reported in the table below.

| Sample # | Bile acid binding affinity A assay (mmol/g) | Bile acid binding capacity B assay (mmol/g) | Bile acid retention Hamster (mmol/g) | Swelling (g/g) |
|---|---|---|---|---|
| 14-C1 | | 3.08 | | 17.6 |

Example 11: Further Modification of Crosslinked Polyallylamine (Dihaloalkyl-Crosslinked) Using Alkyl Imidazolium Halide Ligands Polymer synthesized with polyallylamine and 1,8-dibromooctane was further modified by reacting the polymer with alkyl imidazolium halide ligands to attach a pendant alkyl imidazolium ligand to the scaffold. The polymer scaffold was first added to round bottom flasks with nitrogen inlet port. Then appropriate quantities of the ligands (3-(10-bromodecyl)-1-butyl-1H-imidazol-3-ium for 10-(1-butyl-1H-imidazol-3-ium-3-yl)decyl ligand, and 3-(10-bromodecyl)-1-decyl-2-methyl-1H-imidazol-3-ium for 10-(1-decyl-2-methyl-1H-imidazol-3-ium-3-yl)decyl ligand) were added to the flasks followed by addition of methanol as a reaction solvent. The reaction flasks were capped using rubber septum and nitrogen flow was introduced from the nitrogen inlet port. The reaction flasks were then heated for 66 hours at 60° C. using hotplates equipped with silicon oil baths. The polymer were then washed with methanol (2 times), 1M hydrochloric acid, 1 M sodium chloride (2 times) and water (3 times) and lyophilized until dry.

| Sample # | Polymer | Crosslinker (XL) | Polymer:Crosslinker Molar Ratio | Polymer (g) | Methanol (g) | Crosslinker (g) |
|---|---|---|---|---|---|---|
| 14-C1 | Pollyallylamine | Dibromooctane | 1:0.08 | 43 | 210 | 17.0 |

| Sample # | Polymer scaffold | Ligand | Polymer scaffold:Ligand Mole ratio | Polymer scaffold (g) | Methanol (g) | Ligand (g) |
|---|---|---|---|---|---|---|
| 14-B1 | Pollyallylamine + 1,8-dibromooctane crosslinker | 10-(1-butyl-1H-imidazol-3-ium-3-yl)decyl | 1:0.4 | 1 | 21 | 3 |
| 14 B2 | Pollyallylamine + 1,8-dibromooctane crosslinker | 10-(1-butyl-1H-imidazol-3-ium-3-yl)decyl | 1:0.67 | 1 | 23.7 | 5 |
| 14-B3 | Pollyallylamine + 1,8-dibromooctane crosslinker | 10-(1-decyl-2-methyl-1H-imidazol-3-ium-3-yl)decyl | 1:0.33 | 1 | 17.4 | 3 |
| 14-B4 | Pollyallylamine + 1,8-dibromooctane crosslinker | 10-(1-decyl-2-methyl-1H-imidazol-3-ium-3-yl)decyl | 1:0.55 | 1 | 23.7 | 5 |

Bile acid binding capacity, affinity, and retention for each resulting polymer were determined via the A assay, B assay and hamster model as described above, and results are reported in the table below.

| Sample # | Bile acid binding affinity A assay (mmol/g) | Bile acid binding capacity B assay (mmol/g) | Bile acid retention Hamster (mmol/g) | % Primary Bile Acids in feces* | Swelling (g/g) |
|---|---|---|---|---|---|
| 14-B1 | 0.56 | 2.49 | | | 11.9 |
| 14-B2 | 0.57 | 2.18 | 0.28 | 8.0 | 8.4 |
| 14-B3 | 0.65 | 2.54 | 0.37 | 4.4 | 8.3 |
| 14-B4 | 0.66 | 2.05 | | | 5.0 |

*% Primary Bile Acids in feces as % of total measured: i.e. (Cholic acid + chenodeoxycholic acid) × 100/(Cholic acid + chenodeoxycholic acid + 3-OH-12Oxo-Cholanic Acid + deoxycholic acid + lithocholic acid)

Example 12: Modification of Poly(Allylamine)(Epichlorohydrin-Crosslinked) with Neutral Ligands Poly(allylamine hydrochloride) crosslinked with 7% epichlorohydrin (ECH) ground gel was deprotonated by treating it with 1M sodium hydroxide until the pH of the solute reached about 12-14. The polymer was then washed extensively with water until the pH of the solute returned to about 7-8. This material was then lyophilized dry.

To prepare the larger scale animal samples with long chain hydrophobic ligands, deprotonated poly(allylamine) was weighed out into a 40 mL vial. To this was added methanol, then a 20% solution of ligand (bromooctane for n-octyl ligand, bromodecane for n-decyl ligand, bromododecane for n-dodecyl ligand, N-(2-(5-bromopentanamido)ethyl)-4-(nonyloxy)benzamide for 5-(2-(4-nonyloxy)benzamido)ethylamino)-5-oxopentyl ligand, 1-(10-bromodecyl)pyridinium for 10-(pyridinium-1-yl)decyl ligand, and N-(2-(1H-indol-3-yl)ethyl)-5-bromopentanamide for 5-(2-(1H-indol-3-yl)ethylamino)-5-oxopentyl ligand) in methanol. The vials were sealed and the mixture was stirred rapidly at 500 rpm and heated to 55° C. for 50 hours. The resulting polymer was washed with methanol, then with 1M sodium chloride (two times), followed by water (three times). Some samples were further deprotonated using the protocol described above.

To prepare the larger scale animal samples with the C-10 pyridinium or the amphiphilic ligands, the reaction was run in methanol (25 wt %) or NMP (5 wt %) and heated to 65° C. or 80° C., respectively. The resulting polymers were washed the same as in the previous samples.

| Sample # | Ligand | Solvent | Crosslinker:Amine Mol Ratio | Ligand:Amine Mol Ratio | Polymer (mg) | Ligand (mg) | Solvent (uL) |
|---|---|---|---|---|---|---|---|
| 15-A1 | n-octyl | Methanol | 0.07 | 0.2 | 2000 | 1245.94 | 6300.56 |
| 15-A2 | n-octyl | Methanol | 0.07 | 0.4 | 2000 | 2491.87 | 12601.12 |
| 15-A3 | n-octyl | Methanol | 0.07 | 0.6 | 2000 | 3737.81 | 18901.68 |
| 15-B1 | n-decyl | Methanol | 0.07 | 0.2 | 2000 | 1426.97 | 7216.02 |
| 15-B2 | n-decyl | Methanol | 0.07 | 0.4 | 2000 | 2853.94 | 14432.04 |
| 15-B3 | n-decyl | Methanol | 0.07 | 0.6 | 2000 | 4280.90 | 21648.06 |
| 15-B4 | n-decyl | Methanol | 0.07 | 0.4 | 2000 | 2503.11 | 12657.94 |
| 15-B5* | n-decyl | Methanol | 0.07 | 0.4 | 2000 | 350.83 | 1774.10 |
| 15-B6 | n-decyl | Methanol | 0.07 | 0.4 | 70000 | 88628.12 | 1144911.0 |
| 15-C1 | n-dodecyl | Methanol | 0.07 | 0.2 | 2000 | 1607.94 | 8131.15 |
| 15-C2 | n-dodecyl | Methanol | 0.07 | 0.4 | 2000 | 3215.87 | 16262.31 |
| 15-C3 | n-dodecyl | Methanol | 0.07 | 0.6 | 2000 | 4823.81 | 24393.46 |
| 15-C6* | n-dodecyl | Methanol | 0.07 | 0.4 | 2000 | 12171.89 | 157238.20 |
| 16-D1 | 10-(pyridinium-1-yl)-decyl | Methanol | 0.07 | 0.4 | 2000 | 4892.5 | 53107.5 |
| 17-D1 | 5-(2-(1H-indol-3-yl)ethylamino)-5-oxopentyl | NMP | 0.07 | 0.25 | 1500 | 2570.6 | 47510.4 |

*deprotonated samples

Bile acid binding affinity and capacity for each resulting polymer was determined via the A assay and B assay. For the in-vivo hamster model, bile acid was measured from the feces and used as a measure of retention of the polymers per gram of bile acid binding. The results are reported in the table below:

| Sample # | Bile acid binding capacity A assay (mmol/g) | Bile acid binding affinity B assay (mmol/g) | Bile acid retention Hamster (mmol/g) | % Primary Bile acid in feces* | swelling (g/g) |
|---|---|---|---|---|---|
| 15-A1 | 0.65 | 2.72 | | | 7.61 |
| 15-A2 | 0.66 | 2.16 | | | 2.37 |
| 15-A3 | 0.62 | 1.89 | | | 1.98 |
| 15-B1 | 0.68 | 2.64 | | | 6.39 |
| 15-B2 | 0.67 | 1.93 | | | 1.83 |
| 15-B3 | 0.64 | 1.39 | | | 1.72 |
| 15-B4 | | 1.93 | | | |
| 15-B5† | 0.66 | 2.34 | | | 0.44 |
| 15-B6 | 0.67 | 1.89 | | | 2.00 |
| 15-C1 | 0.68 | 2.54 | | | 3.47 |
| 15-C2 | 0.64 | 1.73 | | | 2.02 |
| 15-C3 | 0.62 | 1.33 | | | 2.00 |
| 15-C6† | 0.64 | 1.95 | 0.26 | 36.4 | 2.54 |
| 16-D1 | 0.53 | 2.56 | | | 6.26 |
| 17-D1 | 0.64 | 2.85 | 0.31 | 2.7 | 0.73 |

†deprotonated samples
*% Primary Bile Acids in feces as % of total measured: i.e. (Cholic acid + chenodeoxycholic acid) × 100/(Cholic acid + chenodeoxycholic acid + 3-OH-12Oxo-Cholanic Acid + deoxycholic acid + lithocholic acid)

Example 13: Modification of Poly(Allylamine) Polymers with Ligands

A 25 wt % solution of poly(allylamine) (MW 15,000) in N-methylpyrrolidone (NMP) was added to a 40 mL vial. To this was added a 50 wt % solution of crosslinker (1,10-dibromodecane (DBD) or 1,12-dibromododecane (DBDD)). The vials were sealed and the mixture was stirred rapidly at 500 RPM and heated to 80° C. for 18 hours. The resulting gel was ground in methanol, then washed with methanol (two times), 0.5M HCl (once), followed by water, 10 wt % NH$_4$OH, then water (three times). The resulting polymer was lyophilized dry to give a tacky polymer.

The dried polymer was weighed into a 40 mL vial. To this was then added NMP, followed by a 20 wt % solution of N-(2-(1H-indol-3-yl)ethyl)-5-bromopentanamide in NMP. The vials were sealed and stirred at 500 RPM, and heated at 80° C. for 18 hours. The resulting polymers were washed the same as in the previous samples.

Bile acid binding affinity and capacity for each resulting polymer was determined via the A assay and B assay. For the in-vivo hamster model, bile acid was measured from the feces and used as a measure of retention of the polymers per gram of bile acid binding. The results are reported in the table below.

| Sample # | Bile acid binding affinity A assay (mmol/g) | Bile acid binding capacity B assay (mmol/g) | Bile acid retention Hamster (mmol/g) | % Primary BA in feces* | Swelling (g/g) |
|---|---|---|---|---|---|
| 18-A1 | 0.60 | 3.27 | | | 3.03 |
| 18-B1 | 0.63 | 3.27 | 0.34 | 37.6 | 2.16 |

*% Primary Bile Acids in feces as % of total measured: i.e. (Cholic acid + chenodeoxycholic acid) × 100/(Cholic acid + chenodeoxycholic acid + 3-OH-12Oxo-Cholanic Acid + deoxycholic acid + lithocholic acid)

Example 14: Modification of Polyethyleneimine (Epichlorohydrin-Crosslinked) with Ligands Polyethyleneimine (PEI) beads were prepared in a 5 L reactor by mixing polyethyleneimine (MW 25,000), water, HCl (conc. 37% aqueous), Polystep A-16 (branched sodium dodecylbenzene sulfonate), and toluene in the reactor. The reaction was stirred under a nitrogen atmosphere for 30 minutes at 125 RMP. Then epichlorohydrin (ECH) was added as 40 wt % in toluene over a period of 30 minutes. After all the crosslinker was added, the reactor temperature was raised to 80° C. and maintained for 18 hours. The reaction was cooled and the beads were washed with methanol (three times), water (three times), 1M sodium hydroxide, then water until the pH was about 7-8. The beads were then lyophilized dry.

| Sample # | Polymer (mg) | Water (uL) | HCl (uL) | Polystep A-16 (mg) | Toluene (uL) | ECH (mg) |
|---|---|---|---|---|---|---|
| 19-A1 | 225,000 | 446,595.81 | 51,618.48 | 37,500 | 1,693,734 | 24,205.81 |

For the preparation of beads modified with ligands, the beads were weighed into a 100 mL jar, then to this was added dimethylformamide (DMF), followed by a 25 wt % solution of ligand ((chloromethyl)naphthalene for naphthalenemethyl ligand or 1-bromo-3-phenylpropane for 3-phenylpropyl ligand) in DMF. The reactions were sealed and stirred at 300 RPM and heated at 80° C. for 18 hours. The reactions were washed with methanol (two times), 1M hydrochloric acid, 1M sodium chloride (two times) and water (three times), then dried in the lyophilizer.

| Sample # | Crosslinker | Ligand | Crosslinker: Amine Mol Ratio | Ligand: Amine Mol Ratio | Polymer (mg) | Ligand (mg) | NMP (uL) |
|---|---|---|---|---|---|---|---|
| 18-A1 | DBD | 5-(2-(1H-indol-3-yl)ethylamino)-5-oxopentyl | 0.06 | 0.1 | 2000 | 284.7 | 12715.3 |
| 18-B1 | DBDD | 5-(2-(1H-indol-3-yl)ethylamino)-5-oxopentyl | 0.06 | 0.1 | 1800 | 228.2 | 12971.8 |

| Sample # | Ligand | Crosslinker: Amine Mole Ratio | Ligand: Amine Mole Ratio | Polymer (mg) | Ligand (mg) | DMF (uL) |
|---|---|---|---|---|---|---|
| 20-A2 | napthalenemethyl | 0.05 | 0.6 | 2742.7 | 6759.9 | 46381.6 |
| 21-B1 | 3-phenylpropyl | 0.05 | 0.6 | 2746.3 | 7629.4 | 46356.7 |

Bile acid binding affinity and capacity for each resulting polymer was determined via the A assay and B assay. For the in-vivo hamster model, bile acid was measured from the feces and used as a measure of retention of the polymers per gram of bile acid binding. The results are reported in the table below.

| Sample # | Bile acid binding affinity A assay (mmol/g) | Bile acid binding capacity B assay (mmol/g) | Bile acid retention Hamster (mmol/g) | % Primary BA in feces* | swelling (g/g) |
|---|---|---|---|---|---|
| 20-A2 | 0.15 | 0.64 | 0.14 | 35.6 | 1.04 |
| 21-B1 | 0.53 | 0.77 | 0.43 | 23.4 | 1.16 |

*% Primary Bile Acids in feces as % of total measured: i.e. (Cholic acid + chenodeoxycholic acid) × 100/(Cholic acid + chenodeoxycholic acid + 3-OH-12Oxo-Cholanic Acid + deoxycholic acid + lithocholic acid)

Example 15: Synthesis of Crosslinked Poly(Allylamine) Polymer Using Permanently Charged Dihalo Bis Piperidinium Crosslinkers The reactions were carried out in 14 ml glass test tubes using a 24 well parallel synthesis reactor equipped with hot plate stirrer. Poly(allylamine) polymer was dissolved in methanol to make a 17 wt % solution and then dispensed into the 14 ml test tubes using a micropipette. The permanently charged dihalo bis piperidinium crosslinkers (4,4'-(propane-1,3-diyl)bis(1-(8-bromooctyl)-1-methylpiperidinium (TMBMP-DBO) or 4,4'-(propane-1,3-diyl)bis(1-(3-bromopropyl)-1-methylpiperidinium (TMBMP-BDP)) were dissolved in methanol to make a 50 wt % solution and were added to the 14 ml tubes using micropipettes. The reaction mixtures were heated at 60° C. with stirring for 18 hours. The crosslinked polymers formed were swollen and ground in methanol and washed with methanol (two times), 1 M hydrochloric acid, and water (3 times) and lyophilized until dry.

Bile acid binding capacity, affinity, and retention for each resulting polymer were determined via the A assay, B assay and hamster model as described above, and results are reported in the table below:

| Sample # | Polymer | Crosslinker | Polymer: Crosslinker (mol) | Polymer (g) | Methanol (g) | Crosslinker (g) |
|---|---|---|---|---|---|---|
| 22-C1 | Pollyallylamine 15K | TMBMP-DBP | 1:0.03 | 0.2 | 1.03 | 0.056 |
| 22-C2 | Pollyallylamine 15K | TMBMP-DBP | 1:0.05 | 0.2 | 1.09 | 0.112 |
| 22-C3 | Pollyallylamine 15K | TMBMP-DBP | 1:0.08 | 0.2 | 1.15 | 0.169 |
| 22-C4 | Pollyallylamine 15K | TMBMP-DBP | 1:0.10 | 0.2 | 1.20 | 0.225 |
| 22-C5 | Pollyallylamine 15K | TMBMP-DBP | 1:0.13 | 0.2 | 1.26 | 0.282 |
| 22-C6 | Pollyallylamine 15K | TMBMP-DBP | 1:0.15 | 0.2 | 1.31 | 0.338 |
| 22-D1 | Pollyallylamine 15K | TMBMP-DBO | 1:0.03 | 0.2 | 1.05 | 0.069 |
| 22-D2 | Pollyallylamine 15K | TMBMP-DBO | 1:0.05 | 0.2 | 1.12 | 0.137 |
| 22-D3 | Pollyallylamine 15K | TMBMP-DBO | 1:0.08 | 0.2 | 1.18 | 0.206 |
| 22-D4 | Pollyallylamine 15K | TMBMP-DBO | 1:0.10 | 0.2 | 1.25 | 0.275 |
| 22-D5 | Pollyallylamine 15K | TMBMP-DBO | 1:0.12 | 0.2 | 1.03 | 0.343 |

| ISample # | Bile acid binding affinity A assay (mmol/g) | Bile acid binding capacity B assay (mmol/g) |
|---|---|---|
| 22-C1 | No gel | No gel |
| 22-C2 | No gel | No gel |
| 22-C3 |  | 3.25 |
| 22-C4 | 0.40 | 3.22 |
| 22-C5 |  | 3.17 |
| 22-C6 | 0.41 | 3.12 |
| 22-D1 |  | 3.30 |
| 22-D2 |  | 3.22 |
| 22-D3 | 0.44 | 3.18 |

| ISample # | Bile acid binding affinity A assay (mmol/g) | Bile acid binding capacity B assay (mmol/g) |
|---|---|---|
| 22-D4 |  | 3.13 |
| 22-D5 | 0.45 | 3.08 |

Example 16: Synthesis of Crosslinking Monomers

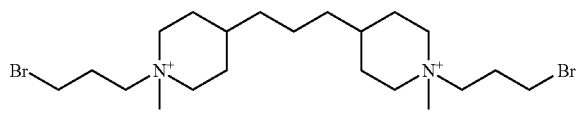

4,4'-(propane-1,3-diyl)bis(1-(3-bromopropyl)-1-methylpiperidinium)

4,4'-(propane-1,3-diyl)bis(1-(3-bromopropyl)-1-methylpiperidinium (TMBMP-BDP)

Into a round bottomed flask was weighed 42.34 g (0.21 moles) of dibromopropane and 20 mL of methanol. The flask was heated to 55° C. for 15-20 minutes. Then 10.0 g (0.041 mol) of 4,4'-Trimethylenebis(l-methylpiperidine) was added to the solution. The reaction mixture was allowed to stir for 12 hours and the reaction was stopped by the removal of heat and cooling to room temperature. The product was isolated by precipitation of the reaction solution into a solution of acetone:hexane 3:1 followed by filtration and washing with hexanes. The yield was over 90%. The product was identified by $^1$H NMR and mass spec.

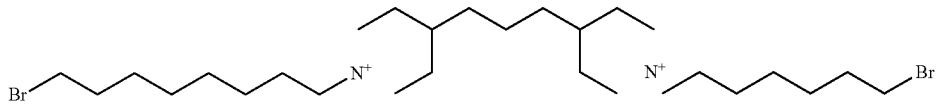

4,4'-(propane-1,3-diyl)bis(1-(8-bromooctyl)-1-methylpiperidinium)

4,4'-(propane-1,3-diyl)bis(1-(8-bromooctyl)-1-methylpiperidinium (TMBMP-DBO)

Into a round bottomed flask was weighed 34.22 g (0.126 moles) of dibromooctane and 20 mL of methanol. The flask was heated to 55° C. for 15-20 minutes. Then 10.0 g (0.041 mol) of 4,4'-Trimethylenebis(1-methylpiperidine) was added to the solution. The reaction mixture was allowed to stir for 12 hours and the reaction was stopped by the removal of heat and cooling to room temperature. The product was isolated by precipitation of the reaction solution into a solution of acetone:hexane 3:1 followed by filtration and washing with hexanes. The yield was over 90%. The product was identified by $^1$H NMR and mass spec.

Example 17: Synthesis of Polyethylenamine with Neutral Ligands

Polyethyleneimine (PEI) beads were prepared in a 5 L reactor by mixing polyethyleneimine (MW 25,000), water, HCl (conc. 37% aqueous), Polystep A-16 (branched sodium dodecylbenzene sulfonate), and toluene in the reactor. The reaction was stirred under a nitrogen atmosphere for 30 minutes at 125 RMP. Then to this was added epichlorohydrin (ECH) as a 40 wt % in toluene over a period of 30 minutes. After all the crosslinker was added, the reactor temperature was raised to 80° C. and maintained for 18 hours. The reaction was cooled and the beads were washed with Methanol (three times), water (three times), 1M sodium hydroxide, then water until the pH was about 7-8. The beads were then lyophilized dry.

| Library ID | PEI polymer (mg) | Water (uL) | HCl (uL) | Polystep A-16 (mg) | Toluene (uL) | ECH (mg) |
|---|---|---|---|---|---|---|
| 19-A1 | 225,000 | 446,595.81 | 51,618.48 | 37,500 | 1,693,734 | 24,205.81 |

For the preparation of beads modified with ligands, the beads were weighed into a 100 mL jar, DMF was added, followed by a 25 wt % solution of ligand in DMF. The reactions were sealed and stirred at 300 RPM and heated at 80° C. for 18 hours. The reactions were washed with methanol (2×), 1M HCl, 1M NaCl (2×) and water (3×), then dried in the lyophilizer.

| library ID | Ligand | Crosslinker: Amine Mole Ratio | Ligand: Amine Mole Ratio | Polymer (mg) | Ligand (mg) | DMF (uL) |
|---|---|---|---|---|---|---|
| 20-A2 | Chloromethyl napthalene | 0.05 | 0.6 | 2742.7 | 6759.9 | 46381.6 |

-continued

| library ID | Ligand | Crosslinker: Amine Mole Ratio | Ligand: Amine Mole Ratio | Polymer (mg) | Ligand (mg) | DMF (uL) |
|---|---|---|---|---|---|---|
| 21-B1 | 1-Bromo-3-phenylpropane | 0.05 | 0.6 | 2746.3 | 7629.4 | 46356.7 |

Bile acid binding affinity and capacity for each resulting polymer was determined via the A assay and B assay. For the in-vivo hamster model, bile acid was measured from the feces and used as a measure of retention of the polymers per gram of bile acid binding. The results are reported in the table below:

| library ID | Bile acid binding affinity A assay (mmol/g) | Bile acid binding capacity B assay (mmol/g) | Bile acid retention Hamster (mmol/g) | % Primary BA in feces* | swelling (g/g) |
|---|---|---|---|---|---|
| 20-A2 | 0.15 | 0.64 | 0.14 | 35.6 | 1.04 |
| 21-B1 | 0.53 | 0.77 | 0.43 | 23.4 | 1.16 |

*% Primary Bile Acids in feces as % of total measured: i.e. (Cholic acid + chenodeoxycholic acid) × 100/(Cholic acid + chenodeoxycholic acid + 3-OH-12Oxo-Cholanic Acid + deoxycholic acid + lithocholic acid)

Example 18: Synthesis of 1-Alkyl Methyl Pyrrolidine Ligand

Dibromoalkane (0.3 mol) was placed into a 3-necked flask that was fitted with an overhead stirrer. Acetone was added such that the resulting solution was 3M. A 1-methylpyrrolidine solution (0.03 mol) was dissolved in acetone to result in a 2M solution. This was added to the flask and the reaction was stirred overnight at 55° C. The isolation method depended on the form of the product, for example, when the product precipitated out of solution, the solid was filtered and washed with acetone and when the product was an oil, the acetone was vacuumed off and the product was purified either by column chromatography using 500 g of silica gel and $CH_2Cl_2$:methanol. The yield was in the range of 60-70% of materials that ranged from a clear oil to a white sold. The product was identified by $^1H$ NMR and mass spectrometry.

Example 19: Synthesis of Polymer Modified with 1,3 Dialkylimidazolium Bromide Ligand The desired polyamine scaffold gel was dissolved in water and neutralized with an equimolar solution of sodium hydroxide. An appropriate amount of a solution of 1,3-dialkylimidazolium bromide in methanol was added to the polyamine solution. The mixture was heated to 75° C. for 24 hours. After cooling to room temperature the modified polyamine gel was washed by exposing the gel to a 2× methanol wash, 0.5 M hydrochloric acid wash and 2× water washes. Each wash consisted of a process where the gel was stirred for 30 minutes, exposed to the washing solvent, centrifuged and the supernatant liquid was decanted off, and the wash solvent was added. After the final water wash, the gel was placed into a lyophilizer to remove the water. The gel was isolated as a white fluffy material.

Example 20: Synthesis of 1-alkyl-3-(1-bromoalkyl) imidazolium bromide

Dibromoalkane (0.3 mol) was placed into a 3-necked flask that was fitted with an overhead stirrer. Acetone was added such that the resulting solution was 3 M. Alkyl imidazole (0.03 mol) was dissolved in acetone to result in a 2M solution. This was added to the flask and the reaction was stirred overnight at 45-50° C. The next day, the acetone was vacuumed off and the product was purified by column chromatography using 500 g of silica gel and 90:10 $CH_2Cl_2$:Methanol. The yield was in the range of 60-70% of materials that ranged from a clear oil to a white sold. Product was identified by $^1H$ NMR and mass spec.

Example 21: Synthesis of 1-bromodecyl-N-pyridinium bromide

To a vigorously stirring flask of 1,10-dibromodecane (337.2 mL; 1.5 mmol) was added pyridine in acetone (50 vol. %; 16.2 mL; 0.1 mmol) dropwise over 5 hours at 30° C. After the addition was complete, the mixture was heated to 45° C. for 18 hours. The reaction mixture was allowed to cool slightly and the resulting white precipitate was filtered over a Buchner funnel. The product was washed thoroughly with hexanes (3×100 mL) and vacuum dried. The product was identified by $^1H$ NMR and mass spectrometry.

Example 22: Preparation of Bromodecyl(Methylimidazolium)Hydrobromide

A dry 250 mL Schlenk flask was equipped with a magnetic stir bar, dropping funnel, and sealed with a rubber septum. Dibromodecane (73.0 g, 0.24 mol) was dissolved in acetone (50 ml) and added to the flask. The mixture was heated to 55° C. in an oil bath, and 1-methylimidazole (4.0 g, 48.7 mmol) was added over 90 minutes via dropping funnel through the top of the flask under nitrogen flow. After addition, the reaction was allowed to stir at 55° C. for 6 hours. The reaction was cooled and solvent was removed in vacuo. The residue was diluted with 150 mL of hexanes and 60 mL of ethyl acetate and placed in a separatory funnel. The bottom layer was removed and purified by column chromatography over silica (dichloromethane/methanol, 9:1 v/v). Yield: 68%.

Example 23: Tryptamine ligand-N-(2-(1H-indol-3-yl)ethyl)-5-chloropentanamide

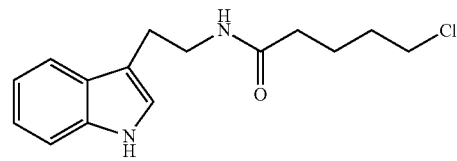 [SMILES: O=C(CCCCCl)NCCc1c[nH]c2ccccc12]

A solution of 2-(1H-indol-3-yl)ethanamine (5.10 g, 0.032 mol) and diisopropylethyl amine (7.23 mL, 0.042 mol) in 100 mL of dichloromethane was cooled to 4° C. in ice bath. 5-Chloro-valeroyl chloride (4.2 mL, 0.32 mol) was dissolved in 50 mL of dichloromethane and was added to the solution of 2-(1H-indol-3-yl)ethanamine dropwise. The internal temperature remained at or below 4° C. during the addition. After the addition, the reaction was warmed to room temperature and stirred for 2 hours. The mixture was washed with 1N HCl (2×150 mL), brine (150 mL), saturated $NaHCO_3$ solution (150 mL), and brine (150 mL). The organic phase was dried over $MgSO_4$ and concentrated. The crude product was purified by flash chromatography (silica gel, 15% methanol in dichloromethane). Pure product (7.9 gram) was obtained as a yellow solid (89%). MS m/e (MH+), calculated 279.13. found 279.16. This synthesis can be used to make other amino acid-based ligands by substituting the appropriate amine reactant for 2-(1H-indol-3-yl) ethanamine (e.g., use of 3-methylbutan-1-amine to make a Leu-based ligand).

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above polymers, pharmaceutical compositions, and methods of treatment without departing from the scope of the invention, it is intended that all matter contained in the above description and shown in the accompanying drawing[s] shall be interpreted as illustrative and not in a limiting sense.

What is claimed is:

1. A crosslinked amine polymer comprising repeat units derived from reaction of a crosslinking agent and an amine repeat unit, the amine repeat unit being either an allyl amine repeat unit of formula 14 or a polyethyleneimine repeat unit of formula 15, wherein the repeat units of formulae 14 and 15 have the structures:

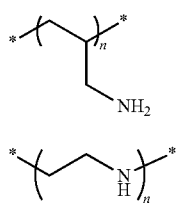

(14)

(15)

wherein n is an integer, and the crosslinking agent is X—$R_1$—X or epihalohydrin wherein $R_1$ is independently $C_8$ to $C_{50}$ alkylene, each X is independently a leaving group, and a portion of the nitrogen atoms of the crosslinked amine polymer are substituted with a ligand selected from 2-(protected amino)-m-(heterocyclo)-1-oxo$C_m$alkyl, 2-(protected amino)-1-oxo$C_m$alkyl, 2-(protected amino)-3-methyl-1-oxo$C_m$alkyl, 2-(protected amino)-4-methyl-1-oxo$C_m$alkyl, 2-(protected amino)-1-oxo-m-aryl$C_m$alkyl, 2-(protected amino)-m-(alkylthio)-1-oxo$C_m$alkyl, 2-(protected amino)-m-(aryl)-1-oxo$C_m$alkyl, 2-(protected amino)-m-carboxy-1-oxo$C_m$alkyl, 2-(protected amino)-m-guanidino-1-oxo$C_m$alkyl, 2-(protected amino)-(m-1)-hydroxy-1-oxo$C_m$alkyl, 2-(protected amino)-m-hydroxy-1-oxo$C_m$alkyl, 2-(protected amino)-m-mercapto-1-oxo$C_m$alkyl, m-(alkylamino)-m-oxo$C_m$alkyl, m-(alkylheterocyclo)$C_m$alkyl, m-amino-2-(protected amino)-1-oxo$C_m$alkyl, m-amino-2-(protected amino)-1,m-dioxo$C_m$alkyl, m-(x-amino$C_x$alkyl)heterocyclo$C_m$alkyl, (m-1)-amino-m-(heterocyclo)-1-oxo$C_m$alkyl, m-(arylalkylamino)-m-oxo$C_m$alkyl, m-(x-(alkylthio)$C_x$alkylamino)-m-oxo$C_m$alkyl, m-(x-amino$C_x$alkylamino)-m-oxo$C_m$alkyl, m-(x-amino-x-oxo$C_x$alkylamino)-m-oxo$C_m$alkyl, m-(x-carboxy$C_x$alkylamino)-m-oxo$C_m$alkyl, m-(heterocycloalkylamino)-m-oxo$C_m$alkyl, m-(x-hydroxy$C_x$alkylamino)-m-oxo$C_m$alkyl, m-((x-1)-hydroxy$C_x$alkylamino)-m-oxo$C_m$alkyl, m-(x-mercapto$C_x$alkylamino)-m-oxo$C_m$alkyl, m-(x-trialkylammonio$C_x$alkyl)heterocyclo$C_m$alkyl, m-(x-(2-(alkoxy)benzamido)$C_x$alkylamino)-m-oxo$C_m$alkyl, m-(x-(3-(alkoxy)benzamido)$C_x$alkylamino)-m-oxo$C_m$alkyl, m-(x-(4-(alkoxy)benzamido)$C_x$alkylamino)-m-oxo$C_m$alkyl, heterocycloalkyl selected from m-(1-methylpyrrolidinium-1-yl)$C_m$alkyl, m-(2-(1H-indol-3-yl)ethylamino)-m-oxo$C_m$alkyl, m-(2-methylthiazol-3-ium-3-yl)$C_m$alkyl, m-(benzo[d]thiazol-3-ium-3-yl)$C_m$alkyl, m-(pyridinium-1-yl)$C_m$alkyl, m-(tetrahydro-1H-thiophenium-1-yl)$C_m$alkyl, z-(1,2-dialkyl-1H-imidazol-3-ium-3-yl)$C_z$alkyl, m-(2,3-dialkyl-1H-imidazol-3-ium-1-yl)$C_m$alkyl, z-(1-alkyl-1H-imidazol-3-ium-3-yl)$C_z$alkyl, m-(3-alkyl-1H-imidazol-3-ium-1-yl)$C_m$alkyl, or z-(thiazol-3-ium-3-yl)$C_z$alkyl; 2-(protected amino)-m-(heterocyclo)-1-oxo$C_m$alkyl selected from 2-(protected amino)-m-(1H-indol-3-yl)-1-oxo$C_m$-alkyl or 2-(protected amino)-m-(1H-imidazol-4-yl)-1-oxo$C_m$alkyl; 2-(protected amino)-1-oxo-m-phenyl$C_m$alkyl; 2-(protected amino)-m-(hydroxyphenyl)-1-oxo$C_m$alkyl; m-(alkylheterocyclo)$C_m$alkyl selected from m-(3-alkyl-1H-imidazol-3-ium-1-yl)$C_m$alkyl, m-(1-alkyl-1H-imidazol-3-ium-3-yl)$C_m$alkyl, m-(1-alkyl-2-methyl-1H-imidazol-3-ium-3-yl)$C_m$alkyl, or m-(3-alkyl-2-methyl-1H-imidazol-3-ium-1-yl)$C_m$alkyl; m-(x-amino$C_x$alkyl)heterocyclo$C_m$alkyl selected from m-(3-(x-amino$C_x$alkyl)-1H-imidazol-3-ium-1-yl)$C_m$alkyl or m-(1-(x-amino$C_x$alkyl)-1H-imidazol-3-ium-3-yl) $C_m$alkyl; (m-1)-amino-m-(1H-indol-2-yl)-1-oxo$C_m$alkyl; m-(arylalkylamino)-m-oxo$C_m$alkyl selected from m-(hydroxyphenalkylamino)-m-oxo$C_m$alkyl or m-(phenalkylamino)-m-oxo-$C_m$alkyl; m-(x-(heterocyclo)$C_x$alkyl)heterocyclo$C_m$alkyl selected from m-(1-(x-(1-methyl-1H-imidazol-3-ium-3-yl)$C_x$alkyl)-1H-imidazol-3-ium-3-yl) $C_m$alkyl, m-(1-(x-(3-methyl-1H-imidazol-3-ium-1-yl)$C_x$alkyl)-1H-imidazol-3-ium-3-yl) $C_m$alkyl, m-(3-(x-(1-methyl-1H-imidazol-3-ium-3-yl)$C_x$alkyl)-1H-imidazol-3-ium-1-yl) $C_m$alkyl, or m-(3-(x-(3-methyl-1H-imidazol-3-ium-1-yl)$C_x$alkyl)-1H-imidazol-3-ium-1-yl) $C_m$alkyl; m-(x-(1H-imidazol-4-yl)$C_x$alkylamino)-m-oxo$C_m$alkyl; or m-(x-trialkylammonio$C_x$alkyl)heterocyclo$C_m$alkyl selected from m-(3-(x-trialkylammonio)$C_x$alkyl)-1H-imidazol-3-ium-1-yl)$C_m$alkyl or m-(1-(x-trialkylammonio)$C_x$alkyl)-1H-imidazol-3-ium-3-yl)$C_m$alkyl, a ligand of formula 6

*—$R_{46}$—$R_{47}$—$R_{48}$ (6)

or a combination thereof, wherein $R_{46}$ is $C_6$ to $C_{16}$ alkylene, $R_{47}$ is 1,y-bis(1-methylpiperidin-4-yl)$C_y$alkylene, $R_{48}$ is $C_6$ to $C_{16}$ alkyl, m is an integer from 3 to 12, x is an integer from 1 to 12, y is an integer from 1 to 14, and z is an integer from 1 to 16.

2. The polymer of claim 1 wherein $R_1$ is a $C_{10}$ to $C_{14}$ alkylene.

3. The polymer of claim 1 herein the ligand has a molecular weight less than about 1600 Daltons.

4. The polymer of claim 3 wherein the ligand has a molecular weight less than about 800 Daltons.

5. The polymer of claim 1, wherein the ligand is heterocycloalkyl selected from m-(1-methylpyrrolidinium-1-yl)$C_m$alkyl, m-(2-(1H-indol-3-yl)ethylamino)-m-oxo$C_m$alkyl, m-(2-methylthiazol-3-ium-3-yl)$C_m$alkyl, m-(benzo[d]thiazol-3-ium-3-yl)$C_m$alkyl, m-(pyridinium-1-yl)$C_m$alkyl, m-(tetrahydro-1H-thiophenium-1-yl)$C_m$alkyl, z-(1,2-dialkyl-1H-imidazol-3-ium-3-yl)$C_z$alkyl, m-(2,3-dialkyl-1H-imidazol-3-ium-1-yl)$C_m$alkyl, z-(1-alkyl-1H-imidazol-3-ium-3-yl)$C_z$alkyl, m-(3-alkyl-1H-imidazol-3-ium-1-yl) $C_m$alkyl, or z-(thiazol-3-ium-3-yl)$C_z$alkyl; 2-(protected amino)-m-(heterocyclo)-1-oxo$C_m$alkyl selected from 2-(protected amino)-m-(1H-indol-3-yl)-1-oxo$C_m$-alkyl or 2-(protected amino)-m-(1H-imidazol-4-yl)-1-oxo$C_m$alkyl; 2-(protected amino)-1-oxo-m-phenyl$C_m$alkyl; 2-(protected amino)-m-(hydroxyphenyl)-1-oxo$C_m$alkyl; m-(alkylheterocyclo)$C_m$alkyl selected from m-(3-alkyl-1H-imidazol-3-ium-1-yl)$C_m$alkyl, m-(1-alkyl-1H-imidazol-3-ium-3-yl) $C_m$alkyl, m-(1-alkyl-2-methyl-1H-imidazol-3-ium-3-yl)

$C_m$alkyl, or m-(3-alkyl-2-methyl-1H-imidazol-3-ium-1-yl) $C_m$alkyl; m-(x-aminoC$_x$alkyl)heterocycloC$_m$alkyl selected from m-(3-(x-aminoC$_x$alkyl)-1H-imidazol-3-ium-1-yl) $C_m$alkyl or m-(1-(x-aminoC$_x$alkyl)-1H-imidazol-3-ium-3-yl) $C_m$alkyl; (m-1)-amino-m-(1H-indol-2-yl)-1-oxoC$_m$alkyl; m-(arylalkylamino)-m-oxoC$_m$alkyl selected from m-(hydroxyphenalkylamino)-m-oxoC$_m$alkyl or m-(phenalkylamino)-m-oxo-C$_m$alkyl; m-(x-(heterocyclo)C$_x$alkyl)heterocycloC$_m$alkyl selected from m-(1-(x-(1-methyl-1H-imidazol-3-ium-3-yl)C$_x$alkyl)-1H-imidazol-3-ium-3-yl) $C_m$alkyl, m-(1-(x-(3-methyl-1H-imidazol-3-ium-1-yl)C$_x$-alkyl)-1H-imidazol-3-ium-3-yl) $C_m$alkyl, m-(3-(x-(1-methyl-1H-imidazol-3-ium-3-yl)C$_x$alkyl)-1H-imidazol-3-ium-1-yl) $C_m$alkyl, or m-(3-(x-(3-methyl-1H-imidazol-3-ium-1-yl)C$_x$alkyl)-1H-imidazol-3-ium-1-yl) $C_m$alkyl; m-(x-(1H-imidazol-4-yl)C$_x$alkylamino)-m-oxoC$_m$alkyl; or m-(x-trialkylammonioC$_x$alkyl)heterocycloC$_m$alkyl selected from m-(3-(x-trialkylammonio)C$_x$alkyl)-1H-imidazol-3-ium-1-yl)C$_m$alkyl or m-(1-(x-trialkylammonio)C$_x$alkyl)-1H-imidazol-3-ium-3-yl)C$_m$alkyl wherein m is an integer from 3 to 12, x is an integer from 1 to 12, and z is an integer from 1 to 16.

6. The polymer of claim 1, wherein the ligand is 2-(protected amino)-m-(heterocyclo)-1-oxoC$_m$alkyl, m-amino-2-(protected amino)-1,m-dioxoC$_m$alkyl, m-amino-2-(protected amino)-1-oxoC$_m$alkyl, 2-(protected amino)-1-oxoC$_m$alkyl, 2-(protected amino)-m-(alkylthio)-1-oxoC$_m$alkyl, 2-(protected amino)-m-(hydroxyphenyl)-1-oxoC$_m$alkyl, 2-(protected amino)-1-oxo-m-phenylC$_m$alkyl, 2-(protected amino)-m-(1H-imidazol-4-yl)-1-oxoC$_m$alkyl, 2-(protected amino)-m-carboxy-1-oxoC$_m$alkyl, 2-(protected amino)-3-methyl-1-oxoC$_m$alkyl, 2-(protected amino)-4-methyl-1-oxoC$_m$alkyl, 2-(protected amino)-m-mercapto-1-oxoC$_m$alkyl, 2-(protected amino)-(m-1)-hydroxy-1-oxoC$_m$alkyl, 2-(protected amino)-m-hydroxy-1-oxoC$_m$alkyl, 2-(protected amino)-m-guanidino-1-oxoC$_m$alkyl, m-(x-(alkylthio)C$_x$alkylamino)-m-oxoC$_m$alkyl, m-(hydroxyphenalkylamino)-m-oxoC$_m$alkyl, m-oxo-m-(phenalkylamino) $C_m$alkyl, m-(x-(1H-imidazol-4-yl)C$_x$alkylamino)-m-oxoC$_m$alkyl, m-(x-carboxyC$_x$alkylamino)-m-oxoC$_m$alkyl, m-(alkylamino)-m-oxoC$_m$alkyl, m-(x-mercaptoC$_x$alkylamino)-m-oxoC$_m$alkyl, m-((x-1)-hydroxyC$_x$alkylamino)-m-oxoC$_m$alkyl, m-(x-hydroxyC$_x$alkylamino)-m-oxoC$_m$alkyl, m-(x-aminoC$_x$alkylamino)-m-oxoC$_m$alkyl, or m-(x-amino-x-oxoC$_x$alkylamino)-m-oxoC$_m$alkyl, wherein m is an integer from 3 to 12, and x is an integer from 1 to 12.

7. The polymer of claim 1, wherein the ligand is of formula 6 and $R_{46}$ is $C_8$ to $C_{12}$ alkylene, $R_{47}$ is 1,y-bis(1-methylpiperidin-4-yl)C$_y$alkylene, $R_{48}$ is $C_8$ to $C_{12}$ alkyl, and y is an integer from 1 to 6.

8. The polymer of claim 1, wherein the ligand is 2-(tert-butoxycarbonylamino)-3-(1H-indol-3-yl)-1-oxopropyl, 5-(2-(4-(nonyloxy)benzamido)ethylamino)-5-oxopentyl, 10-(pyridinium-1-yl)decyl, 5-(2-(1H-indol-3-yl)ethylamino)-5-oxopentyl, 2-amino-3-(1H-indol-2-yl)-1-oxopropyl, 3-(1,2-dimethyl-1H-imidazol-3-ium-3-yl)propyl, 10-(1,2-dimethyl-1H-imidazol-3-ium-3-yl)decyl, 10-(1-methyl-1H-imidazol-3-ium-3-yl)decyl, 3-(thiazol-3-ium-3-yl)propyl, 3-(1-methylpyrrolidinium-1-yl)propyl, 3-(2-methylthiazol-3-ium-3-yl)propyl, 3-(benzo[d]thiazol-3-ium-3-yl)propyl, 3-(tetrahydro-1H-thiophenium-1-yl) propyl, 3-(3-methyl-1H-imidazol-3-ium-1-yl)propyl, 3-(1-methyl-1H-imidazol-3-ium-3-yl)propyl, 3-(3-(3-aminopropyl)-1H-imidazol-3-ium-1-yl)propyl, 3-(1-(3-aminopropyl)-1H-imidazol-3-ium-3-yl)propyl, 3-(3-(5-trimethylammonio)pentyl)-1H-imidazol-3-ium-1-yl)propyl, 3-(1-(5-trimethylammonio)pentyl)-1H-imidazol-3-ium-3-yl)propyl, 3-(3-decyl-1H-imidazol-3-ium-1-yl)propyl, 3-(1-decyl-1H-imidazol-3-ium-3-yl)propyl, 3-(3-(9-(3-methyl-1H-imidazol-3-ium-1-yl)nonyl)-1H-imidazol-3-ium-1-yl) propyl, 3-(1-(9-(1-methyl-1H-imidazol-3-ium-3-yl)nonyl)-1H-imidazol-3-ium-3-yl)propyl, 3-(1-(9-(3-methyl-1H-imidazol-3-ium-1-yl)nonyl)-1H-imidazol-3-ium-3-yl) propyl, 3-(3-(9-(1-methyl-1H-imidazol-3-ium-3-yl)nonyl)-1H-imidazol-3-ium-1-yl)propyl, 4-(3-decyl-1H-imidazol-3-ium-1-yl)butyl, 4-(1-decyl-1H-imidazol-3-ium-3-yl)butyl, 10-(1-decyl-2-methyl-1H-imidazol-3-ium-3-yl)decyl, 10-(3-decyl-2-methyl-1H-imidazol-3-ium-1-yl)decyl, 3-(1,2-dimethyl-1H-imidazol-3-ium-3-yl)propyl, 3-(2,3-dimethyl-1H-imidazol-3-ium-1-yl)propyl, 10-(2,3-dimethyl-1H-imidazol-3-ium-1-yl)decyl, 10-(1,2-dimethyl-1H-imidazol-3-ium-3-yl)decyl, 10-(1-methyl-1H-imidazol-3-ium-3-yl) decyl, 10-(3-methyl-1H-imidazol-3-ium-1-yl)decyl, 10-(1-butyl-1H-imidazol-3-ium-3-yl)decyl, 10-(3-butyl-1H-imidazol-3-ium-1-yl)decyl, 10-(1-methylpyrrolidinium-1-yl)decyl, 4-amino-2-(tert-butoxycarbonylamino)-1,4-dioxobutyl, 2-(tert-butoxycarbonylamino)-1-oxoethyl, 2-(tert-butoxycarbonylamino)-4-(methylthio)-1-oxobutyl, 5-(3-(methylthio)propylamino)-5-oxopentyl, 2-(tert-butoxycarbonylamino)-3-(4-hydroxyphenyl)-1-oxopropyl, 5-(4-hydroxyphenethylamino)-5-oxopentyl, 2-(tert-butoxycarbonylamino)-1-oxo-3-phenylpropyl, 5-oxo-5-(phenethylamino)pentyl, 2-(tert-butoxycarbonylamino)-3-(1H-imidazol-4-yl)-1-oxopropyl, 5-(2-(1H-imidazol-4-yl) ethylamino)-5-oxopentyl, 2-(tert-butoxycarbonylamino)-3-carboxy-1-oxopropyl, 5-(2-carboxyethylamino)-5-oxopentyl, 2-(tert-butoxycarbonylamino)-3-methyl-1-oxobutyl, 5-(isobutylamino)-5-oxopentyl,(3R)-2-(tert-butoxycarbonylamino)-3-methyl-1-oxopentyl,(R)-5-(2-methylbutylamino)-5-oxopentyl, 2-(tert-butoxycarbonylamino)-3-mercapto-1-oxopropyl, 5-(2-mercaptoethylamino)-5-oxopentyl,(3R)-2-(tert-butoxycarbonylamino)-3-hydroxy-1-oxobutyl,(R)-5-(2-hydroxypropylamino)-5-oxopentyl, 6-amino-2-(tert-butoxycarbonylamino)-1-oxohexyl, 5-(5-aminopentylamino)-5-oxopentyl, 5-amino-2-(tert-butoxycarbonylamino)-1,5-dioxopentyl, 5-(4-amino-4-oxobutylamino)-5-oxopentyl, 2-(tert-A butoxycarbonylamino)-5-guanidino-1-oxopentyl, 2-(tert-butoxycarbonylamino)-3-hydroxy-1-oxopropyl, 5-(2-hydroxyethylamino)-5-oxopentyl, 2-(tert-butoxycarbonylamino)-4-methyl-1-oxopentyl, 5-(isopentylamino)-5-oxopentyl, 2-(tert-butoxycarbonylamino)-4-carboxy-1-oxobutyl, 5-(3-carboxypropylamino)-5-oxopentyl, 2-(tert-butoxycarbonylamino)-1-oxopropyl, 5-(ethylamino)-5-oxopentyl, a ligand of formula 6

$$*—R_{46}—R_{47}—R_{48} \quad (6)$$

or a combination thereof, wherein $R_{46}$ is decylene, $R_{47}$ is 1,3-bis(1-methylpiperidin-4-yl)propane, and $R_{48}$ is decyl.

9. The polymer of claim 8 wherein the ligand is 2-(tert-butoxycarbonylamino)-3-(1H-indol-3-yl)-1-oxopropyl, 5-(2-(4-(nonyloxy)benzamido)ethylamino)-5-oxopentyl, 10-(pyridinium-1-yl)decyl, 5-(2-(1H-indol-3-yl)ethylamino)-5-oxopentyl, 2-amino-3-(1H-indol-2-yl)-1-oxopropyl, 3-(1,2-dimethyl-1H-imidazol-3-ium-3-yl)propyl, 10-(1,2-dimethyl-1H-imidazol-3-ium-3-yl)decyl, 10-(1-methyl-1H-imidazol-3-ium-3-yl)decyl, 3-(thiazol-3-ium-3-yl) propyl, 3-(1-methylpyrrolidinium-1-yl)propyl, 3-(2-methylthiazol-3-ium-3-yl)propyl, 3-(benzo[d]thiazol-3-ium-3-yl)propyl, 3-(tetrahydro-1H-thiophenium-1-yl) propyl, 3-(3-methyl-1H-imidazol-3-ium-1-yl)propyl, 3-(1-methyl-1H-imidazol-3-ium-3-yl)propyl, 3-(3-(3-aminopropyl)-1H-imidazol-3-ium-1-yl)propyl, 3-(1-(3- aminopropyl)-1H-imidazol-3-ium-3-yl)propyl, 3-(3-(5-trimethylammonio)pentyl)-1H-imidazol-3-ium-1-yl)propyl, 3-(1-(5-trimethylammonio)pentyl)-1H-imidazol-3-ium-3-yl)propyl, 3-(3-decyl-1H-imidazol-3-ium-1-yl)propyl, 3-(1-decyl-1H-imidazol-3-ium-3-yl)propyl, 3-(3-(9-(3-methyl-1H-imidazol-3-ium-1-yl)nonyl)-1H-imidazol-3-ium-1-yl)propyl, 3-(1-(9-(1-methyl-1H-imidazol-3-ium-3-yl)nonyl)-1H-imidazol-3-ium-3-yl)propyl, 3-(1-(9-(3-methyl-1H-imidazol-3-ium-1-yl)nonyl)-1H-imidazol-3-ium-3-yl) propyl, 3-(3-(9-(1-methyl-1H-imidazol-3-ium-3-yl)nonyl)-1H-imidazol-3-ium-1-yl)propyl, 4-(3-decyl-1H-imidazol-3-ium-1-yl)butyl, 4-(1-decyl-1H-imidazol-3-ium-3-yl)butyl, 10-(1-decyl-2-methyl-1H-imidazol-3-ium-3-yl)decyl, 10-(3-decyl-2-methyl-1H-imidazol-3-ium-1-yl)decyl, 3-(1,2-dimethyl-1H-imidazol-3-ium-3-yl)propyl, 3-(2,3-dimethyl-1H-imidazol-3-ium-1-yl)propyl, 10-(2,3-dimethyl-1H-imidazol-3-ium-1-yl)decyl, 10-(1,2-dimethyl-1H-imidazol-3-ium-3-yl)decyl, 10-(1-methyl-1H-imidazol-3-ium-3-yl)decyl, 10-(3-methyl-1H-imidazol-3-ium-1-yl)decyl, 10-(1-butyl-1H-imidazol-3-ium-3-yl)decyl, 10-(3-butyl-1H-imidazol-3-ium-1-yl)decyl, 10-(pyridinium-1-yl)decyl, 10-(1-methylpyrrolidinium-1-yl)decyl, a ligand of formula 6

$$*-R_{46}-R_{47}-R_{48} \quad (6)$$

or a combination thereof, wherein $R_{46}$ is decylene, $R_{47}$ is 1,3-bis(1-methylpiperidin-4-yl)propane, and $R_{48}$ is decyl.

10. The polymer of claim 9, wherein the polymer has a swelling ratio of about 0.5 to about 10 grams of water per gram of polymer.

11. The polymer of claim 9, wherein swelling ratio of the polymer is about 2 to about 5 grams of water per gram of polymer.

12. The polymer of claim 10, wherein the polymer is a free flowing powder.

13. A pharmaceutical composition comprising the polymer of claim 1 and a pharmaceutically acceptable excipient.

14. A method of reducing serum LDL-cholesterol in an animal subject comprising administering an effective amount of a pharmaceutical composition of claim 13 to an animal subject in need thereof.

15. The crosslinked amine polymer of claim 1 wherein the amine repeat unit comprises an allyl amine repeat unit of formula 14:

16. The crosslinked amine polymer of claim 1 wherein the amine repeat unit comprises a polyethyleneimine repeat unit of formula 15:

* * * * *